United States Patent
Kim et al.

(10) Patent No.: US 10,792,280 B2
(45) Date of Patent: *Oct. 6, 2020

(54) PHARMACEUTICAL COMPOSITION COMPRISING AMODIAQUINE AND ANTI-DIABETES DRUG AS EFFECTIVE INGREDIENT FOR PREVENTION OR TREATMENT OF DIABETES

(71) Applicants: NOVMETAPHARMA CO., LTD., Seoul (KR); Postech Academy-Industry Foundation, Pohang-si, Gyeongsanbuk-do (KR)

(72) Inventors: Kyong Tai Kim, Pohang-si (KR); Hoe Yune Jung, Pohang-si (KR); Heon Jong Lee, Incheon (KR)

(73) Assignees: NOVMETAPHARMA CO., LTD., Seoul (KR); POSTECH ACADEMY-INDUSTRY FOUNDATION, Pohang-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/324,784

(22) PCT Filed: Aug. 14, 2017

(86) PCT No.: PCT/KR2017/008852
§ 371 (c)(1),
(2) Date: Feb. 11, 2019

(87) PCT Pub. No.: WO2018/030879
PCT Pub. Date: Feb. 15, 2018

(65) Prior Publication Data
US 2019/0175583 A1    Jun. 13, 2019

(30) Foreign Application Priority Data

Aug. 12, 2016 (KR) .................. 10-2016-0103174

(51) Int. Cl.
| | | |
|---|---|---|
| A61K 31/4706 | (2006.01) |
| A61K 45/06 | (2006.01) |
| A61K 31/155 | (2006.01) |
| A61K 31/427 | (2006.01) |
| A61P 1/16 | (2006.01) |
| A61P 9/00 | (2006.01) |
| A61P 3/04 | (2006.01) |
| A61P 3/06 | (2006.01) |
| A61P 3/10 | (2006.01) |

(52) U.S. Cl.
CPC ........ *A61K 31/4706* (2013.01); *A61K 31/155* (2013.01); *A61K 31/427* (2013.01); *A61K 45/06* (2013.01); *A61P 1/16* (2018.01); *A61P 3/04* (2018.01); *A61P 3/06* (2018.01); *A61P 3/10* (2018.01); *A61P 9/00* (2018.01)

(58) Field of Classification Search
CPC ............... A61K 31/155; A61K 31/427; A61K 31/4706; A61K 45/06; A61P 1/16; A61P 3/04; A61P 3/06; A61P 3/10; A61P 9/00
See application file for complete search history.

(56) References Cited

U.S. PATENT DOCUMENTS

| | | | |
|---|---|---|---|
| 8,440,695 B2 | 5/2013 | Kastan et al. | |
| 2009/0181976 A1 | 7/2009 | Buschmann et al. | |
| 2009/0325975 A1* | 12/2009 | Buschmann | A61K 31/00 514/252.12 |
| 2015/0023930 A1 | 1/2015 | Rawat et al. | |

FOREIGN PATENT DOCUMENTS

| | | |
|---|---|---|
| KR | 10-0623322 B1 | 9/2006 |
| KR | 10-2013-0137628 A | 12/2013 |
| KR | 10-1423785 B1 | 7/2014 |
| KR | 10-1668443 B1 | 10/2016 |

OTHER PUBLICATIONS

Jennifer Warner, WebMD, Jun. 8, 2009 (Year: 2009).*
International Search Report for PCT/KR2017/008852 dated Dec. 18, 2017 [PCT/ISA/210].

* cited by examiner

*Primary Examiner* — Jean P Cornet
(74) *Attorney, Agent, or Firm* — Sughrue Mion, PLLC

(57) ABSTRACT

The present invention relates to a pharmaceutical composition for preventing or treating diabetes, and controlling a side effect from peroxisome proliferator-activated receptor-gamma (PPAR-gamma) activation, wherein the pharmaceutical composition comprises (a) an amodiaquine compound or a pharmaceutically acceptable salt thereof and (b) an antidiabetic drug as active ingredients. Specifically, the composition prevents or treats simultaneously one or more selected from the group consisting of type 2 diabetes reactive to PPAR-gamma activation, and obesity, dyslipidemia, cardiovascular diseases, and fatty cirrhosis reactive to peroxisome proliferator-activated receptor-alpha (PPAR-alpha) activation.

8 Claims, 52 Drawing Sheets

Specification includes a Sequence Listing.

SEQUENCE LISTING

```
<160> NUMBER OF SEQ ID NOS: 21

<210> SEQ ID NO 1
<211> LENGTH: 19
<212> TYPE: DNA
<213> ORGANISM: Artificial Sequence
<220> FEATURE:
<223> OTHER INFORMATION: Synthetic construct

<400> SEQUENCE: 1
ctcggaggac agtactccg                                               19

<210> SEQ ID NO 2
<211> LENGTH: 18
<212> TYPE: DNA
```

```
<213> ORGANISM: Artificial Sequence
<220> FEATURE:
<223> OTHER INFORMATION: beta-actin forward primer

<400> SEQUENCE: 2
gggaaggtga cagcattg                                                 18

<210> SEQ ID NO 3
<211> LENGTH: 23
<212> TYPE: DNA
<213> ORGANISM: Artificial Sequence
<220> FEATURE:
<223> OTHER INFORMATION: beta-actin reverse primer

<400> SEQUENCE: 3
atgaagtatt aaggcggaag att                                           23

<210> SEQ ID NO 4
<211> LENGTH: 24
<212> TYPE: DNA
<213> ORGANISM: Artificial Sequence
<220> FEATURE:
<223> OTHER INFORMATION: ACOX forward primer

<400> SEQUENCE: 4
acactaacat atcaacaaga ggag                                          24

<210> SEQ ID NO 5
<211> LENGTH: 18
<212> TYPE: DNA
<213> ORGANISM: Artificial Sequence
<220> FEATURE:
<223> OTHER INFORMATION: ACOX reverse primer

<400> SEQUENCE: 5
cattgccagg aagaccag                                                 18

<210> SEQ ID NO 6
<211> LENGTH: 19
<212> TYPE: DNA
<213> ORGANISM: Artificial Sequence
<220> FEATURE:
<223> OTHER INFORMATION: CPT-1 forward primier

<400> SEQUENCE: 6
ccacctcttc tgcctctat                                                19

<210> SEQ ID NO 7
<211> LENGTH: 22
<212> TYPE: DNA
<213> ORGANISM: Artificial Sequence
<220> FEATURE:
<223> OTHER INFORMATION: CPT-1 reverse primer

<400> SEQUENCE: 7
ttctcaaagt caaacagttc ca                                            22

<210> SEQ ID NO 8
<211> LENGTH: 18
<212> TYPE: DNA
<213> ORGANISM: Artificial Sequence
<220> FEATURE:
<223> OTHER INFORMATION: mCAD forward primer

<400> SEQUENCE: 8
ccgaagagtt ggcgtatg                                                 18
```

<210> SEQ ID NO 9
<211> LENGTH: 19
<212> TYPE: DNA
<213> ORGANISM: Artificial Sequence
<220> FEATURE:
<223> OTHER INFORMATION: mCAD reverse primer

<400> SEQUENCE: 9
agcaagaatc acaggcatt                                                    19

<210> SEQ ID NO 10
<211> LENGTH: 20
<212> TYPE: DNA
<213> ORGANISM: Artificial Sequence
<220> FEATURE:
<223> OTHER INFORMATION: TNFalpha forward primer

<400> SEQUENCE: 10
atgagaagtt cccaaatggc                                                   20

<210> SEQ ID NO 11
<211> LENGTH: 25
<212> TYPE: DNA
<213> ORGANISM: Artificial Sequence
<220> FEATURE:
<223> OTHER INFORMATION: TNFalpha reverse primer

<400> SEQUENCE: 11
tttgagaaga tgatctgagt gtgag                                             25

<210> SEQ ID NO 12
<211> LENGTH: 18
<212> TYPE: DNA
<213> ORGANISM: Artificial Sequence
<220> FEATURE:
<223> OTHER INFORMATION: MCP-1 forward primer

<400> SEQUENCE: 12
aatgagtagg ctggagag                                                     18

<210> SEQ ID NO 13
<211> LENGTH: 18
<212> TYPE: DNA
<213> ORGANISM: Artificial Sequence
<220> FEATURE:
<223> OTHER INFORMATION: MCP-1 reverse primer

<400> SEQUENCE: 13
tctcttgagc ttggtgac                                                     18

<210> SEQ ID NO 14
<211> LENGTH: 18
<212> TYPE: DNA
<213> ORGANISM: Artificial Sequence
<220> FEATURE:
<223> OTHER INFORMATION: iNOS forward primer

<400> SEQUENCE: 14
gcttctggca ctgagtaa                                                     18

<210> SEQ ID NO 15
<211> LENGTH: 18
<212> TYPE: DNA
<213> ORGANISM: Artificial Sequence
<220> FEATURE:

<223> OTHER INFORMATION: iNOS reverse primer

<400> SEQUENCE: 15
ggaggagagg agagagat                                                 18

<210> SEQ ID NO 16
<211> LENGTH: 20
<212> TYPE: DNA
<213> ORGANISM: Artificial Sequence
<220> FEATURE:
<223> OTHER INFORMATION: PEPCK forward primer

<400> SEQUENCE: 16
cagttgagta gcacagagaa                                               20

<210> SEQ ID NO 17
<211> LENGTH: 20
<212> TYPE: DNA
<213> ORGANISM: Artificial Sequence
<220> FEATURE:
<223> OTHER INFORMATION: PEPCK reverse primer

<400> SEQUENCE: 17
gattcctgag tgaccttgaa                                               20

<210> SEQ ID NO 18
<211> LENGTH: 19
<212> TYPE: DNA
<213> ORGANISM: Artificial Sequence
<220> FEATURE:
<223> OTHER INFORMATION: SREBP-1 forward primer

<400> SEQUENCE: 18
cgactacatc cgcttcttg                                                19

<210> SEQ ID NO 19
<211> LENGTH: 20
<212> TYPE: DNA
<213> ORGANISM: Artificial Sequence
<220> FEATURE:
<223> OTHER INFORMATION: SREBP-1 reverse primer

<400> SEQUENCE: 19
ggtccttcag tgatttgctt                                               20

<210> SEQ ID NO 20
<211> LENGTH: 18
<212> TYPE: DNA
<213> ORGANISM: Artificial Sequence
<220> FEATURE:
<223> OTHER INFORMATION: GLUT4 forward primer

<400> SEQUENCE: 20
aaatctagcc ctgcctcc                                                 18

<210> SEQ ID NO 21
<211> LENGTH: 18
<212> TYPE: DNA
<213> ORGANISM: Artificial Sequence
<220> FEATURE:
<223> OTHER INFORMATION: GLUT4 reverse primer

<400> SEQUENCE: 21
gctctaaccg tccttgcc                                                 18

PHARMACEUTICAL COMPOSITION COMPRISING AMODIAQUINE AND ANTI-DIABETES DRUG AS EFFECTIVE INGREDIENT FOR PREVENTION OR TREATMENT OF DIABETES

CROSS REFERENCE TO RELATED APPLICATIONS

This application is a National Stage of International Application No. PCT/KR2017/008852, filed on Aug. 14, 2017, which claims priority from Korean Patent Application No. 10-2016-0103174, filed on Aug. 12, 2016.

TECHNICAL FIELD

The present invention relates to a pharmaceutical composition for preventing or treating diabetes, which includes, as active ingredients, amodiaquine that activates both PPAR-γ and PPAR-α, and an antidiabetic drug.

BACKGROUND ART

Diabetes refers to symptoms in which hyperglycemia is caused by the accumulation of glucose in blood due to non-use of glucose in blood as energy that results from the inability to produce insulin, which is a glucose-regulating hormone secreted by pancreatic beta cells, in an amount required in the body, or the inability of insulin to properly function in cells, and glucose is detected in urine. Generally, diabetes is classified into insulin-dependent diabetes (type 1 diabetes) and insulin non-dependent diabetes (type 2 diabetes) depending on whether insulin is required for treatment. Type 2 diabetes, which is non-insulin-dependent diabetes, occurs as a result of insufficient insulin action due to insulin resistance, or a relative lack of insulin, and 90% of a total number of diabetic patients belong to type 2 diabetes, and type 2 diabetes is also referred to as adult diabetes since it occurs mainly after one's thirties.

When diabetes is long-lasting, the absorption of glucose in the body does not occur normally, and thus causes disorders in carbohydrate metabolism, lipid metabolism, and protein metabolism, resulting in the occurrence of various diabetic complications such as hyperinsulinemia, renal complications, diabetic retinopathy (non-proliferative retinopathy, proliferative retinopathy, and diabetic cataract), kidney failure, sexual dysfunction, skin diseases (allergy), hypertension, arteriosclerosis, a stroke (apoplexy), heart diseases (a cardiac infarction, angina, and heart attack), and gangrene. Therefore, in order to understand various causes and etiologies of type 2 diabetes and prepare improvement measures, research into glucose transport and metabolism pathways, insulin signal transduction mechanisms, and the like has been actively conducted domestically and globally, but drugs capable of fundamentally treating type 2 diabetes have not yet been developed. Currently known type 2 diabetes therapeutic agents can be broadly classified into four types: sulfonylureas that induce the secretion of insulin; biguanides that deliver glucose to muscle cells and have an effect of inhibiting the synthesis of glucose in the liver; α-glucosidase inhibitors that inhibit a glucose-producing enzyme in the small intestine; thiazolidinedione (TZD)-based drugs that activate peroxisome proliferator-activated receptor (PPAR)-γ associated with adipocyte differentiation; and the like. However, these oral hypoglycemic drugs have many side effects such as hypoglycemia induction (sulfonylureas), nephrotoxicity (biguanides), lactic acidosis (biguanides), diarrhea and a stomachache (α-glucosidase inhibitors), and the like.

Meanwhile, peroxisomes are one of the intracellular organelles responsible for these metabolic abnormalities, play an important role in the metabolism of oxygen, glucose, lipids, and hormones, and also widely affect the regulation of cell proliferation and differentiation, and the regulation of inflammatory mediators. In addition, peroxisomes affect not only insulin sensitivity but also the formation of cell membranes and mast cells through lipid metabolism and glucose metabolism, and play an important role in aging and tumor development by affecting oxidative stress. Peroxisome proliferator-activated receptors (PPARs) are one of the nuclear receptors that regulate gene expression by ligand bonding, and various fatty acids act as endogenous ligands. Examples of currently identified PPARs include peroxisome proliferator-activated receptor-alpha (PPAR-α), peroxisome proliferator-activated receptor-beta/delta (PPAR-β/δ), and peroxisome proliferator-activated receptor-gamma (PPAR-γ).

PPAR-γ is found predominantly in adipose tissue and is also found in vascular endothelial cells, macrophages, and pancreatic P cells, and regulates adipocyte differentiation and plays a crucial role in systemic lipid homeostasis. A totally- or partially-activating compound of PPAR-γ is particularly effective in the treatment of type 2 diabetes. However, upon activation of PPAR-γ, side effects such as obesity, dyslipidemia, a cardiovascular disease, fatty liver, and the like occur.

PPAR-α is found mainly in blood vessel walls, the liver, the heart, muscle, the kidneys, brown adipose tissue, and the like, and prevents arteriosclerosis or delays the onset thereof along with fibrates as an agonist, and has an anti-obesity effect through fat oxidation promotion.

Therefore, there is a need to discover a novel compound capable of more effectively regulating the activity of PPARs, in order to prevent, alleviate, or treat various diseases regulated by the action of PPARs.

Thus, the inventors of the present invention became aware of amodiaquine while conducting research to find a compound having excellent antidiabetic activity and being safely applicable.

Amodiaquine is an antimalarial compound, and there are several reports of studies in which it was used as a therapeutic agent for malaria. In addition, examples of conventional techniques for amodiaquine, which are registered patents, include an orally administrable antimalarial combined preparation and a preparation method thereof (KR 10-0623322), piperazine derivatives as an antimalarial agent (KR 10-1423785), and the like.

However, there are no studies on and techniques for a combined preparation of amodiaquine and an antidiabetic drug, in order to inhibit obesity, dyslipidemia, a cardiovascular disease, fatty liver, and the like, which are diseases regulated by the action of PPARs and occur as side effects upon activation of PPAR-γ, and also prevent or treat diabetes.

DISCLOSURE

Technical Problem

An object of the present invention is to provide a novel use of a composition including, as active ingredients, (a) an amodiaquine compound or a pharmaceutically acceptable salt thereof; and (b) an antidiabetic drug, i.e., a novel use of the composition for inhibiting side effects caused by PPAR-γ activation and also preventing or treating diabetes.

However, technical problems to be solved by the present invention are not limited to the above-described technical problem, and other unmentioned technical problems will become apparent from the following description to those of ordinary skill in the art.

Technical Solution

The prevent invention provides a pharmaceutical composition for inhibiting side effects due to the activation of peroxisome proliferator-activated receptor-gamma (PPAR-γ) and preventing or treating diabetes, including as active ingredients: (a) amodiaquine represented by Formula 1 below or a pharmaceutically acceptable salt thereof; and (b) at least one antidiabetic drug selected from the group consisting of:

a biguanide drug selected from the group consisting of metformin, buformin, and phenformin;

an insulin sensitizer selected from the group consisting of troglitazone, ciglitazone, rosiglitazone, pioglitazone, and englitazone;

a dipeptidyl peptidase 4 (DPP-4) inhibitor selected from the group consisting of sitagliptin, linagliptin, vildagliptin, gemigliptin, saxagliptin, alogliptin, teneligliptin, anagliptin, and evogliptin;

a sodium-glucose co-transporter 2 (SGLT2) inhibitor selected from the group consisting of dapagliflozin, canagliflozin, empagliflozin, ipragliflozin, tofogliflozin, luseogliflozin, remogliflozin, remogliflozin etabonate, and ertugliflozin;

a glucagon-like peptide 1 (GLP1) agonist selected from the group consisting of exenatide, lixisenatide, liraglutide, albiglutide, and dulaglutide;

an insulin secretagogue selected from the group consisting of glybenclamide (glyburide), glipizide, gliclazide, glimepiride, tolazamide, tolbutamide, acetohexamide, carbutamide, chlorpropamide, glibornuride, gliquidone, glisentide, glisolamide, glisoxepide, glyclopyamide, glycylamide, glipentide, repaglinide, and nateglinide;

an α-glucosidase inhibitor selected from the group consisting of acarbose, voglibose, emiglitate, and miglitol;

a cannabinoid receptor 1 antagonist selected from the group consisting of rimonabant, otenabant, ibinabant, and surinabant; and a composition including cyclo-his-pro, or a zinc salt and cyclo-his-pro:

[Formula 1]

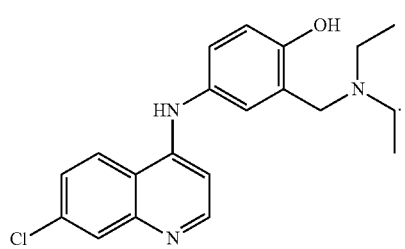

The composition may be intended to simultaneously prevent or treat type 2 diabetes that responds to peroxisome proliferator-activated receptor-gamma (PPAR-γ) activation and one or more selected from the group consisting of obesity, dyslipidemia, a cardiovascular disease, and fatty liver, which respond to PPAR-α activation.

The dyslipidemia may be one or more selected from the group consisting of hyperlipidemia, hypertriglyceridemia, and hypercholesterolemia.

A weight ratio of the amodiaquine and the antidiabetic drug may range from 1:0.01 to 1:500.

A daily dose of the composition may range from 8 mg/kg to 20 mg/kg.

Advantageous Effects

A pharmaceutical composition for inhibiting side effects due to PPAR-γ activation and preventing or treating diabetes, according to the present invention includes as active ingredients: (a) an amodiaquine compound or a pharmaceutically acceptable salt thereof; and (b) an antidiabetic drug, and amodiaquine can promote the activity of PPAR-α and PPAR-γ.

Thus, in the case of a combined preparation obtained by mixing such amodiaquine or a pharmaceutically acceptable salt thereof with an antidiabetic drug such as a biguanide, e.g., metformin or the like, it has a great synergistic effect on gluconeogenesis inhibition and the inhibition of triglyceride and phospholipid biosynthesis associated with lipid metabolism as compared to a single agent, and thus it is anticipated that the composition of the present invention can be effectively useful in simultaneously preventing or treating type 2 diabetes that responds to PPAR-γ activation and one or more selected from the group consisting of obesity, dyslipidemia, a cardiovascular disease, and fatty liver, which respond to PPAR-α activation.

BEST MODE

Figure 1A:
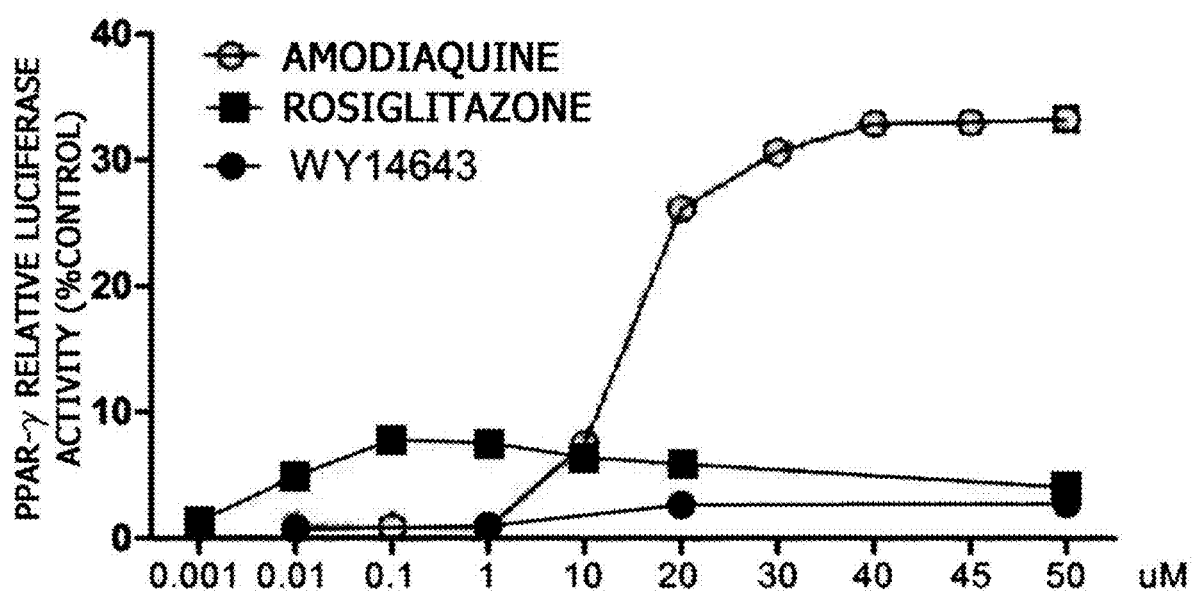
FIGS. 1A and 1B are graphs showing results of measuring a PPAR-γ activation effect of amodiaquine.

The inventors of the present invention verified that a combined preparation, which was prepared by mixing amodiaquine capable of activating both PPAR-α and PPAR-γ or a pharmaceutically acceptable salt thereof with an antidiabetic drug, exhibited a significant synergistic effect on blood glucose regulation and fat accumulation inhibition (especially, the inhibition of triglyceride accumulation in liver tissue), as compared to a single preparation, and thus could inhibit side effects due to PPAR-γ activation and prevent or treat diabetes, and thus completed the present invention based on these findings.

In one embodiment of the present invention, to examine whether amodiaquine acts as a double ligand for PPAR-γ and PPAR-α, the activity of PPAR-γ and PPAR-α was measured using vectors (see Example 1), and to examine whether an increase in the glucose uptake of amodiaquine affects a decrease in blood glucose, an experiment for evaluating glucose uptake in a mouse muscle cell line was carried out (see Example 2). In addition, it was examined whether amodiaquine exhibited effects of lowering and regulating blood glucose, reducing glycated hemoglobin (HbA1C), reducing a body weight, producing heat, and preventing fatty liver in mice (see Examples 3 to 8). In addition, it was confirmed that amodiaquine administration could promote fatty acid degradation by regulating the expression of target genes (ACOX, CPT-1, and mCAD) by PPAR-α activation in liver, muscle, and adipose tissues (see Example 9), and it was confirmed that amodiaquine administration could inhibit the expression of target genes (TNFα, MCP-1, and iNOS) by anti-inflammatory responses in adipose tissue (see Example 10).

As a result, it was confirmed that the activation of PPAR-γ and PPAR-L by amodiaquine treatment and a series of subsequent responses were effective in regulating blood glucose and inhibiting fat accumulation.

Meanwhile, in another embodiment of the present invention, a synergistic effect of a combined preparation of amodiaquine and metformin on inhibiting gluconeogenesis upon treatment therewith was measured (see Example 11), and a synergistic effect of the combined preparation on inhibiting triglyceride and phospholipid biosynthesis associated with lipid metabolism was measured (see Example 12), and it was confirmed that the combined preparation could increase the expression of the GLUT4 gene in muscle cells in a palmitic acid-induced insulin resistance state (see Example 13).

In addition, in another embodiment of the present invention, it was confirmed that when a combined preparation of amodiaquine and sitagliptin was administered to mice, it exhibited an effect of regulating blood glucose (see Example 14). In another embodiment of the present invention, it was confirmed that the combined preparation of amodiaquine and sitagliptin exhibited an effect of lowering and regulating blood glucose and affected glycated hemoglobin content, when administered to mice (see Example 15). In another embodiment of the present invention, it was confirmed that a combined preparation of amodiaquine and dapagliflozin exhibited an effect of lowering and regulating blood glucose and affected glycated hemoglobin content, when administered to mice (see Example 16). In another embodiment of the present invention, it was confirmed that a combined preparation of amodiaquine and exenatide exhibited an effect of regulating blood glucose, when administered to mice (see Example 17).

From the above-described results, it was confirmed that upon treatment with a combined preparation of amodiaquine and an antidiabetic drug, there was a significant synergistic effect on regulating blood glucose and inhibiting fat accumulation (particularly, the inhibition of triglyceride accumulation in liver tissue), as compared to the case of treatment with a single preparation.

Therefore, the present invention provides a pharmaceutical composition for inhibiting side effects due to the activation of peroxisome proliferator-activated receptor-gamma (PPAR-γ) and preventing or treating diabetes, including as active ingredients: (a) amodiaquine represented by Formula 1 below or a pharmaceutically acceptable salt thereof; and (b) at least one antidiabetic drug selected from the group consisting of:

a biguanide drug selected from the group consisting of metformin, buformin, and phenformin;

an insulin sensitizer selected from the group consisting of troglitazone, ciglitazone, rosiglitazone, pioglitazone, and englitazone;

a dipeptidyl peptidase 4 (DPP-4) inhibitor selected from the group consisting of sitagliptin, linagliptin, vildagliptin, gemigliptin, saxagliptin, alogliptin, teneligliptin, anagliptin, and evogliptin;

a sodium-glucose co-transporter 2 (SGLT2) inhibitor selected from the group consisting of dapagliflozin, canagliflozin, empagliflozin, ipragliflozin, tofogliflozin, luseogliflozin, remogliflozin, remogliflozin etabonate, and ertugliflozin;

a glucagon-like peptide 1 (GLP1) agonist selected from the group consisting of exenatide, lixisenatide, liraglutide, albiglutide, and dulaglutide;

an insulin secretagogue selected from the group consisting of glybenclamide (glyburide), glipizide, gliclazide, glimepiride, tolazamide, tolbutamide, acetohexamide, carbutamide, chlorpropamide, glibornuride, gliquidone, glisentide, glisolamide, glisoxepide, glyclopyamide, glycylamide, glipentide, repaglinide, and nateglinide;

an α-glucosidase inhibitor selected from the group consisting of acarbose, voglibose, emiglitate, and miglitol;

a cannabinoid receptor 1 antagonist selected from the group consisting of rimonabant, otenabant, ibinabant, and surinabant; and a composition including cyclo-his-pro, or a zinc salt and cyclo-his-pro:

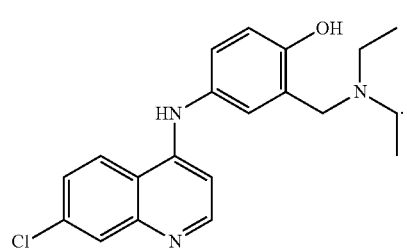

[Formula 1]

The antidiabetic drugs are drugs being currently developed clinically or commercially available drugs, and specific examples thereof include a biguanide drug, an insulin sensitizer, a DPP-4 inhibitor, a sodium-glucose co-transporter 2 (SGLT2) inhibitor, a glucagon-like peptide 1 (GLP1) agonist, an insulin secretagogue, an α-glucosidase inhibitor, a cannabinoid receptor 1 antagonist, and a composition including cyclo-his-pro, or a zinc salt and cyclo-his-pro. Preferably, examples of the antidiabetic drugs include, but are not limited to, a biguanide drug, a DPP-4 inhibitor, a sodium-glucose co-transporter 2 (SGLT2) inhibitor, and a glucagon-like peptide 1 (GLP1) agonist.

More particularly, the biguanide drug may be selected from the group consisting of metformin, buformin, and phenformin; the insulin sensitizer may be selected from the group consisting of troglitazone, ciglitazone, rosiglitazone, pioglitazone, and englitazone; the dipeptidyl peptidase 4 (DPP-4) inhibitor may be selected from the group consisting of sitagliptin, linagliptin, vildagliptin, gemigliptin, saxagliptin, alogliptin, teneligliptin, anagliptin, and evogliptin; the sodium-glucose co-transporter 2 (SGLT2) inhibitor may be selected from the group consisting of canagliflozin, dapagliflozin, empagliflozin, ipragliflozin, tofogliflozin, luseogliflozin, remogliflozin, remogliflozin etabonate, and ertugliflozin; the glucagon-like peptide 1 (GLP1) agonist may be selected from the group consisting of exenatide, lixisenatide, liraglutide, albiglutide, and dulaglutide; the insulin secretagogue may be selected from the group consisting of glybenclamide (glyburide), glipizide, gliclazide, glimepiride, tolazamide, tolbutamide, acetohexamide, carbutamide, chlorpropamide, glibornuride, gliquidone, glisentide, glisolamide, glisoxepide, glyclopyamide, glycylamide, glipentide, repaglinide, and nateglinide; the α-glucosidase inhibitor may be selected from the group consisting of acarbose, voglibose, emiglitate, and miglitol; and the cannabinoid receptor 1 antagonist may be selected from the group consisting of rimonabant, otenabant, ibinabant, and surinabant.

Meanwhile, in the composition including cyclo-his-pro or a zinc salt and cyclo-his-pro, cyclo-his-pro purified as zinc and an enzyme for promoting zinc metabolism may be used as the cyclo-his-pro, and the zinc salt may include zinc cations and anions such as chlorides, sulfates, and the like. Such a composition may promote insulin degrading enzyme (IDE) synthesis and increase activity, thereby enhancing insulin resistance.

That is, even in a case in which amodiaquine or a pharmaceutically acceptable salt thereof is used as a single preparation, or an antidiabetic drug such as a biguanide drug, e.g., metformin or the like is used as a single preparation, it somewhat exhibits an effect of regulating blood glucose and inhibiting fat accumulation, but the effect is insignificant. On the other hand, a combined preparation of the above materials may have a significant synergistic effect on regulating blood glucose and inhibiting fat accumulation (particularly, the inhibition of triglyceride accumulation in liver tissue).

A composition including such a combined preparation may be intended to simultaneously prevent or treat type 2 diabetes that responds to PPAR-γ activation and one or more selected from the group consisting of obesity, dyslipidemia, a cardiovascular disease, and fatty liver, which respond to PPAR-α activation. The one or more selected from the group consisting of obesity, dyslipidemia, a cardiovascular disease, and fatty liver may be regarded as a side effect resulting from PPAR-γ activation. In this regard, the dyslipidemia may be one or more selected from the group consisting of hyperlipidemia, hypertriglyceridemia, and hypercholesterolemia.

A weight ratio of the amodiaquine and the antidiabetic drug may range from 1:0.01 to 1:500. In particular, when the antidiabetic drug is a biguanide drug, the weight ratio of the amodiaquine and the antidiabetic drug may be in a range of 1:50 to 1:500, more preferably in a range of 1:300 to 1:500, but the present invention is limited thereto. In addition, when the antidiabetic drug is a DPP-4 inhibitor, the weight ratio of the amodiaquine and the antidiabetic drug may be in a range of 1:1 to 1:20, more preferably in a range of 1:10 to 1:20, but the present invention is not limited thereto. In addition, when the antidiabetic drug is a sodium-glucose co-transporter 2 (SGLT2) inhibitor, the weight ratio of the amodiaquine and the antidiabetic drug may be in a range of 1:0.02 to 1:2, more preferably in a range of 1:1 to 1:2, but the present invention is not limited thereto. In addition, when the antidiabetic drug is a glucagon-like peptide 1 (GLP1) agonist, the weight ratio of the amodiaquine and the antidiabetic drug may be in a range of 1:0.01 to 1:0.05, more preferably in a range of 1:0.02 to 1:0.05, but the present invention is not limited thereto.

In this regard, when the weight of the amodiaquine is too large, problems due to cytotoxicity occur, and when the weight of the antidiabetic drug is too large, a relative weight of the amodiaquine decreases, and thus PPAR-γ and PPAR-α are unable to be sufficiently activated.

The term "treatment" as used herein means all actions that alleviate or beneficially change symptoms due to diabetes via administration of the pharmaceutical composition according to the present invention.

Thus, the pharmaceutical composition may further include a commonly used suitable carrier, excipient or diluent. In addition, the pharmaceutical composition may be formulated in the form of oral preparations such as powder, granules, tablets, capsules, suspensions, emulsions, syrups, aerosols, and the like, preparations for external application, suppositories, and sterile injection solutions, according to general methods.

Examples of carriers, excipients and diluents that may be included in the composition include lactose, dextrose, sucrose, sorbitol, mannitol, xylitol, erythritol, maltitol, starch, acacia gum, alginates, gelatin, calcium phosphate, calcium silicate, cellulose, methyl cellulose, micro-crystalline cellulose, polyvinylpyrrolidone, water, methylhydroxy benzoate, propylhydroxy benzoate, talc, magnesium stearate, mineral oil, and the like. In addition, the composition may be formulated using commonly used diluents or excipients such as a filler, an extender, a binder, a wetting agent, a disintegrating agent, a surfactant, and the like.

The pharmaceutical composition according to the present invention is administered in a pharmaceutically effective amount. The term "pharmaceutically effective amount" as used herein refers to an amount sufficient to treat diseases at a reasonable benefit/risk ratio applicable to medical treatment, and an effective dosage level may be determined according to factors including type of diseases of patients, the severity of disease, the activity of drugs, sensitivity to drugs, administration time, administration routes, excretion rate, treatment periods, and simultaneously used drugs, and other factors well known in the medical field.

To enhance therapeutic effects, the pharmaceutical composition according to the present invention may be administered simultaneously, separately, or sequentially with a drug used in combination therewith, and may be administered in a single dose or multiple doses. It is important to administer the pharmaceutical composition in the minimum amount that enables achievement of the maximum effects without side effects in consideration of all the above-described factors, and this may be easily determined by those of ordinary skill in the art. In particular, an effective amount of the pharmaceutical composition according to the present invention may vary according to the age, gender, condition, and body weight of a patient, the absorption, inactivity, and excretion rate of active ingredients in the body, the type of disease, and simultaneously used drugs.

The pharmaceutical composition of the present invention may be administered to an individual via various routes. All administration methods may be expected, and may be, for example, oral administration, intranasal administration, transbronchial administration, arterial administration, intravenous administration, subcutaneous injection, intramuscular injection, or intraperitoneal injection. A daily dose of the pharmaceutical composition may range from about 0.0001 mg/kg to about 100 mg/kg, preferably 8 mg/kg to 20 mg/kg and may be administered once or multiple times a day, but the present invention is not limited thereto. When the daily dose of the pharmaceutical composition is in a range of 8 mg/kg to 20 mg/kg, both PPAR-γ and PPAR-α may be activated, and problems due to cytotoxicity may also be minimized.

The dosage of the pharmaceutical composition of the present invention is determined according to various related factors such as a disease to be treated, administration routes, the age, gender, and body weight of a patient, the severity of disease, and the like, and the type of drug, which is an active ingredient.

According to another embodiment of the present invention, there is provided a method of inhibiting a side effect due to PPAR-γ activation and treating diabetes, including administering the pharmaceutical composition to an individual.

The term "individual" as used herein refers to a subject with a disease requiring treatment and, more particularly, includes mammals such as humans, non-human primates, mice, rats, dogs, cats, horses, cows, and the like.

Furthermore, the present invention provides a use of the pharmaceutical composition for inhibiting a side effect due to PPAR-γ activation and preventing or treating diabetes.

Hereinafter, exemplary embodiments will be described to aid in understanding of the present invention. However, the following examples are provided only to facilitate the understanding of the present invention and are not intended to limit the scope of the present invention.

PREPARATION EXAMPLE

For drugs used in the following examples, amodiaquine and metformin were purchased from Sigma-Aldrich, sitagliptin was purchased from Cayman Chemical, and dapagliflozin and exenatide were purchased from SUNGWOO BIOPHARM CORPORATION.

EXAMPLES

Example 1. Measurement of PPAR-γ or PPAR-α Activation by Amodiaquine

To examine whether amodiaquine acts as a ligand of PPAR-λ or PPAR-α, three types of vectors were used. An experiment was carried out according to a known method (Cell, 68: 879-887, 1992) using a vector prepared by binding genes expressing a GAL4-DBD (DNA binding domain), which is a yeast transcription factor, and a human PPAR-λ-ligand binding domain (LBD) or PPAR-α-LBD to a SV40 promoter of a pZeo vector, a vector prepared by binding a gene in which a GAL4 gene-binding base sequence (5'-CTCGGAGGACAGTACTCCG-3')(SEQ ID NO: 1) is repeated 8 times to luciferase, which is a reporter gene, and a vector expressing β-galactosidase as a transfection control.

The activation of luciferase expression was measured after BE(2)C cells were transformed with a GAL4-PPAR-γ-LBD plasmid or a GAL4-PPAR-α-LBD plasmid, a GAL4-luciferase vector, and a β-galactosidase vector for 6 hours, treated with amodiaquine for 20 hours, and then grown in a 5% $CO_2$ incubator. At this time, an experimental group co-treated with amodiaquine at various concentrations (0.01 µM to 50 µM), a control treated with 0.3% dimethyl sulfoxide (DMSO), a positive control co-treated with a compound known as a PPAR-γ ligand, rosiglitazone (Sigma, USA), at various concentrations (0.001 µM to 50 µM), a positive control co-treated with a compound known as a PPAR-α ligand, WY-14,643 (Sigma, USA), at various concentrations (0.01 µM to 50 µM), and a positive control co-treated with 7-chloro-4-(4-diethylamino-1-methylbutylamino)quinolone (chloroquine) (Sigma, USA), which is a compound known as an amodiaquine derivative, at various concentrations (0.001 µM to 50 µM) were compared. For the experimental results, the significance of the experimental group and the controls was verified using a t-test, and the groups showed statistically significant differences.

Figure 1B:
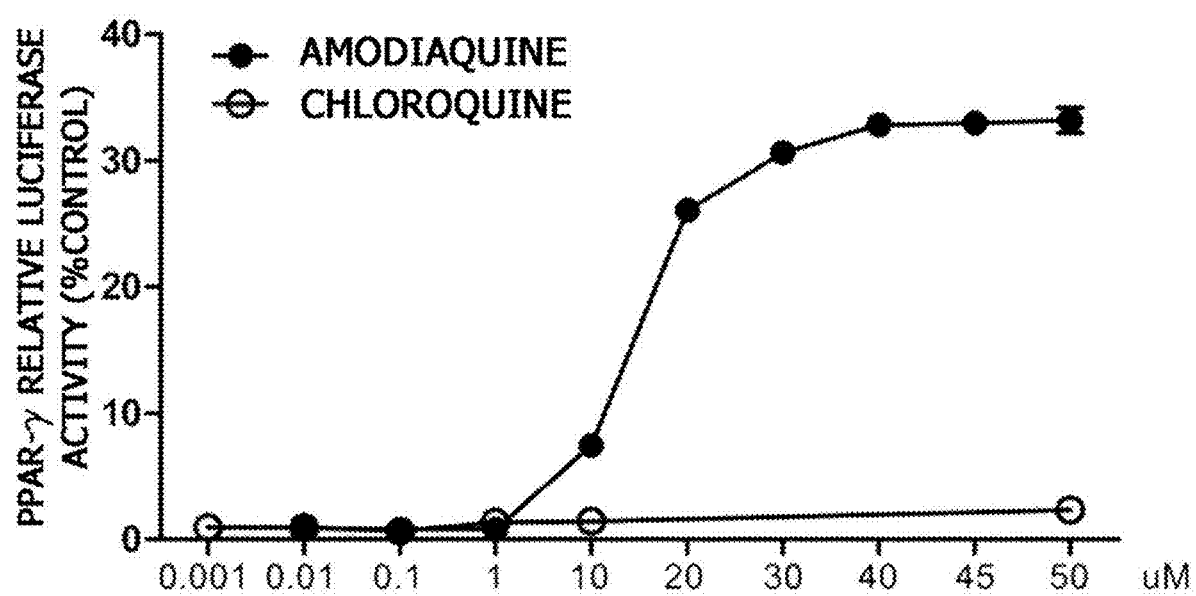
Figure 1C:
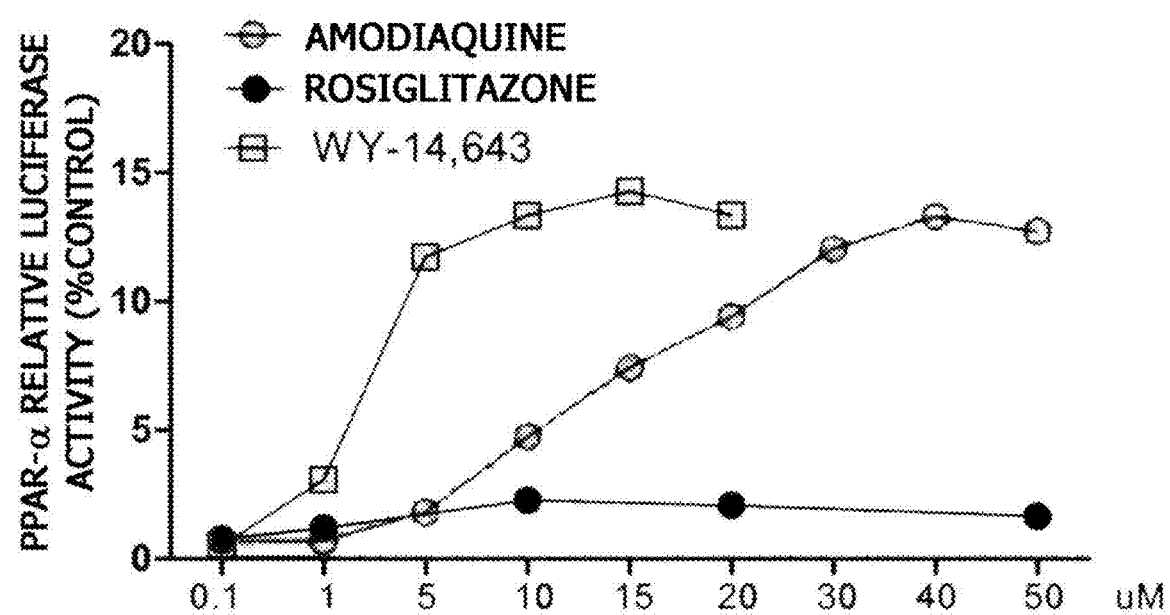
FIGS. 1C and 1D are graphs showing results of measuring a PPAR-α activation effect.

As a result, as illustrated in FIGS. 1A and 1B, while the group treated with amodiaquine exhibited a higher PPAR-γ activity in a concentration-dependent manner than that of the positive control treated with rosiglitazone, which is a compound known as a PPAR-γ ligand, the positive control treated with WY-14,643, which is a compound known as a PPAR-α ligand, and chloroquine, which is a compound known as an amodiaquine derivative, did not exhibit PPAR-γ activity. In addition, as illustrated in FIGS. 1C and 1D, it was seen that similar to the positive control treated with WY-14,643, which is a compound known as a PPAR-α ligand, the group treated with amodiaquine exhibited a high PPAR-α activity in a concentration-dependent manner, but no PPAR-α activity was exhibited in the positive control treated with rosiglitazone, which is a compound known as a PPAR-γ ligand and chloroquine, which is a compound known as an amodiaquine derivative.

Therefore, it was confirmed that the amodiaquine treatment had an effect of promoting the activity of both PPAR-γ and PPAR-α, and it can be seen that the amodiaquine may be used to prevent or treat type 2 diabetes, which is a PPAR-γ-associated disease and may be used to prevent or treat obesity, dyslipidemia, a cardiovascular disease, fatty liver, or the like, which is regulated by PPAR-α signals.

Figure 1D:
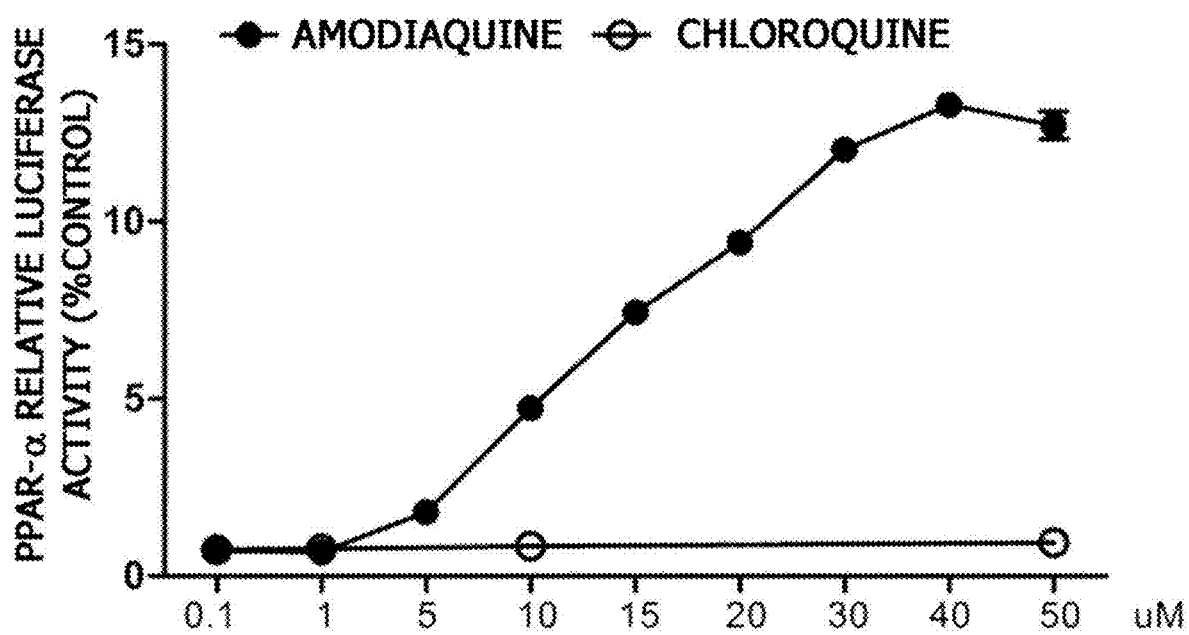

From the results of FIGS. 1B and 1D, it can also be seen that amodiaquine promotes the activity of both PPAR-γ and PPAR-α because of a structural characteristic in which a benzene ring and a hydroxyl group are substituted, but the amodiaquine derivative does not promote the same activity.

Example 2. Measurement of Glucose Uptake Effect of Amodiaquine in C2C12 Myotube Cells The phosphorylation of insulin receptors occurs due to signal transduction by insulin in muscle, adipose, liver cells, and the like, and accordingly, when various proteins located downstream are phosphorylated, glucose uptake increases, resulting in reduced blood glucose. Thus, a glucose uptake evaluation experiment was carried out to identify whether amodiaquine is effective for diabetes. C2C12 myoblasts, which are muscle cells, were cultured in DMEM containing 10% bovine serum albumin (BSA). When the cell density reached about 80% to about 90%, the medium was replaced with fresh 2% horse serum-containing DMEM, and cell differentiation of the C2C12 myoblasts into myotubes was induced to completely differentiate the cells, and then an experiment was carried out. The completely differentiated C2C12 myotube cells were treated with a well-mixed mixture of 10 µM or 30 µM amodiaquine, 0.1% dimethyl sulfoxide (DMSO), and 50 µM rosiglitazone (Sigma, USA), which is a compound known as a positive control for glucose uptake, in 0.5% BSA-containing DMEM for 24 hours. After 24 hours of the treatment, the medium was removed, the cells were washed with 3 ml of KRP (0.1% BSA+5 mM glucose) buffer on a plate maintained at 37° C. to remove the remaining sample. Washing was repeated three times every twenty minutes. Subsequently, 1 ml of KRP buffer was injected, a solution (0.2 mM, 0.2 µCi) prepared by dissolving unlabeled 2-DOG and [$^3$H]2-DOG (Amersham Pharmacia) in KRP buffer was added to the resulting cells at 37° C. to allow treatment for exactly 10 minutes. The resulting cells were washed with 3 ml of cold phosphate buffered saline (PBS) to stop a glucose uptake reaction, further washed twice with PBS, air-dried for approximately 1 hour, and lyzed with 1 ml of 0.1% SDS by pipetting, and then 300 µl of the lysate was obtained to detect radioactivity using a liquid scintillation counter (Perkin Elmer, USA).

Figure 2:
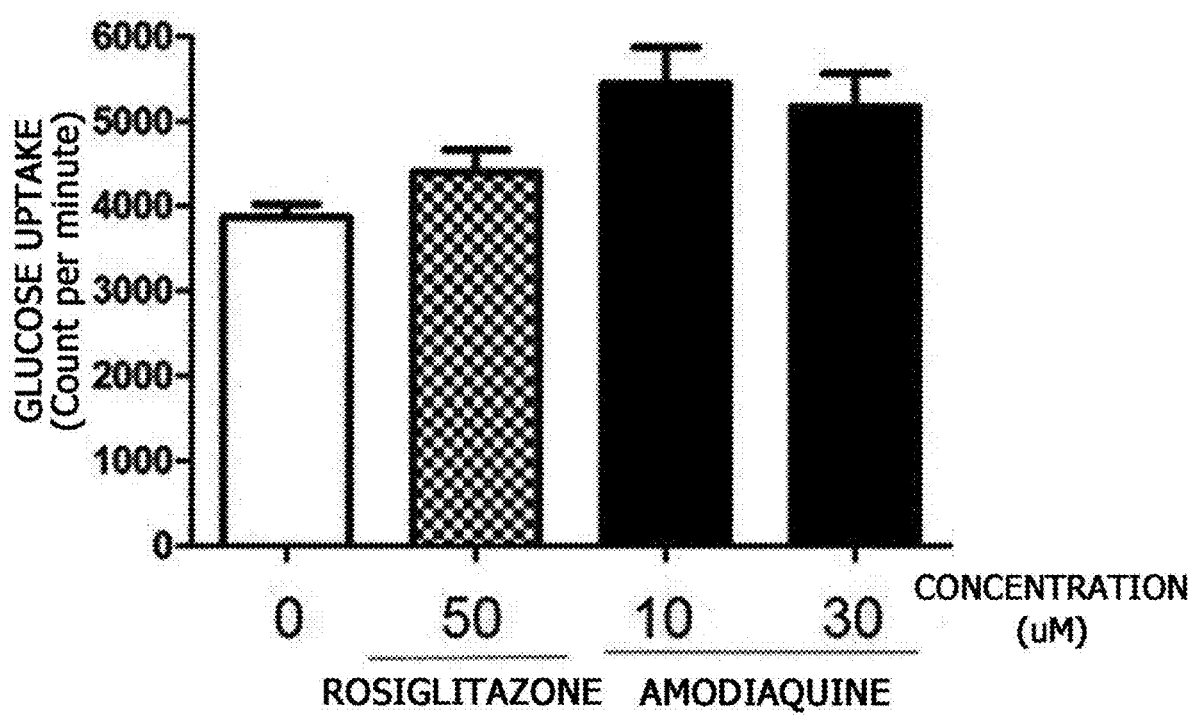
FIG. 2 is a graph showing measurement results of the uptake of a glucose derivative when a C2C12 myotube cell line, which relates to mouse-derived muscle cells, was treated with amodiaquine for 24 hours.

As a result, as illustrated in FIG. 2, it was confirmed that the glucose uptake in the group treated with amodiaquine was further increased as compared to that in the group treated with rosiglitazone, which was a positive control.

Thus, from the above-described results, it can be seen that amodiaquine has an effect of promoting glucose uptake into muscle cells by increasing the activity of PPAR-γ, which is a representative target protein of a diabetes therapeutic agent in cells.

Example 3. Measurement of Effects of Amodiaquine on Lowering and Regulating Blood Glucose in Mice 3-1. Administration of Amodiaquine and Negative Control 5-week-old KKAy purchased from Clea Japan was preliminarily raised for one week and then divided into two groups (5 individuals per group).

The first group was administered PBS and set as a negative control, and the second group was orally administered amodiaquine at a concentration of 18 mg/kg daily for 6 weeks.

3-2. Measurement of Fasting Blood Glucose-Lowering Effect and Blood Glucose-Regulating Effect in Mice For 6-week-long measurement of fasting blood glucose, whole blood was collected from the caudal vein on weeks 1, 2, 5, and 6 after 12-hour fasting. A blood glucose strip (Green Cross, Gyeonggi-do, Korea) was used to measure blood glucose. For the experimental results, significance of the experimental group and the control was verified using a t-test, and the groups showed statistically significant differences (*$p<0.05$ and **$p<0.005$). In addition, to identify the blood glucose regulation effect, 2 g/kg of glucose was intraperitoneally injected into control and experimental group animals after 16-hour fasting, and a blood glucose concentration was measured every 30 minutes for 2 hours. For measurement of the blood glucose concentration, an intraperitoneal glucose tolerance test (IPGTT) was used. For the experimental results, significance of the experimental group and the control was verified using an independent group t-test, and the groups showed statistically significant differences (*$p<0.05$ and **$p<0.005$).

Figure 3A:
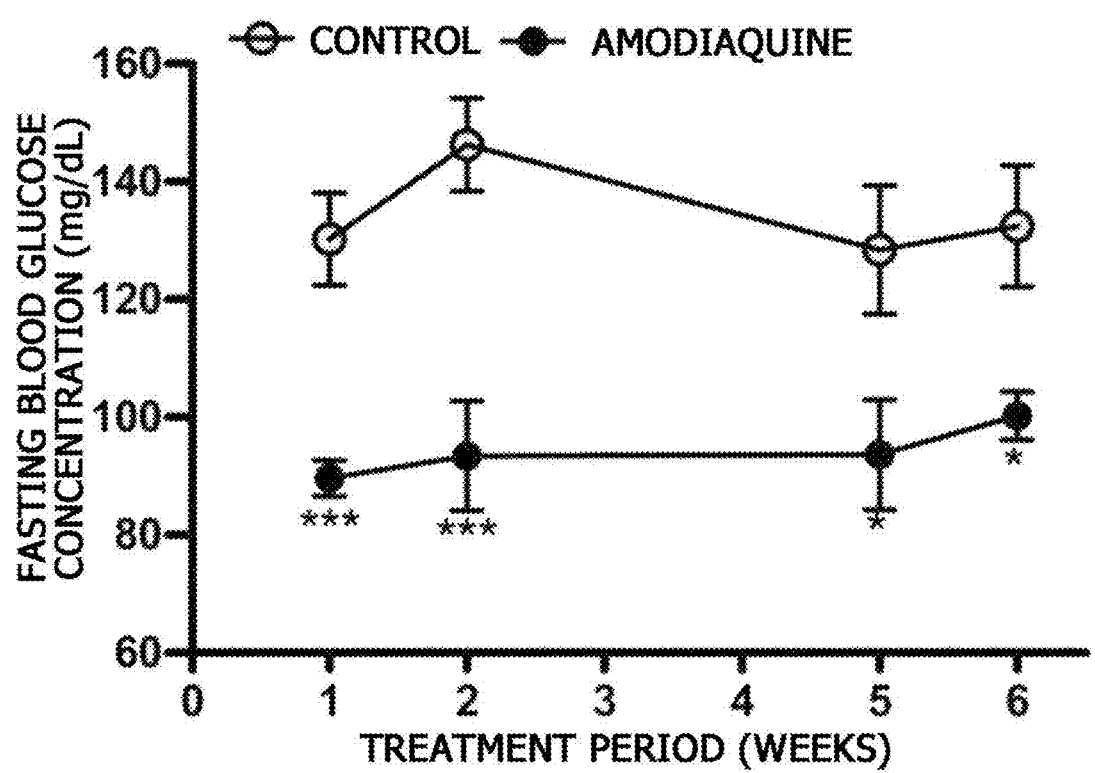
FIG. 3A is a graph showing an effect of amodiaquine uptake on a fasting blood glucose concentration of mice.
Figure 3B:
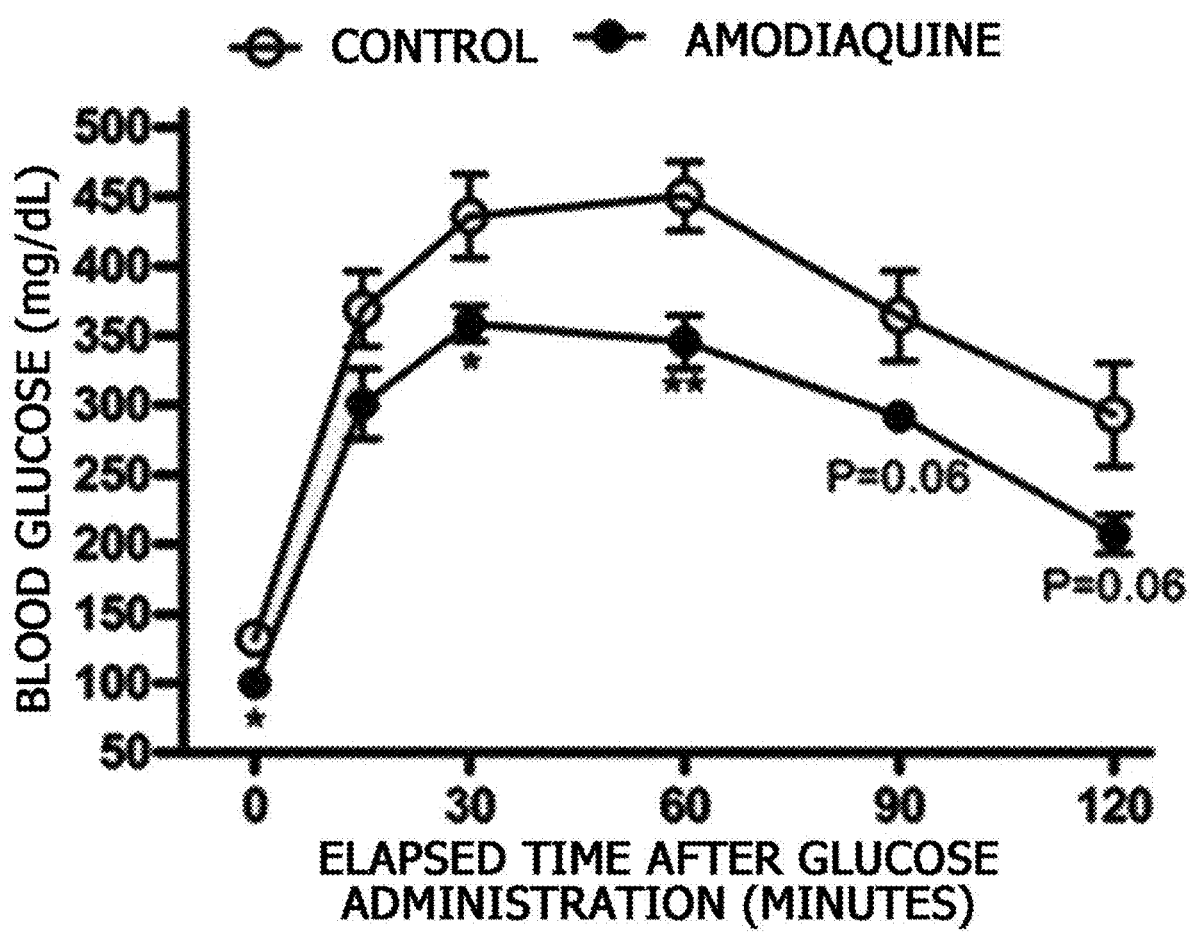
FIG. 3B is a graph showing results of an intraperitoneal glucose tolerance test (IPGTT) showing an effect of amodiaquine uptake on a change in blood glucose over time after glucose was administered to mice.

As a result, as illustrated in FIG. 3A, it was confirmed that fasting blood glucose was significantly decreased in the mice administered amodiaquine as compared to that of the control. In addition, as illustrated in FIG. 3B, it was confirmed that the blood glucose was rapidly reduced in the amodiaquine-administered group compared to the control, 2 hours after glucose administration. In particular, while the control had a fasting blood glucose concentration of 132.4 mg/dl, the amodiaquine-administered group had a fasting blood glucose concentration of 100.2 mg/dl, and 2 hours after glucose loading, the control had a blood glucose concentration of 293.2 mg/dl, while the amodiaquine-administered group had a blood glucose concentration of 207 mg/dl.

Accordingly, since amodiaquine has an excellent effect of reducing a blood glucose concentration, it can be seen that a pharmaceutical composition including amodiaquine as an active ingredient can be effectively used in preventing or treating diabetes, and since amodiaquine has an effect of reducing fasting blood glucose, it can be seen that a pharmaceutical composition including amodiaquine as an active ingredient can be effectively used as an agent for preventing or treating insulin-resistant type 2 diabetes.

Example 4. Effect of Amodiaquine on Glycated Hemoglobin (HbA1C) Content

Some of the glucose distributed in blood is tightly bound to red blood cells, which is called glycated hemoglobin (HbA1C). To investigate blood glucose regulation, not only a blood glucose level but also a glycated hemoglobin level is examined. This is because a 1% decrease in glycated hemoglobin leads to a 20% or more decrease in complications due to diabetes. In the present example, glycated hemoglobin contents of mice due to amodiaquine intake were examined.

4-1. Administration of Amodiaquine and Negative Control

To measure the glycated hemoglobin of mice due to amodiaquine, 5-week-old KKAy mice purchased from Clea Japan were preliminarily raised for 1 week, and then divided into 2 groups each including 5 individuals. As in Example 3, the first group of experimental animals was administered PBS and set as a control, and the second group was orally administered amodiaquine at a concentration of 18 mg/kg using a 1 ml syringe daily for 6 weeks.

4-2. Measurement of Glycated Hemoglobin in Mice

To measure an effect of amodiaquine on reducing glycated hemoglobin, whole blood was collected from the caudal vein of the mice of the control and the experimental group and injected into an easy A1c cartridge, and then measurement was performed using an easy A1c analyzer (Asan Pharmaceutical Co., Ltd., Seoul, Korea). For the experimental results, significance of the experimental group and the control was verified using an independent group t-test, and the groups showed a statistically significant difference (**$p<0.005$).

Figure 4:
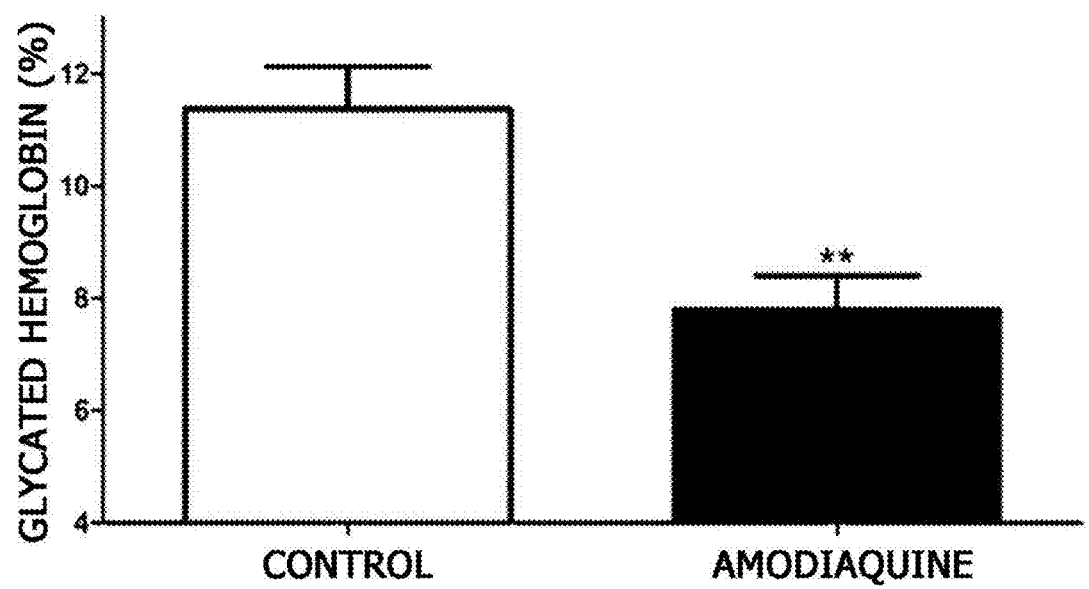
FIG. 4 is a graph showing an effect of amodiaquine uptake on glycated hemoglobin levels of mice.

As a result, as illustrated in FIG. 4, it was confirmed that glycated hemoglobin production was inhibited to approximately 69% in the amodiaquine-administered mice, as compared to that of the control mice.

Accordingly, it can be seen that amodiaquine has an effect of reducing glycated hemoglobin.

Example 5. Measurement of Decrease in Body Weight by Amodiaquine 5-1. Design of Experimental Animals and Compositions of Experimental Diets To measure a decrease in body weight of mice by amodiaquine, 7-week-old male C57BL/6 mice (Charles River Laboratories, Tokyo, Japan) were purchased and raised under certain conditions (temperature: 22±2° C., relative humidity: 55±10%, and light/dark cycle: 12 hours). The mice were grouped into 7 individuals per group, freely fed water and diets in a cage, and then acclimated for 1 week before an experiment.

After acclimatization, the mice were divided into 7 groups, and fed diets with administration of amodiaquine and positive controls (WY-14,643 and rosiglitazone) for the durations shown in Table 1 below.

TABLE 1

| Group | Type of diet | Amodiaquine (mg/kg) | WY-14,643 (mg/kg) | Rosiglitazone (mg/kg) | Duration |
|---|---|---|---|---|---|
| Normal control | LFD | — | — | — | Substance administration for 14 weeks |
| High fat control | HFD | — | — | — | |
| Positive control (for prevention) | HFD | — | 50 | — | |
| Amodiaquine group | HFD | 20 | — | — | |

TABLE 1-continued

| Group | Type of diet | Amodiaquine (mg/kg) | WY-14,643 (mg/kg) | Rosiglitazone (mg/kg) | Duration |
|---|---|---|---|---|---|
| High fat control | HFD | — | — | — | Substance administration for 7 weeks after induced by HFD for 15 weeks |
| Positive control (for treatment) | HFD | — | — | 50 | |
| Amodiaquine group | HFD | 20 | — | — | |

LFD (10% kcal as fat; D12450B, Research Diets Inc.)
HFD (60% kcal as fat; D12492, Research Diets Inc.)

5-2. Measurement of Change in Body Weight in Mice

For examination of a change in body weight, body weights of normal diet-fed mice, high fat-induced obesity mice fed a high fat diet, and high fat-induced obesity mice fed a high fat diet with amodiaquine and positive controls (WY-14,643 and rosiglitazone) were measured using an electronic scale (Dragon 204/S, Mettler Toledo, USA) on the basis of 10 a.m. once a week for 21 weeks. An average body weight was calculated by dividing the sum of weights of 7 mice per group by the number of mice. For the experimental results, significance of the high fat-induced obesity control, the amodiaquine-administered group, and the positive controls (WY-14,643 and rosiglitazone) was verified using an independent group t-test, and the groups showed statistically significant differences (*P<0.05, P<0.005, and *P<0.0005).

Figure 5A:
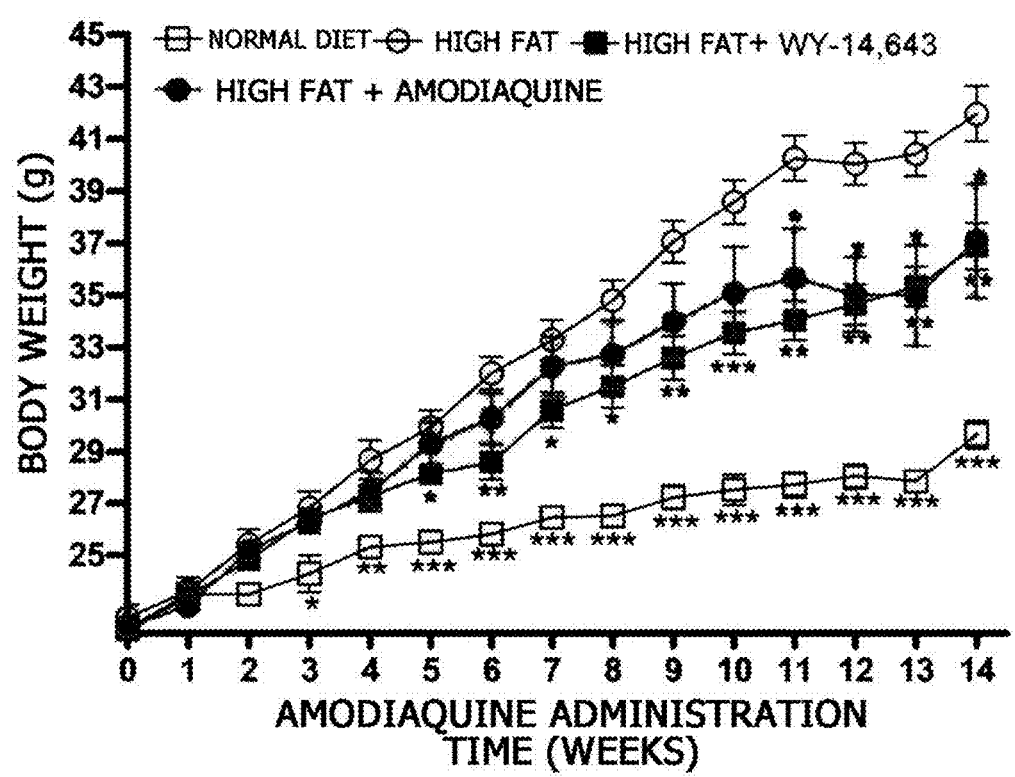
FIG. 5A is a graph showing an obesity inhibitory phenomenon of mice when high fat diet-induced obesity mice were fed a high fat diet with simultaneous administration of amodiaquine.

As a result of the experiment, as illustrated in FIG. 5A, it can be observed that the body weight of the high fat-induced obesity mice administered amodiaquine was significantly lower than that of the high fat-induced obesity mice, and was similar to that of the positive control (WY-14,643). A significant decrease in body weight was also observed in the case of FIG. 5C in which obesity was induced by a high fat diet, and then amodiaquine was administered, as compared to that of the high fat-induced obesity mice. In contrast, it was confirmed that the body weight of the positive control administered rosiglitazone, which is a PPAR-γ agonist, was similar to or higher than that of the high fat-induced obesity mice.

5-3. Measurement of Feed Intake of High Fat-Induced Obesity Mice

Figure 5B:
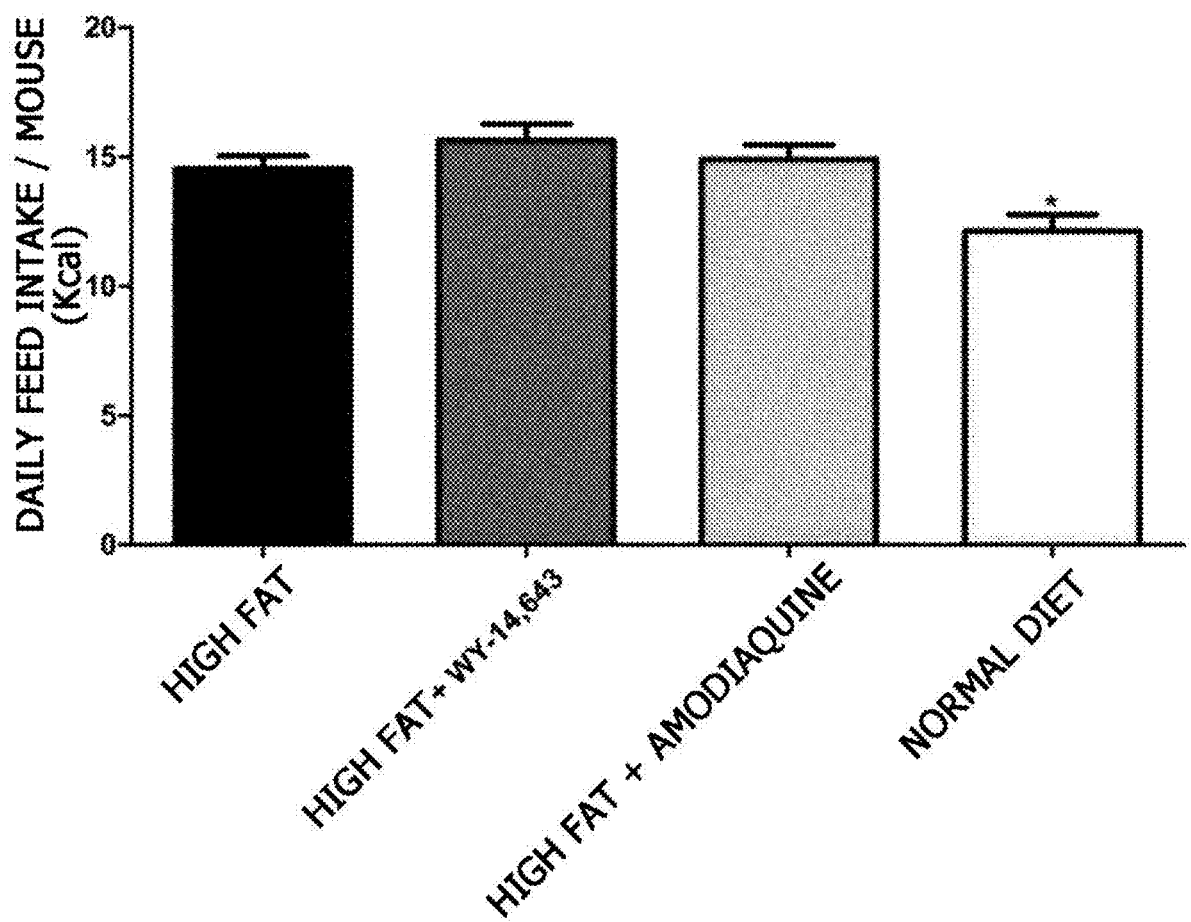
FIG. 5B is a graph showing the daily average feed uptake of mice.
Figure 5C:
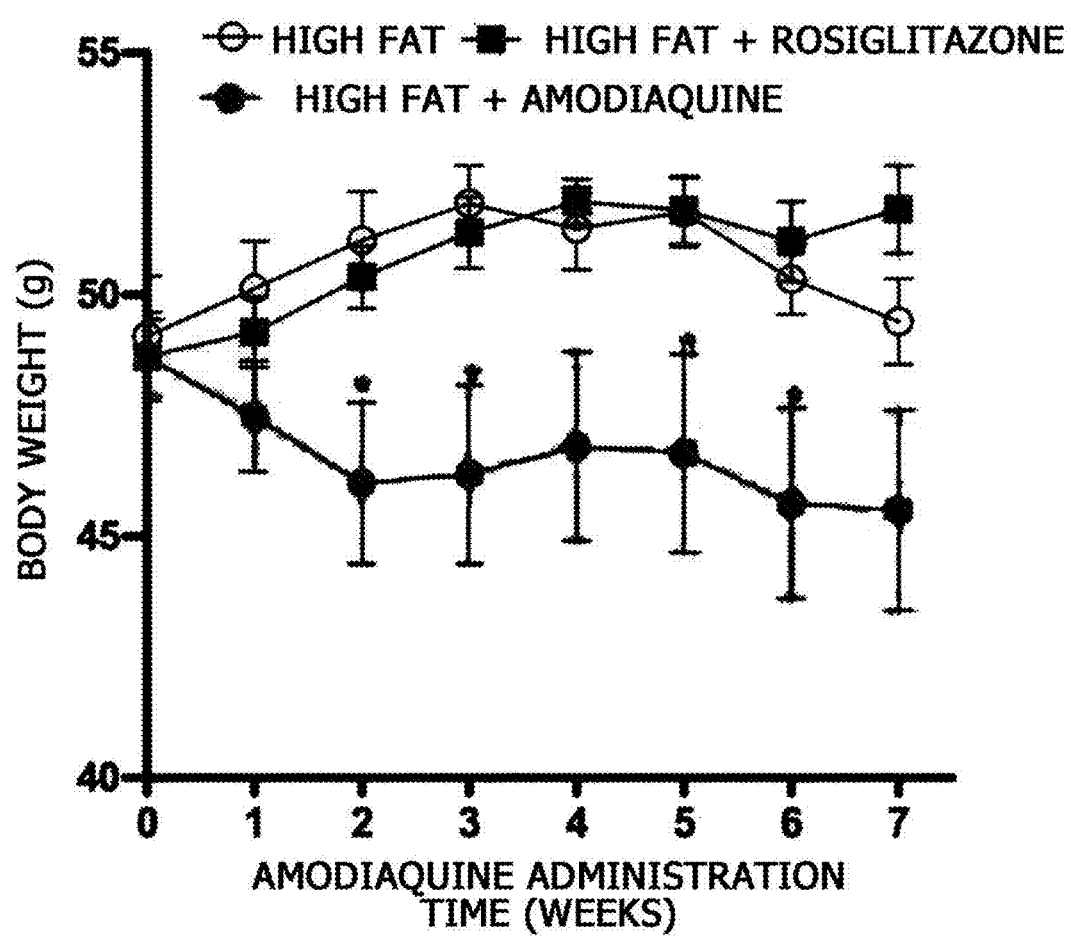
FIG. 5C is a graph showing an obesity-treated phenomenon occurring by administering amodiaquine to high fat diet-induced obesity mice, wherein the obesity was induced for a long-term (20 weeks) period.
Figure 5D:
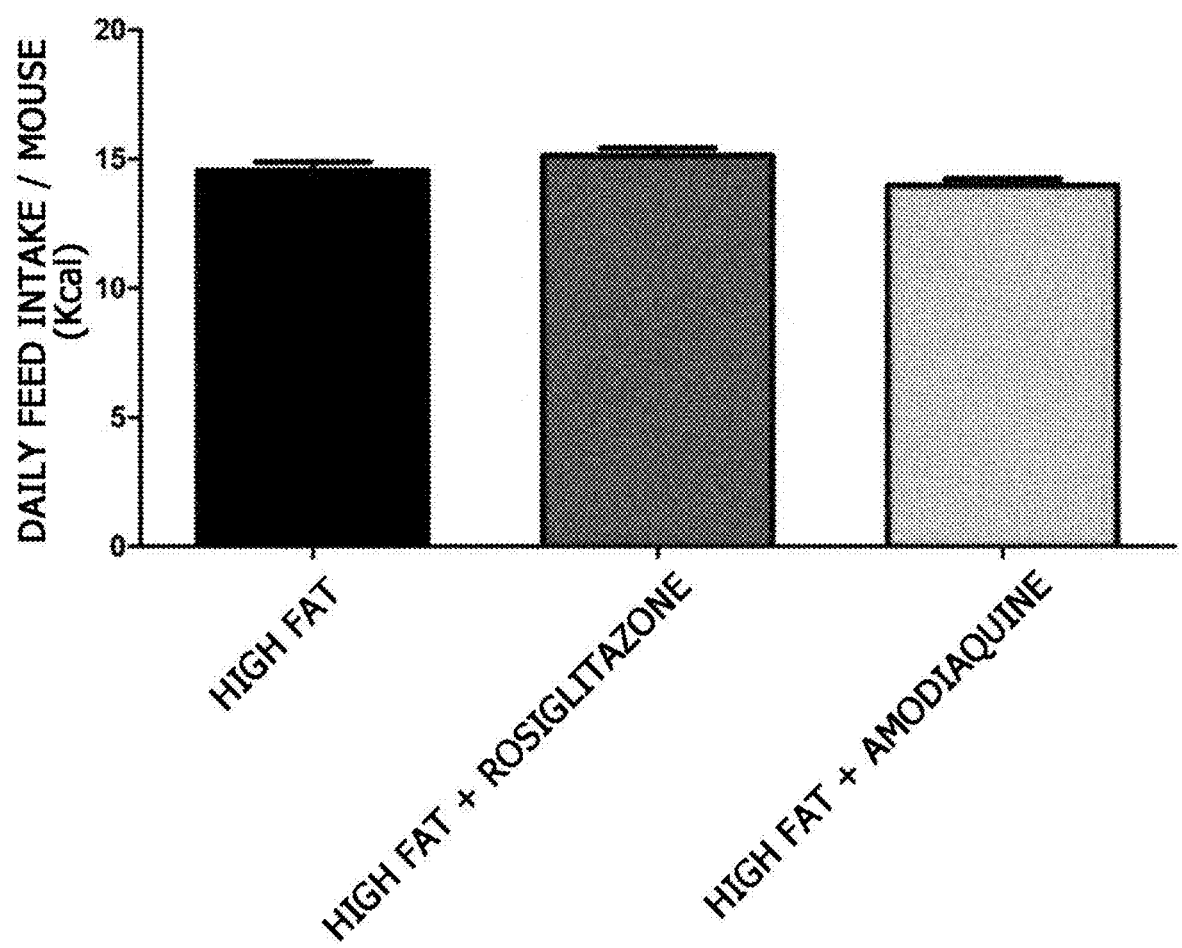
FIG. 5D is a graph showing a daily average feed uptake of each mouse.

Feed intakes were measured for mice fed a normal diet, high fat-induced obesity mice fed a high fat diet, and high fat-induced obesity mice fed a high fat diet and administered amodiaquine and the positive controls (WY-14,643 and rosiglitazone) on the basis of 11 a.m daily. An average feed intake was obtained by dividing the feed intakes of 7 mice per group by 7. Every feed intake was converted into kcal. As a result of the experiment, as illustrated in FIGS. 5B and 5D, it was observed that there was no difference between the feed intake of the high fat-induced obesity mice administered amodiaquine and the positive controls (WY-14,643 and rosiglitazone) and the feed intake of the high fat-induced obesity mice.

The results show that amodiaquine has an effect of reducing the body weight of mice regardless of feed intake, and thus may be used as an anti-obesity medicine.

Example 6. Measurement of Effect of Amodiaquine on Heat Production

Adipose cells are divided into white adipose cells acting on lipid accumulation, and brown adipose cells acting on heat production although in a very small amount. The brown adipose cells have a meal-inducible heat production action to warm a body after a meal, and when a temperature is reduced, activity is increased and the body temperature is maintained due to heat production. Due to poor functioning of the brown adipose cells, when ob/ob mice, which are a hereditary obesity animal as an obesity test model, were exposed to a low temperature of 4° C., the body temperature thereof was gradually decreased and they eventually died after approximately 4 hours. When the brown adipose cells malfunction, little energy is lost as heat at a normal temperature, and thus obesity is highly likely to occur due to accumulated excessive energy. Accordingly, in the present example, the heat production capability of the high fat-induced obesity mice due to amodiaquine administration was examined.

6-1. Measurement of Heat Production Capability of High Fat-Induced Obesity Mice

To measure the heat production capability of mice fed a high fat diet for 14 weeks among the experimental animals designed in Example 5, a 4° C. cold test was performed (Spiegelman B. M. et al., Cell 92: 829-839, 1998). Hereinafter, the measurement method will be described in detail. A body temperature of mice in the high fat-induced obesity mouse group was measured before being exposed to 4° C., and recorded as an experiment start measurement temperature, and then the mice were exposed in a 4° C. room for up to 6 hours, followed by measurement of body temperature every hour. The body temperature was measured using a rectal thermometer for a mouse (Testo 925, Germany). A heat production measurement value indicated a temperature measured every hour. For the experimental results, significance of the experimental group and the control was verified using an independent group t-test, and the groups showed statistically significant differences (*p<0.05 and ***p<0.0005).

Figure 6:
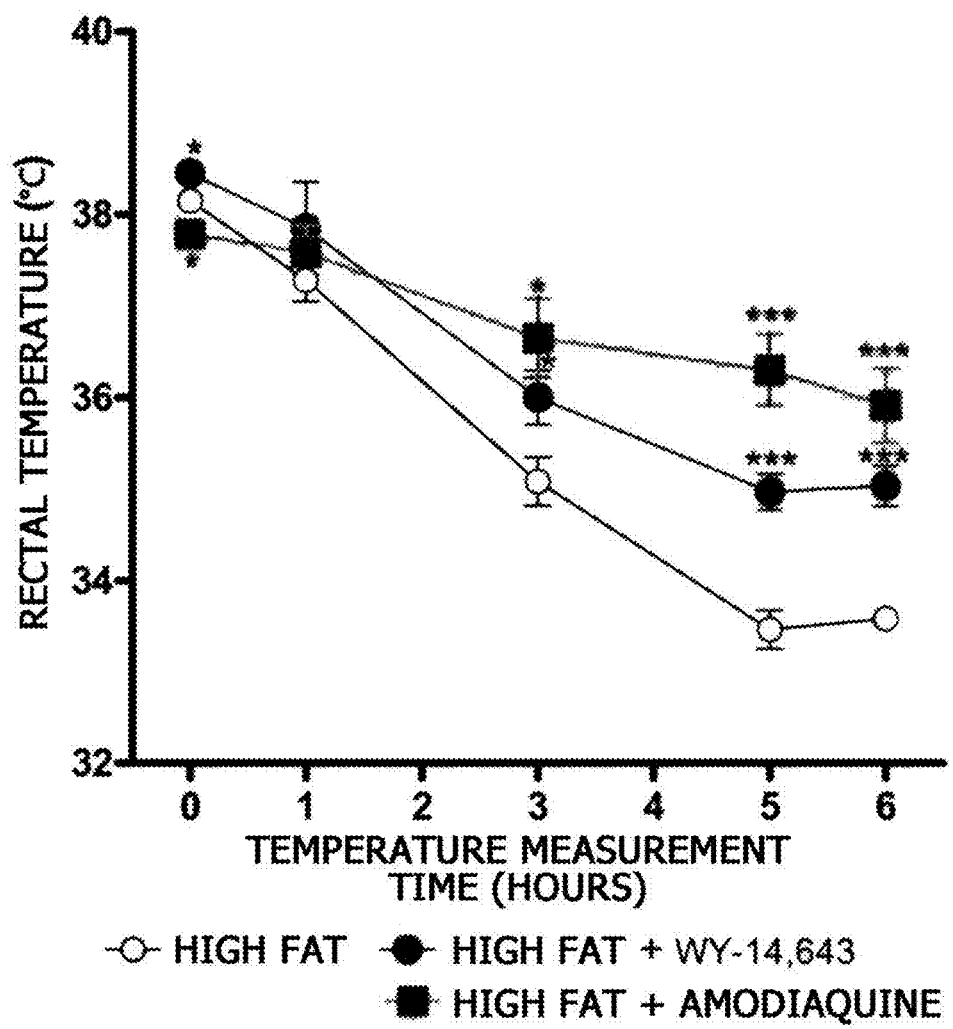
FIG. 6 is a graph showing heat production of high fat diet-induced obesity mice when exposed to low temperatures, according to amodiaquine uptake.

As a result of the experiment, as illustrated in FIG. 6, it was confirmed that the high fat-induced obesity mice administered amodiaquine exhibited a smaller decrease in body temperature than that of the high fat-induced obesity mice and accordingly, exhibited an excellent heat production effect.

From the above-described results, it can be seen that amodiaquine according to the present invention has an effect of reducing the possibility of being obese since a large amount of energy is produced as heat by increasing the heat production activity of high fat-induced obesity mice.

Example 7. Measurement of Effect of Amodiaquine on Blood Glucose Regulation in Mice In the present example, to measure a blood glucose regulation effect in the experimental animals designed in Example 5, an oral glucose tolerance test and an intraperitoneal insulin tolerance test were conducted.

7-1. Oral Glucose Tolerance Test Measurement for Mice

After fasting for 16 hours, 2 g/kg of glucose was orally administered to each of the control and experimental group animals, and a blood glucose concentration was measured every 30 minutes for 2 hours. For measurement of the blood glucose concentration, an oral glucose tolerance test (OGTT) was used. For the experimental results, significance of the high fat-induced obesity mouse control, the high fat-induced obesity mice administered amodiaquine, the high fat-induced obesity mice administered the positive control (WY-14,643), and mice fed a normal feed was verified using an independent group t-test, and the groups showed statistically significant differences ($p<0.05$, $p<0.005$, and $*p<0.0005$).

Figure 7A:
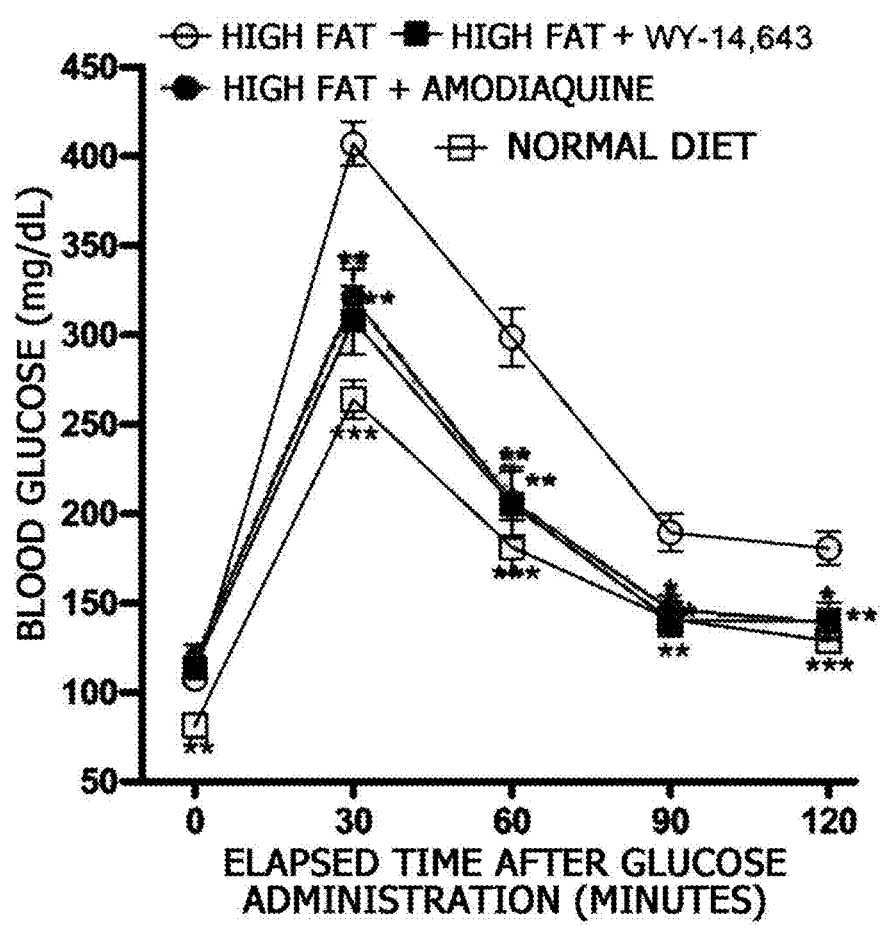
FIG. 7A is a graph showing results of an oral glucose tolerance test (OGTT) showing an effect of amodiaquine on a change in blood glucose over time after glucose is administered to mice fed a high fat diet and simultaneously administered amodiaquine.

As a result, as illustrated in FIG. 7A, it was confirmed that 2 hours after glucose administration, a rapid decrease in blood glucose was exhibited in the amodiaquine-administered group compared to in the high fat-induced obesity mouse control. In particular, 2 hours after glucose loading, the high fat-induced obesity mouse control exhibited a blood glucose concentration of 180.5 mg/dl, but the amodiaquine-administered group exhibited a blood glucose concentration of 139.1 mg/dl.

Accordingly, it can be seen that since amodiaquine exhibits an excellent effect of reducing a blood glucose concentration, a pharmaceutical composition including amodiaquine as an active ingredient may be effectively used as an agent for preventing and treating insulin-resistant type 2 diabetes.

7-2. Intraperitoneal Insulin Tolerance Test Measurement for Mice

After fasting for 16 hours, 0.5 U/kg of insulin was intraperitoneally administered to each of the control and experimental group animals, and a blood glucose concentration was measured every 30 minutes for 2 hours. For measurement of the blood glucose concentration, an intraperitoneal insulin tolerance test (IPITT) was used. For the experimental results, significance of the high fat-induced obesity mouse control, the high fat-induced obesity mice administered amodiaquine, the high fat-induced obesity mice administered the positive controls (WY-14,643 and rosiglitazone), and mice fed a normal feed was verified using an independent group t-test, and the groups showed statistically significant differences ($*p<0.05$, $p<0.005$, and $*p<0.0005$).

Figure 7B:
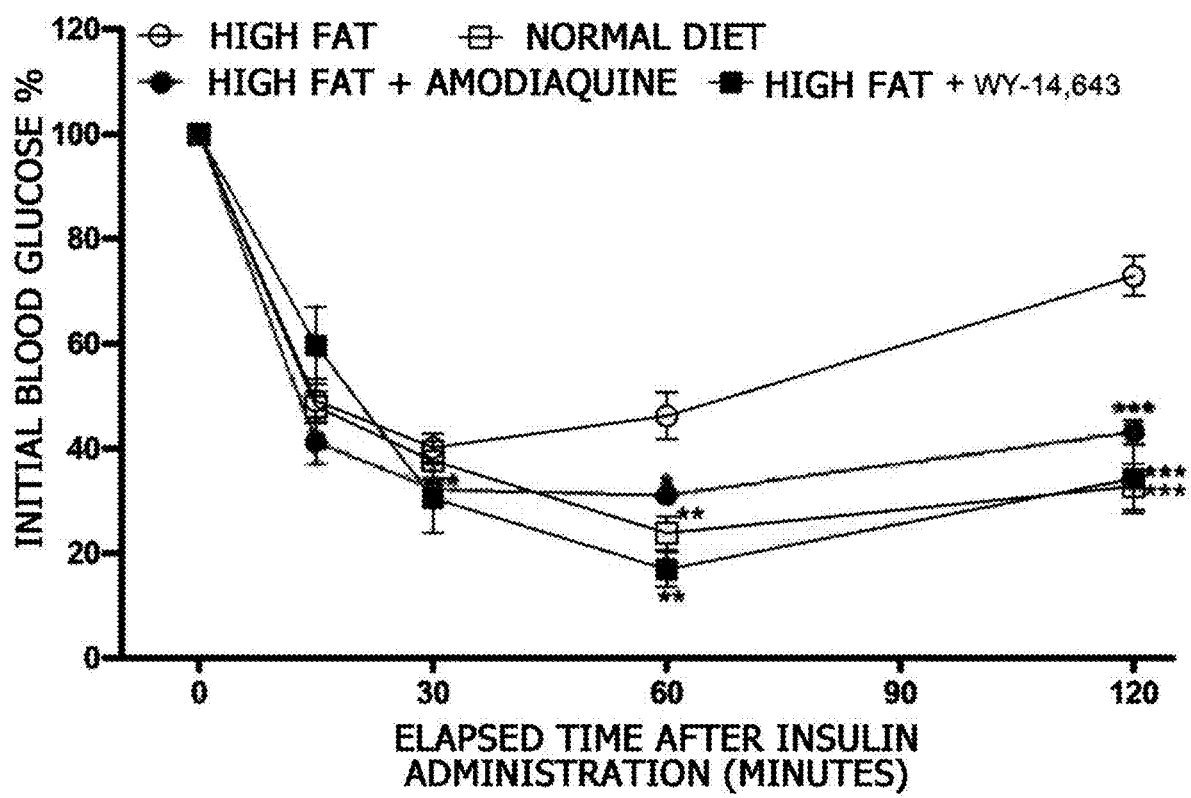
FIG. 7B is a graph showing intraperitoneal insulin tolerance test (IPITT) results of confirming a change in blood glucose concentration over time after insulin was injected into mice fed a high fat diet and simultaneously administered amodiaquine.
Figure 7C:
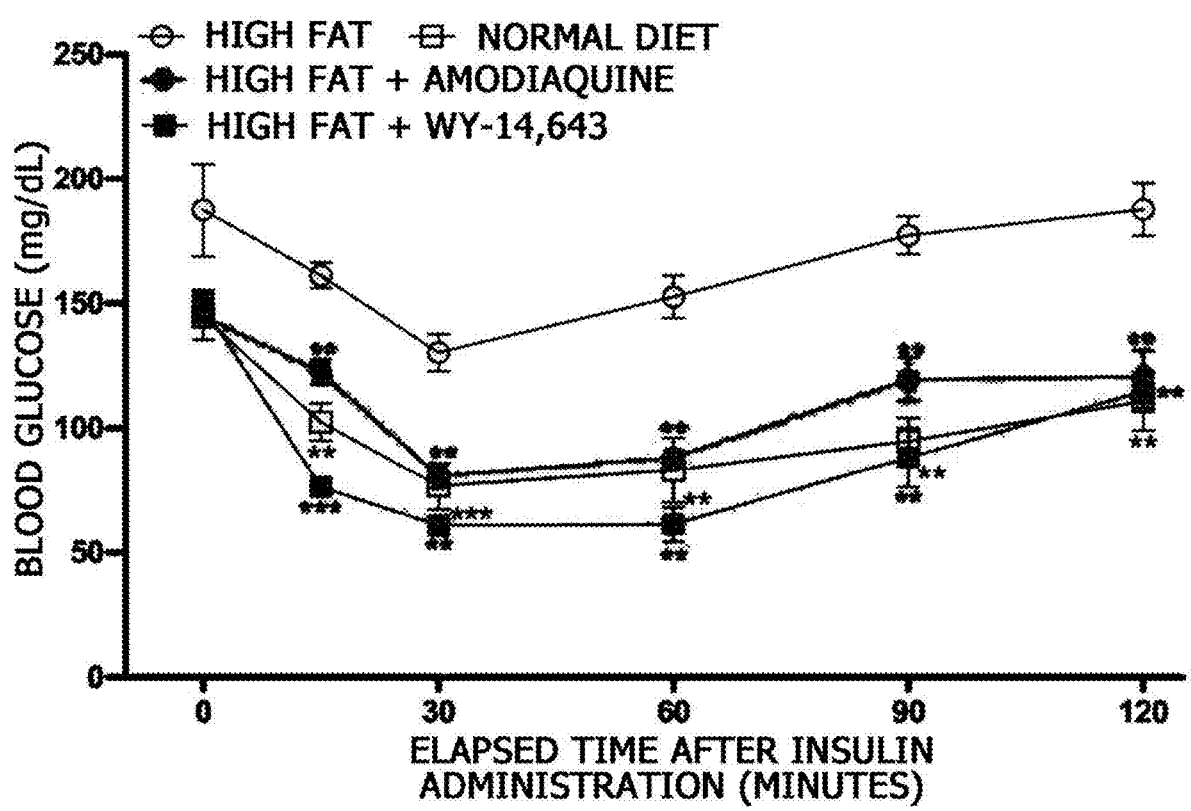
FIG. 7C is a graph showing IPITT results of confirming a change in blood glucose concentration over time after amodiaquine was administered to high fat diet-induced obesity mice, followed by insulin injection, wherein the obesity was induced for a long-term (20 weeks) period.

As illustrated in FIG. 7B, as a result of administering insulin to the high fat-induced obesity mouse control and the experimental group and measuring insulin resistance of each group, the blood glucose was at the lowest level in all groups at 30 minutes, and then gradually increased. In the high fat-induced obesity mouse control, a blood glucose concentration was increased to a fasting blood glucose concentration at 120 minutes, and in the normal diet-fed group, the positive control (WY-14,643), and the amodiaquine-administered group, a blood glucose concentration after 2 hours was maintained at a lower level than the fasting blood glucose concentration. In addition, as illustrated in FIG. 7C, insulin was administered to the insulin-resistant obesity mouse control induced by a high fat diet and the experimental groups, and initial blood glucose was expressed as a percentage (%). As a result of measuring insulin resistance, the insulin resistance was exhibited at the lowest level at 30 minutes in the high fat-induced obesity mouse mice and the amodiaquine-administered group, and then gradually increased. In the positive control (rosiglitazone) and the normal diet-fed group, the blood glucose concentration was exhibited at the lowest level at 60 minutes, and then gradually increased. In the high fat-induced obesity mouse control, the blood glucose concentration at 120 minutes was increased to approximately 70% of the initial blood glucose, and in the normal diet-fed group, the positive control (rosiglitazone), and the amodiaquine-administered group, the blood glucose concentration after 2 hours was maintained at approximately 40% to 45% of the initial blood glucose.

Accordingly, it can be seen that since the intake of amodiaquine increases insulin sensitivity, amodiaquine may be effectively used as an agent for preventing or treating insulin-resistant type 2 diabetes.

Example 8. Measurement of Effect of Amodiaquine on Preventing Fatty Liver

Fatty liver is caused by nutritional imbalances related to high calorie diets, high fat diets, and the intake of simple sugars, other than alcoholic fatty liver occurring due to an excessive intake of alcohol. In particular, the continuous intake of a high calorie diet or a high fat diet causes lipid metabolic disorders between lipogenesis and lipolysis in the liver, thus inducing fatty liver.

Thus, in the present example, the effect of amodiaquine treatment on fatty liver induction was examined.

8-1. Tissue Removal from High Fat-Induced Obesity Mouse Group

Among the experimental animals designed in Example 5, mice in the high fat-induced obesity mouse group fed a high fat diet for 14 weeks with drug administration and high fat-induced obesity mice fed a high fat diet for 7 weeks with drug administration after obesity was induced by a high fat diet for 15 weeks were sacrificed by cervical spine dislocation, fixed on a dissection stand, and subjected to abdominal dissection with a scalpel to extract the liver. The extracted liver tissue was fixed in a 10% formalin solution to prevent contractile deformation. After 24 hours, the fixed tissue was washed with running water, and then general tissue dehydration, clearing, and penetration were performed thereon using an automatic tissue processor (6460B, Sakura, Japan) for 14 hours, and manufacture of paraffin blocks and cooling were performed using an automated embedding device (Tissue-Tex, Japan). The manufactured paraffin blocks were continuously sliced to a thickness of 4 m to 5 m in a vertical direction of the tissue using a rotary microtome 2040 (Japan), and attached to slides after processing using a floating hot water tank and a slide warming table.

8-2. Observation of Effect of Amodiaquine on Preventing Fatty Liver

The thin tissue section was stained with hematoxylin, an excessively-stained portion was washed with running tap water, and then the resulting section was dipped in 1% HCl and a 70% A/C solution 3 times to 5 times to stain the nuclei blue. Subsequently, the section was sufficiently washed for approximately 5 minutes to 10 minutes, subjected to cytoplasmic counter staining to make the nuclei clear, and washed with running water for 15 seconds to remove an excessive eosin solution, followed by tissue dehydration and clearing. Each liver tissue was observed using an optical microscope (BX50, Olympus, Japan), and an image of tissue in each group was captured using a CCD camera (PM-C35DX, Olympus, Japan) included with the microscope.

Figure 8A:
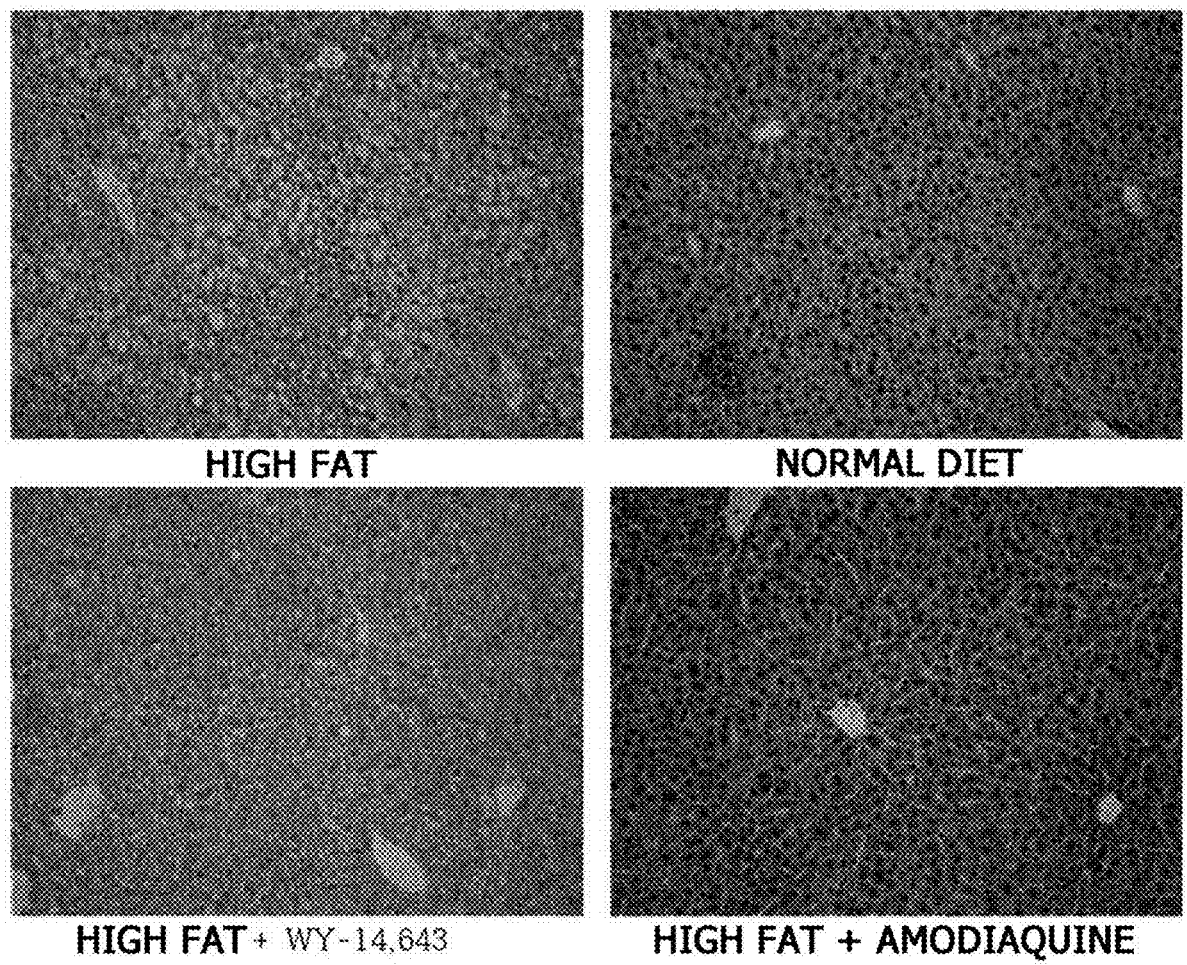
FIGS. 8A and 8B are graphs respectively showing histological changes in liver cells due to fat accumulation after the liver of an experimental animal raised with a high fat diet and amodiaquine for 14 weeks and the liver of an experimental animal raised with a high fat diet and amodiaquine for 22 weeks were stained with hematoxylin & eosin.
Figure 8B:
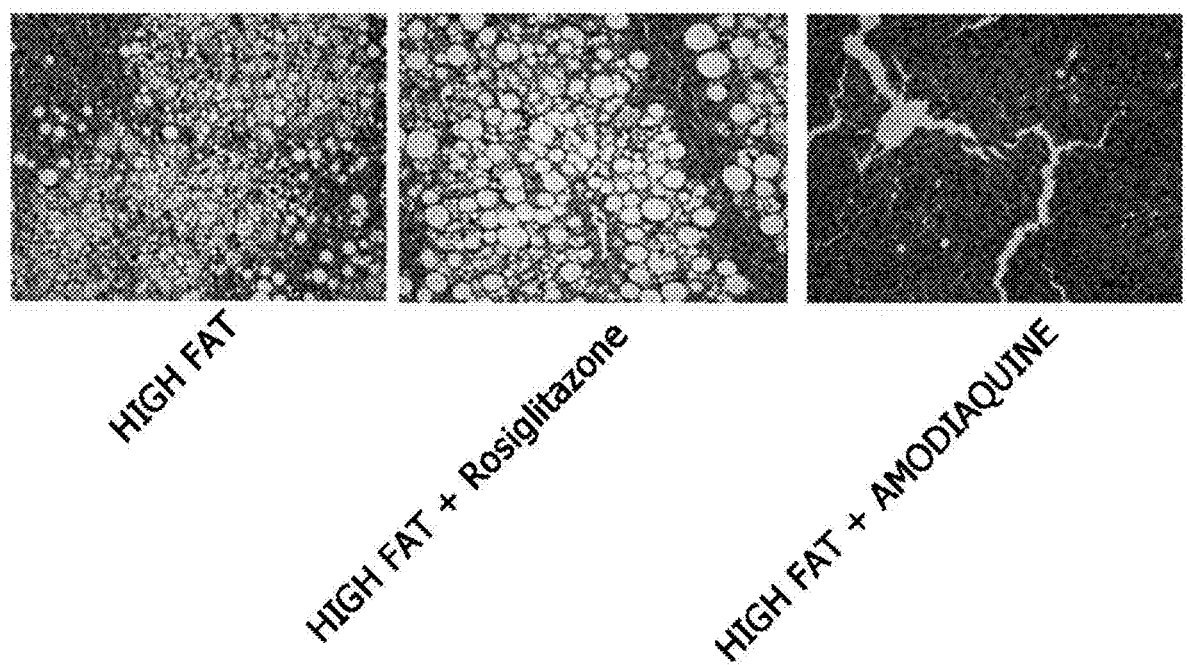

As a result of the experiment, as illustrated in FIGS. 8A and 8B, it was confirmed that while the liver of the high fat-induced obesity mice was full of fat, the liver of the high fat-induced obesity mice administered amodiaquine had almost the same appearance as that of normal mice.

Therefore, it can be seen from the above-described results that amodiaquine according to the present invention has an excellent effect of inhibiting fatty liver.

Example 9. Identification of Expression of Target Gene According to PPAR-α Activation in Liver, Muscle, and Adipose Tissues by Amodiaquine Administration PPAR-α is known to reduce the synthesis of fatty acids by inducing the expression of acryl-CoA oxidase (ACOX), carnitine palmitoyl transferase-1 (CPT-1), and medium chain acyl-CoA dehydrogenase (mCAD), which are genes of enzymes involved in the fatty acid oxidation metabolic pathway. Thus, when expression levels of the ACOX, CPT-1, and mCAD genes are measured, fatty acid oxidation efficacy may be identified. Therefore, in the present example, the effect of amodiaquine administration on expression levels of the ACOX, CPT-1, and mCAD genes in liver, muscle, and adipose tissues was examined.

Among the experimental animals designed in Example 5, mice of the high fat-induced obesity mouse groups fed a high fat diet for 14 weeks were sacrificed by cervical spine dislocation, fixed on a dissection stand, and then subjected to dissection with a scalpel to extract liver, muscle, and adipose tissues, and primer base sequences of (β-actin, ACOX, CPT-1, and mCAD are as follows:

```
β-actin forward:
                                    (SEQ ID NO: 2)
5'-GGG AAG GTG ACA GCA TTG-3'

Reverse:
                                    (SEQ ID NO: 3)
5'-ATG AAG TAT TAA GGC GGA AGA TT-3'

ACOX forward:
                                    (SEQ ID NO: 4)
5'-ACA CTA ACA TAT CAA CAA GAG GAG-3'

Reverse:
                                    (SEQ ID NO: 5)
5'-CAT TGC CAG GAA GAC CAG-3'

CPT-1 forward:
                                    (SEQ ID NO: 6)
5'-CCA CCT CTT CTG CCT CTA T-3'

Reverse:
                                    (SEQ ID NO: 7)
5'-TTC TCA AAG TCA AAC AGT TCC A-3 mCAD forward:
                                    (SEQ ID NO: 8)
5'-CCG AAG AGT TGG CGT ATG-3'

Reverse:
                                    (SEQ ID NO: 9)
5'-AGC AAG AAT CAC AGG CAT T-3'.
```

After each tissue was disrupted using a grinding instrument, RNA was extracted using TRIzol, and cDNA was synthesized using reverse transcription polymerase chain reaction (RT PCR). As a control, β-actin was used, and to determine the expression levels of the ACOX, CPT-1, and mCAD genes, which are target genes according to PPAR-α activation and involved in fatty acid degradation, real-time polymerase chain reaction (RT PCR) was performed using primers for each gene (at 95° C. for 3 minutes, 39 cycles of 95° C. for 10 seconds, 60° C. for 10 seconds, and 72° C. for 30 seconds, at 95° C. for 10 seconds, and at 65° C. for 5 seconds). The ACOX, CPT-1, and mCAD genes were calibrated with β-actin, thereby obtaining resultant values. For the experimental results, significance of the high fat-induced obesity mouse control, the high fat-induced obesity mice administered amodiaquine, and the high fat-induced obesity mice administered the positive control (WY-14,643) was verified using an independent group t-test, and the groups showed statistically significant differences (*$p<0.05$, $p<0.005$, and *$p<0.0005$).

Figure 9A:
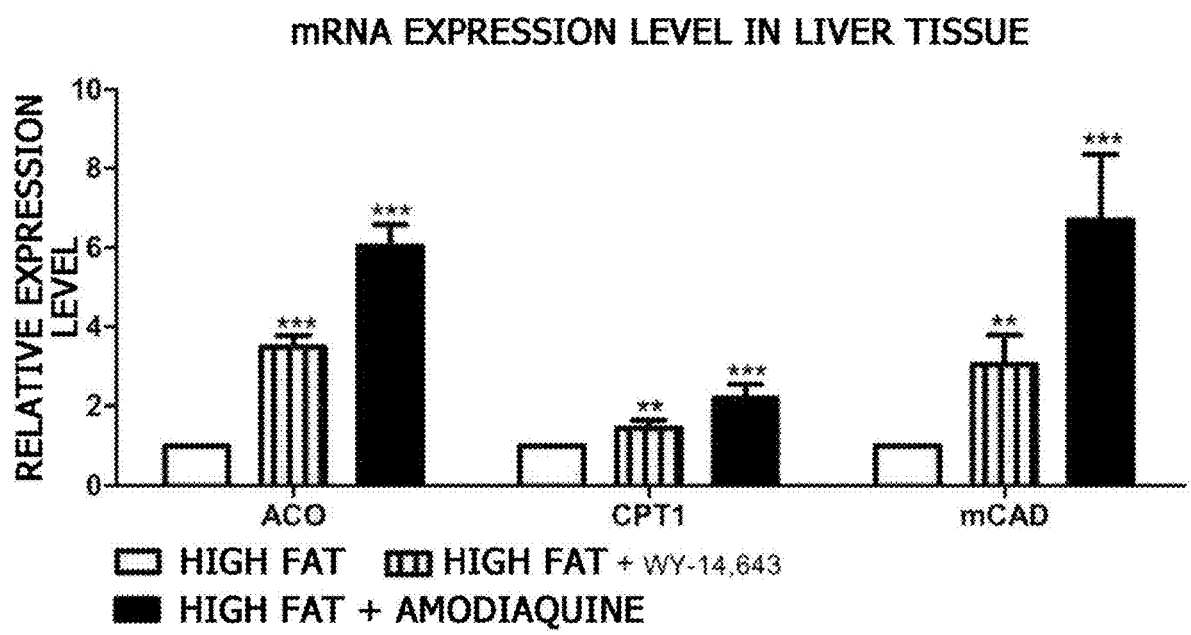
FIGS. 9A, 9B, and 9C are graphs respectively showing results of measuring the expression of fatty acid oxidation-related genes in liver tissues, muscle tissues, and adipose tissues of high fat diet-induced obesity mice administered amodiaquine.
Figure 9B:
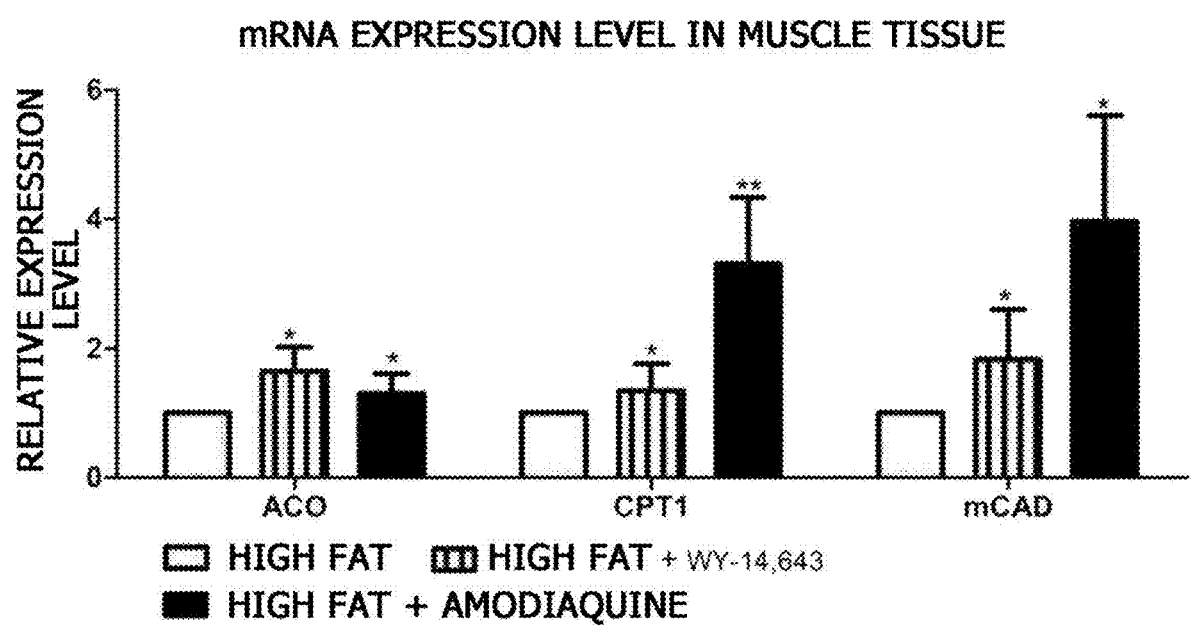
Figure 9C:
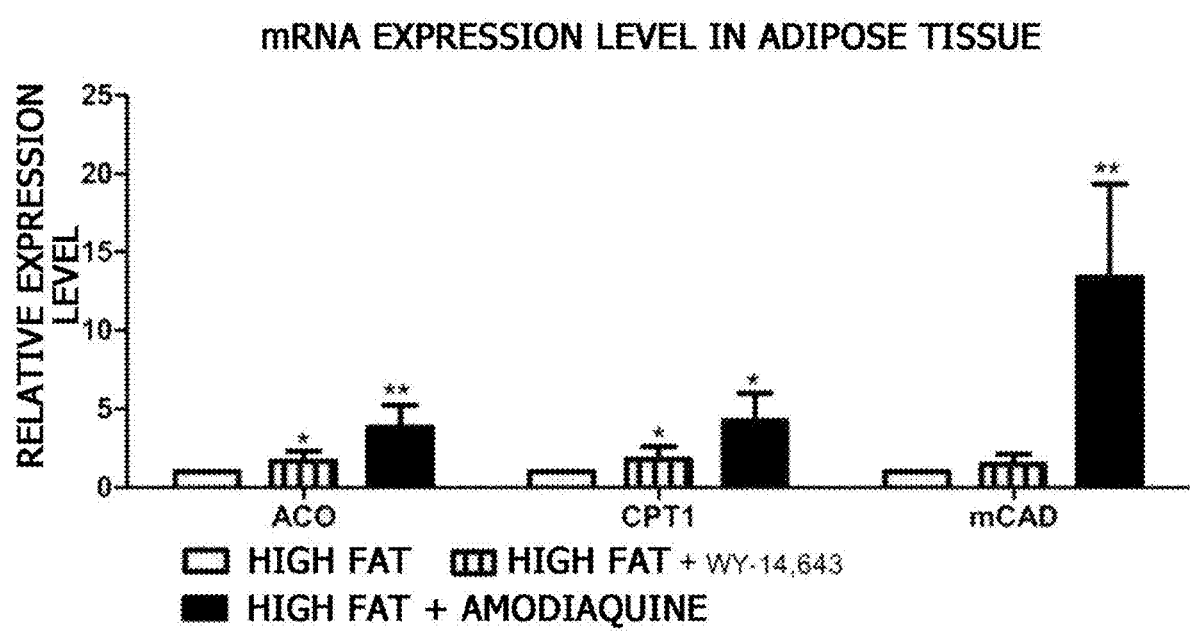

As a result, as illustrated in FIGS. 9A, 9B, and 9C, it was confirmed that an approximate 215-fold or more increase in expression amounts of the genes was exhibited in the experimental group administered amodiaquine, as compared to the control.

Therefore, from the result that amodiaquine treatment increased the expression of the ACOX, CPT-1, and mCAD genes, which are target genes according to PPAR-α activation and involved in fatty acid degradation, in each tissue, it can be seen that amodiaquine can regulate the expression of target genes of PPAR-α by activating PPAR-α, and it was determined that fat accumulation could be inhibited by promoting fatty acid oxidation.

Example 10. Identification of Expression of Target Genes by Anti-Inflammatory Response in Adipose Tissue According to Amodiaquine Administration Adipocytes differentiate from mesenchymal stem cells and preadipocytes, and bring about changes in a lipid metabolic function, a saccharometabolic function, and even the secretion of adipocytokines. TNFα, MCP-1, iNOS, and the like increased in obesity patients promote adipose differentiation due to inflammation expression of adipocytes, and increase the morbidity rates of other adult diseases. TNF-α is a cellular secretory substance that plays an important role in inflammatory responses, and MCP-1, which is an inflammatory chemokine, is known to be secreted from adipocytes and have an effect on obesity, insulin resistance, and arteriosclerosis. In addition, iNOS is an inflammatory precursor which is known to promote inflammatory responses.

Accordingly, when expression levels of the TNFα, MCP-1, and iNOS genes are measured, anti-inflammatory efficacy may be identified. Therefore, in the present example, the effect of amodiaquine administration on the expression levels of the TNFα, MCP-1, and iNOS genes in adipose tissue was examined.

Among the experimental animals designed in Example 5, mice of the high fat-induced obesity mouse groups fed a high fat diet for 14 weeks were sacrificed by cervical spine dislocation, fixed on a dissection stand, and then subjected to dissection with a scalpel to extract adipose tissue, and primer base sequences of (β-actin, TNFα, MCP-1, and iNOS are as follows:

```
β-actin forward:
                                    (SEQ ID NO: 2)
5'-GGG AAG GTG ACA GCA TTG-3'

Reverse:
                                    (SEQ ID NO: 3)
5'-ATG AAG TAT TAA GGC GGA AGA TT-3'

TNFα forward:
                                    (SEQ ID NO: 10)
5'-ATG AGA AGT TCC CAA ATG GC-3'
```

```
Reverse:
                                        (SEQ ID NO: 11)
5'-TTT GAG AAG ATG ATC TGA GTG TGA G-3'

MCP-1 forward:
                                        (SEQ ID NO: 12)
5'-AAT GAG TAG GCT GGA GAG-3'

Reverse:
                                        (SEQ ID NO: 13)
5'-TCT CTT GAG CTT GGT GAC-3 iNOS forward:
                                        (SEQ ID NO: 14)
5'-GCT TCT GGC ACT GAG TAA-3'

Reverse:
                                        (SEQ ID NO: 15)
5'-GGA GGA GAG GAG AGA GAT-3.
```

After the adipose tissue was disrupted using a grinding instrument, RNA was extracted using TRIzol, and cDNA was synthesized using reverse transcription polymerase chain reaction (RT PCR). As a control, β-actin was used, and to determine the expression levels of the TNFα, MCP-1, and iNOS genes, which are involved in inflammatory responses, real-time polymerase chain reaction (RT PCR) was performed using primers for each gene (at 95° C. for 3 minutes, 39 cycles of 95° C. for 10 seconds, 60° C. for 10 seconds, and 72° C. for 30 seconds, at 95° C. for 10 seconds, and at 65° C. for 5 seconds). The TNFα, MCP-1, and iNOS genes were calibrated with β-actin, thereby obtaining resultant values. For the experimental results, significance of the high fat-induced obesity mouse control, the high fat-induced obesity mice administered amodiaquine, and the high fat-induced obesity mice administered the positive control (WY-14,643) was verified using an independent group t-test, and the groups showed statistically significant differences ($*p<0.05$ and $**p<0.005$).

Figure 10:
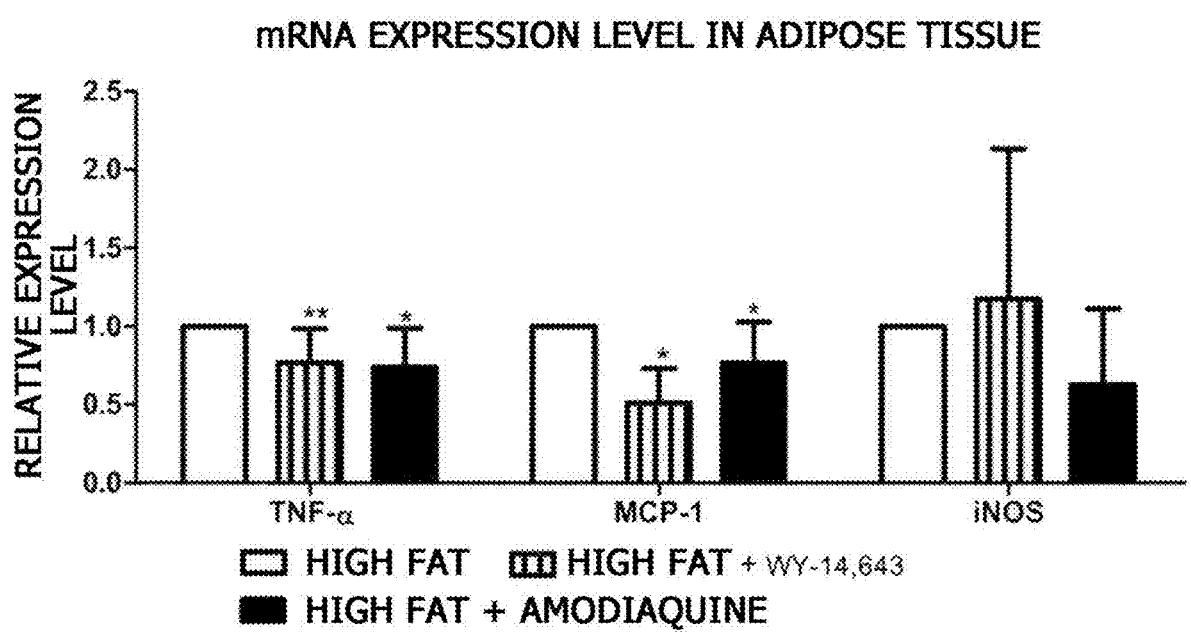
FIG. 10 is a graph showing results of measuring the expression of anti-inflammation-related genes in adipose tissues of high fat diet-induced obesity mice administered amodiaquine.

As a result, as illustrated in FIG. 10, it was confirmed that an approximate 540% decrease in expression levels of the genes was exhibited in the amodiaquine-administered experimental group as compared to that of the control.

Thus, from the result that amodiaquine treatment inhibited the expression of the TNFα, MCP-1, and iNOS genes, which are involved in inflammatory responses, in the adipose tissue, it was determined that amodiaquine would affect obesity, insulin resistance, and arteriosclerosis by inhibiting factors playing an important role in inflammatory responses.

Example 11. Measurement of Synergistic Effect on Gluconeogenesis Inhibition in Liver Cells According to Administration of Combined Preparation of Amodiaquine and Metformin It is known that insulin and glucagon, which are blood glucose-regulating hormones, control the activity of PEPCK, which is a glucose metabolism enzyme of liver tissue. Insulin inhibits gluconeogenesis by lowering the activity of PEPCK, which is a gluconeogenic enzyme, thereby reducing gluconeogenesis in liver tissue. On the other hand, glucagon inhibits glucokinase gene expression and promotes the G6Pase activity of liver tissue and mRNA expression and PEPCK transcription, and thus a small increase in glucagon concentration increases gluconeogenesis. PEPCK is a rate-limiting enzyme in gluconeogenesis and is known to catalyze the conversion of oxaloacetate to phosphoenolpyruvate. Thus, when an expression level of the PEPCK gene is measured, gluconeogenesis may be identified. Therefore, in the present example, the effect of treatment with a combined preparation of amodiaquine and metformin on the expression level of the PEPCK gene in liver cells was examined.

Human liver cells purchased from Korean Cell Line Bank were used as the cells, and primer base sequences of (β-actin and PEPCK are as follows:

```
β-actin forward:
                                        (SEQ ID NO: 2)
5'-GGG AAG GTG ACA GCA TTG-3'

Reverse:
                                        (SEQ ID NO: 3)
5'-ATG AAG TAT TAA GGC GGA AGA TT-3'

PEPCK forward:
                                        (SEQ ID NO: 16)
5'-CAG TTG AGT AGC ACA GAG AA-3'

Reverse:
                                        (SEQ ID NO: 17)
5'-GAT TCC TGA GTG ACC TTG AA-3'.
```

HepG2 liver cells were incubated in DMEM (10% FBS, penicillin-streptomycin) in a 37° C. incubator containing 5% $CO_2$, and then treated with the combined preparation of amodiaquine and metformin in serum-free DMEM and cultured for 24 hours, RNA was extracted using TRIzol, and cDNA was synthesized using reverse transcription polymerase chain reaction (RT PCR). As a control, β-actin was used, and to determine the expression level of the PEPCK gene, real-time polymerase chain reaction (RT PCR) was performed using primers (at 95° C. for 3 minutes, 39 cycles of 95° C. for 10 seconds, 60° C. for 10 seconds, and 72° C. for 30 seconds, at 95° C. for 10 seconds, and at 65° C. for 5 seconds). The PEPCK gene was calibrated with β-actin, thereby obtaining resultant values. For the experimental results, significance of the experimental group and the control was verified using a t-test, and the groups showed statistically significant differences ($p<0.005$ and $*p<0.0005$).

Figure 11:
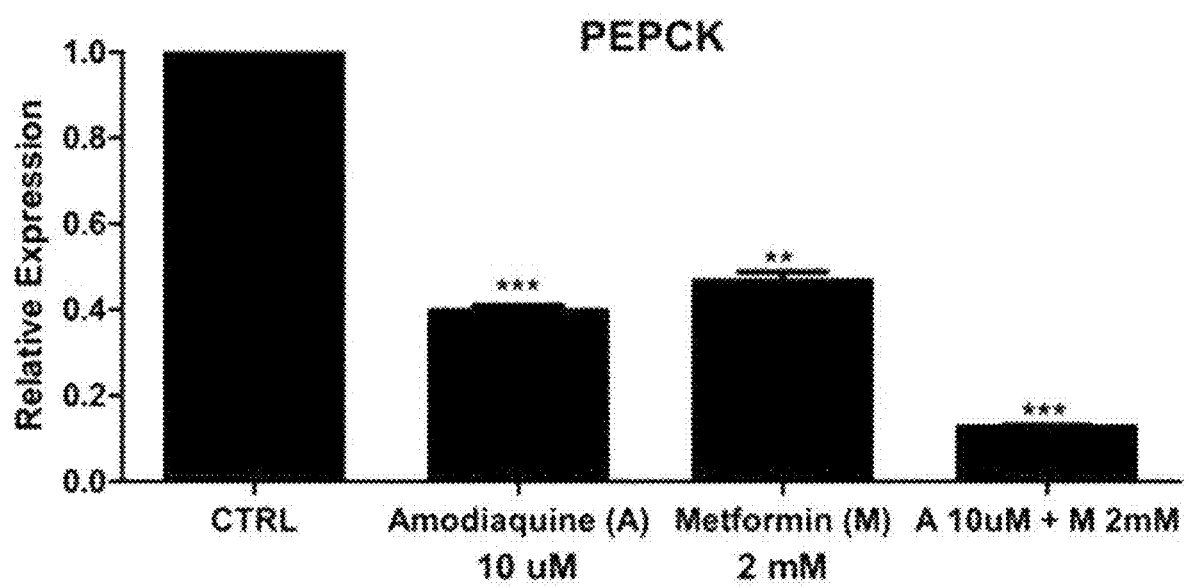
FIG. 11 is a graph showing results of measuring the expression of PEPCK, which is a gluconeogenesis-related gene, when a HepG2 cell line, which relates to human-derived liver cells, was treated with a combined preparation of amodiaquine and metformin for 24 hours.

As a result, as illustrated in FIG. 11, it was confirmed that upon treatment with a combined preparation of 10 μM amodiaquine and 2 mM metformin, a greater synergistic effect was exhibited than in the case of single treatment with 10 μM amodiaquine or 2 mM metformin. Thus, it is considered that treatment with the combined preparation of 10 μM amodiaquine and 2 mM metformin can reduce a fasting blood glucose concentration by inhibiting the expression of the PEPCK gene, which is a major enzyme in hepatic gluconeogenesis, and thus it can be seen that the combined preparation may be used for the treatment of diabetes, which is a related disease.

Example 12. Measurement of Synergistic Effect on Inhibition of Lipid Metabolism-Related Triglyceride and Phospholipid Biosynthesis in Liver Cells According to Combined Preparation of Amodiaquine and Metformin SREBP-1 is known to inhibit lipogenesis and body fat accumulation by participating in the regulation of genes involved in lipid metabolism-related triglyceride and phospholipid biosynthesis, and a study has reported that inactivation of the SREBP-1 gene in fatty liver lesions occurring in ob/ob mice, which are characterized by high obesity and insulin resistance, reduces triglyceride accumulation in liver tissue. Thus, when an expression level of the SREBP-1 gene is measured, an effect of reducing triglyceride accumulation in liver tissue may be identified. Therefore, in the present example, the effect of treatment with the combined preparation of amodiaquine and metformin on the expression level of the SREBP-1 gene in liver cells was examined.

Mouse liver cells purchased from Korean Cell Line Bank were used as the cells, and primer base sequences of (β-actin and SREBP-1 are as follows:

β-actin forward:
(SEQ ID NO: 2)
5'-GGG AAG GTG ACA GCA TTG-3'

Reverse:
(SEQ ID NO: 3)
5'-ATG AAG TAT TAA GGC GGA AGA TT-3'

SREBP-1 forward:
(SEQ ID NO: 18)
5'-CGA CTA CAT CCG CTT CTT G-3'

Reverse:
(SEQ ID NO: 19)
5'-GGT CCT TCA GTG ATT TGC TT-3'.

HepG2 liver cells were incubated in DMEM (10% FBS, 1% penicillin-streptomycin) in a 37° C. incubator containing 5% $CO_2$, and then treated with the combined preparation of amodiaquine and metformin in serum-free DMEM and cultured for 24 hours, RNA was extracted using a QIAGEN RNA extraction kit (QIAGEN, Hilden, Germany), and then cDNA was synthesized using reverse transcription polymerase chain reaction (RT PCR). As a control, β-actin was used, and to determine the expression level of the SREBP-1 gene, real-time polymerase chain reaction (RT PCR) was performed using primers (at 95° C. for 3 minutes, 39 cycles of 95° C. for 10 seconds, 60° C. for 10 seconds, and 72° C. for 30 seconds, at 95° C. for 10 seconds, and at 65° C. for 5 seconds). The SREBP-1 gene was calibrated with β-actin, thereby obtaining resultant values. For the experimental results, significance of the experimental group and the control was verified using a t-test, and the groups showed statistically significant differences ($*p<0.05$ and $**p<0.005$).

Figure 12:
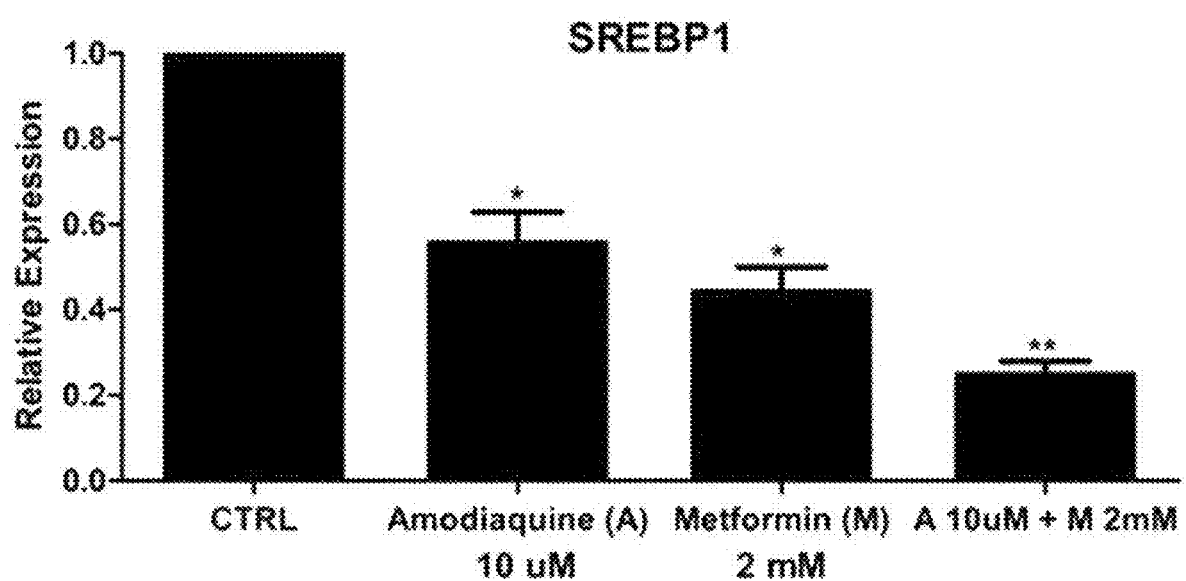
FIG. 12 is a graph showing results of measuring the expression of SREBP-1, which is a gene related to triglyceride and phospholipid biosynthesis associated with lipid metabolism, when a HepG2 cell line, which relates to human-derived liver cells, was treated with a combined preparation of amodiaquine and metformin for 24 hours.

As a result, as illustrated in FIG. 12, it was confirmed that upon treatment with a combined preparation of 10 μM amodiaquine and 2 mM metformin, a greater synergistic effect was exhibited than in the case of single treatment with 10 μM amodiaquine or 2 mM metformin. Thus, it is considered that treatment with the combined preparation of 10 μM amodiaquine and 2 mM metformin can reduce triglyceride accumulation in liver tissue in fatty liver lesions by inhibiting the expression of the SREBP-1 gene, which is a major protein involved in the synthesis of fatty acids and triglycerides in liver tissue, and thus it can be seen that the combined preparation may be used for the treatment of fatty liver, which is a related disease.

Example 13. Identification of Expression of GLUT4 Gene in Muscle Cells in Palmitic Acid-Induced Insulin Resistance State According to Administration of Combined Preparation of Amodiaquine and Metformin It is well known that the expression of glucose transporter type 4 (GLUT4) is increased by various transcription factors in skeletal muscles and a quantitative increase in GLUT4 expression also increases insulin responsiveness (J M Ren et al., J. Clin. Invest., 95:429-432, 1995). Thus, since the level of GLUT4 in skeletal muscles is important for regulating blood glucose in the body, when an expression level of the GLUT4 gene is measured, insulin responsiveness may be identified. Therefore, in the present invention, the effect of treatment with the combined preparation of amodiaquine and metformin on the expression level of the GLUT4 gene in muscle cells in a palmitic acid-induced insulin resistance state was examined.

Mouse myoblasts purchased from Korean Cell Line Bank were used as the cells, and primer base sequences of (β-actin and GLUT4 are as follows:

β-actin forward:
(SEQ ID NO: 2)
5'-GGG AAG GTG ACA GCA TTG-3'

Reverse:
(SEQ ID NO: 3)
5'-ATG AAG TAT TAA GGC GGA AGA TT-3'

GLUT4 forward:
(SEQ ID NO: 20)
5'-AAA TCT AGC CCT GCC TCC-3'

Reverse:
(SEQ ID NO: 21)
5'-GCT CTA ACC GTC CTT GCC-3'.

$1\times10^7$ C2C12 cells (mouse myoblasts) were differentiated into myotubes with 2% horse serum, and then treated with 400 μM palmitic acid and a combined preparation of amodiaquine and metformin for 16 hours, for an experiment under insulin resistance conditions, and then RNA was extracted using a QIAGEN RNeasy Mini kit (Qiagen, USA). The extracted RNA was verified to be complete using Bioanalyzer 2100 (Agilent, USA), and cDNA was synthesized using reverse transcription polymerase chain reaction (RT PCR). As a control, β-actin was used, and to determine the expression level of the GLUT4 gene, real-time polymerase chain reaction (RT PCR) was performed using primers (at 95° C. for 3 minutes, 39 cycles of 95° C. for 10 seconds, 60° C. for 10 seconds, and 72° C. for 30 seconds, at 95° C. for 10 seconds, and at 65° C. for 5 seconds). The GLUT4 gene was calibrated with β-actin, thereby obtaining resultant values. For the experimental results, significance of the experimental group and the control was verified using a t-test, and the groups showed statistically significant differences ($*p<0.05$ and $***p<0.0005$).

Figure 13:
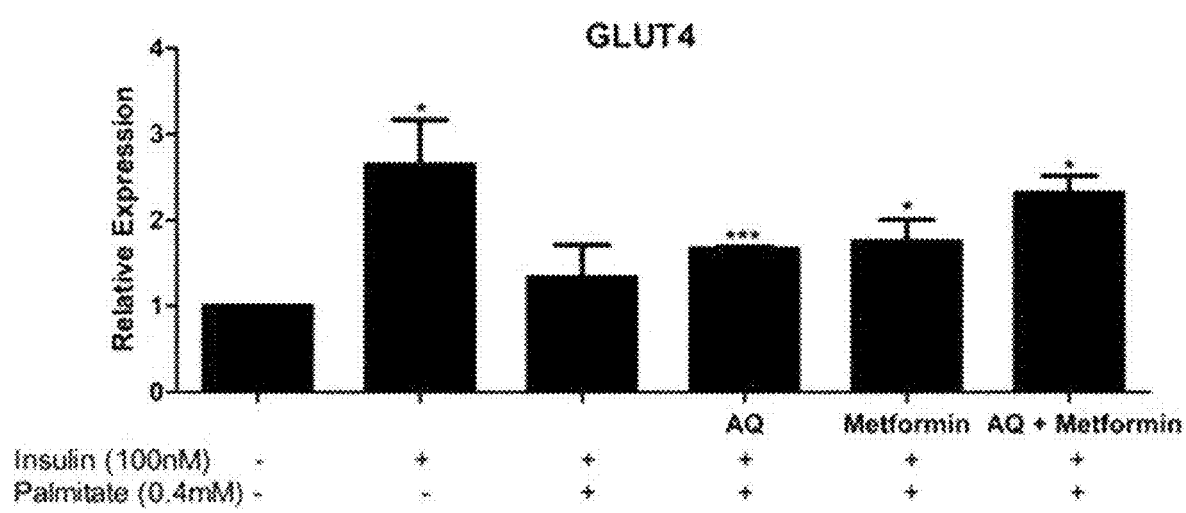
FIG. 13 is a graph showing results of measuring the expression of GLUT4, which is a gene related to insulin responsiveness, when C2C12 cells, which are differentiated mouse-derived muscle cells, were treated with a combined preparation of amodiaquine and metformin, along with palmitic acid used to induce insulin resistance for 16 hours.
Figure 14A:
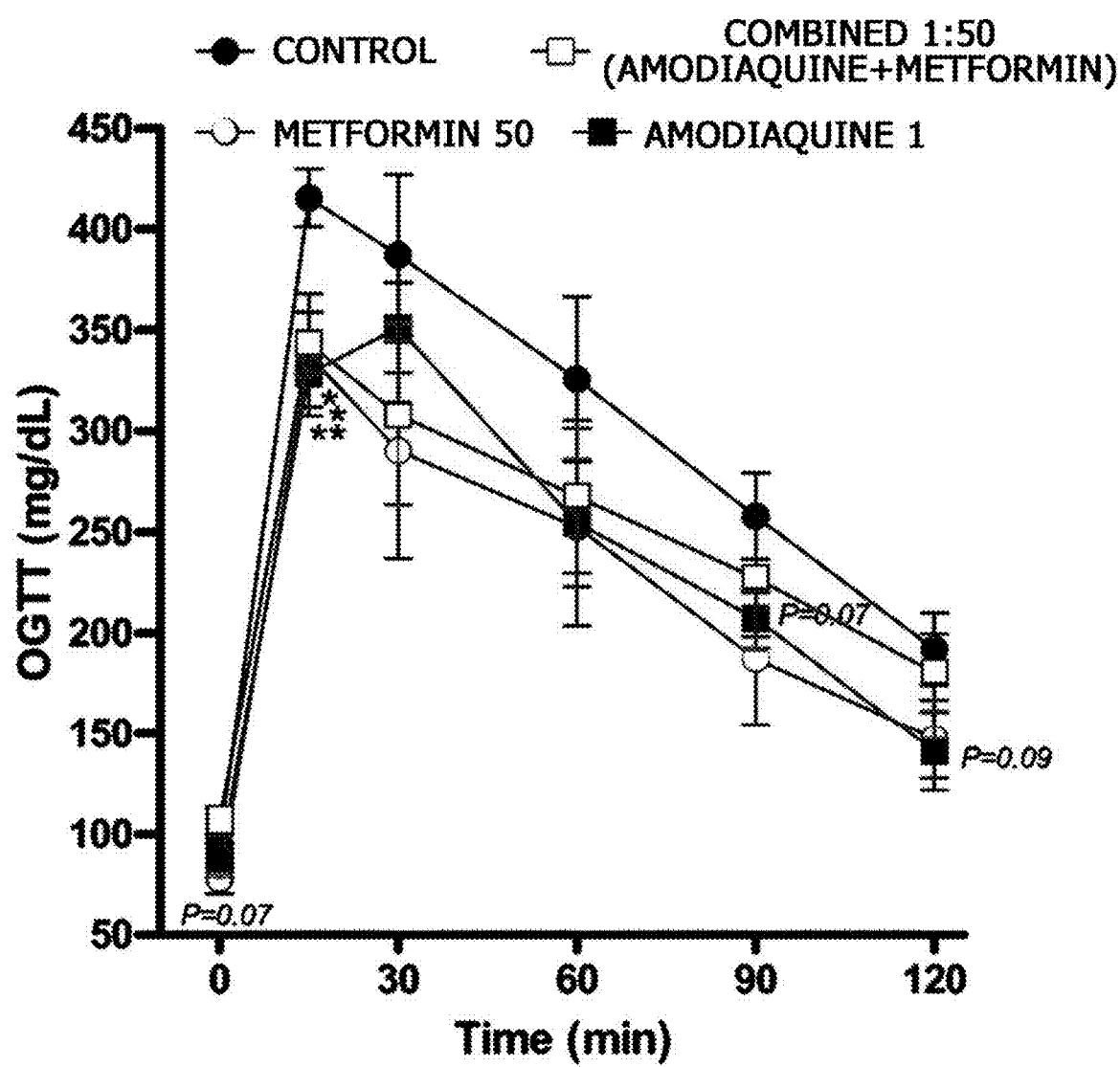
FIGS. 14A, 14B, 14C, and 14D are graphs showing OGTT results of confirming an effect on a change in blood glucose over time after glucose was administered to mice administered amodiaquine and metformin in weight ratios of 1:50, 1:150, 1:300, and 1:500, respectively.
Figure 14B:
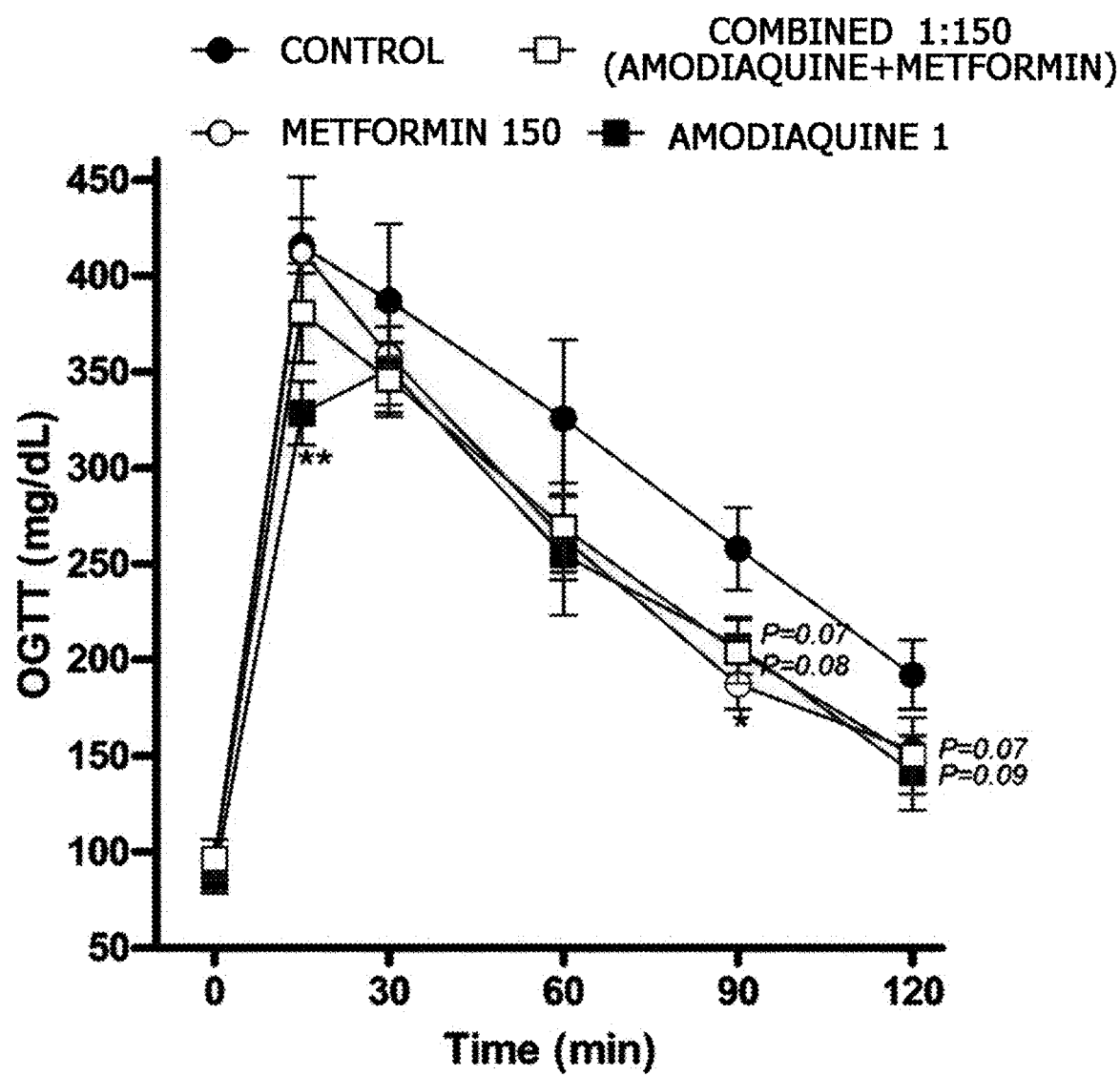
Figure 14C:
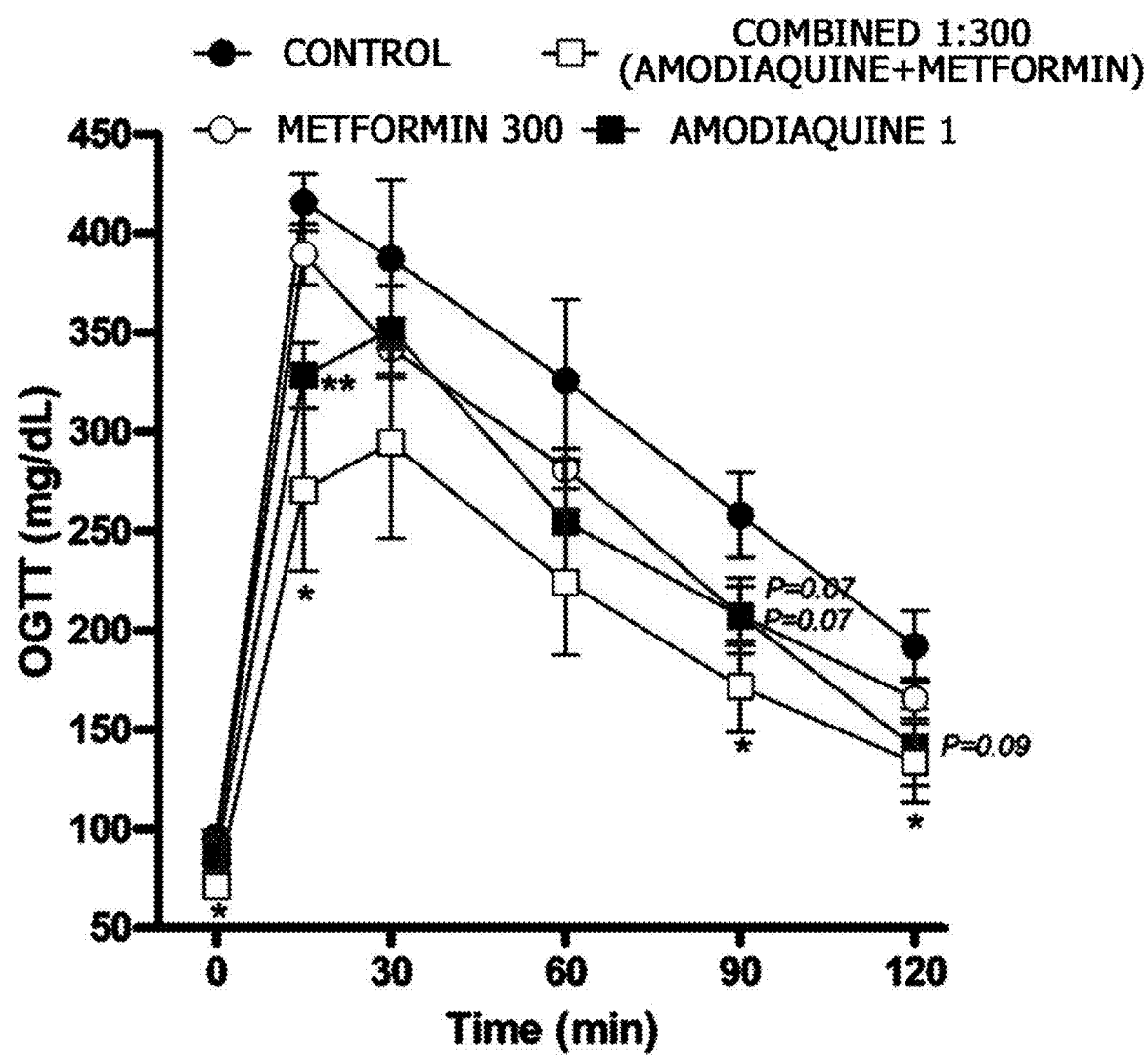
Figure 14D:
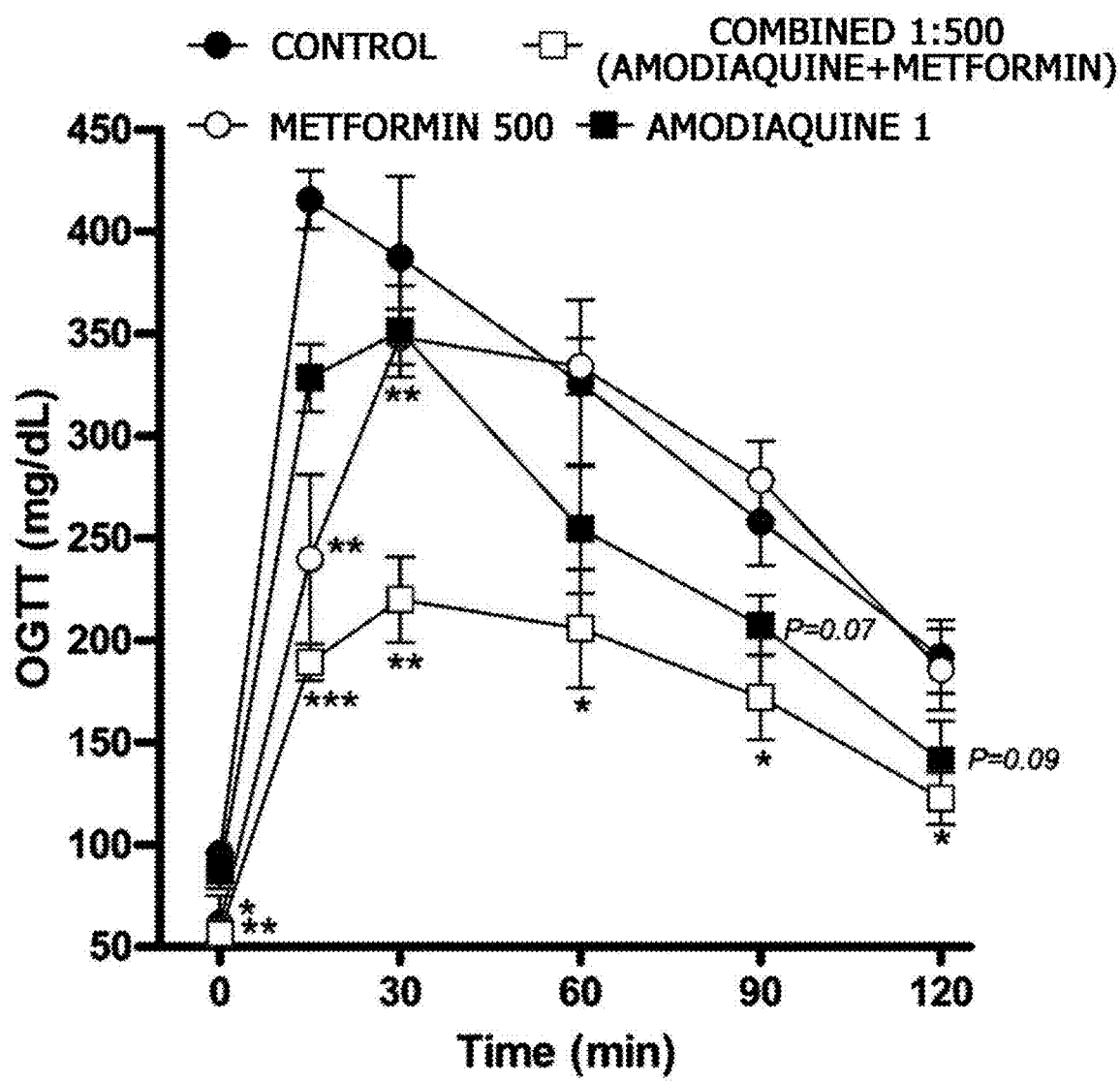
Figure 15A:
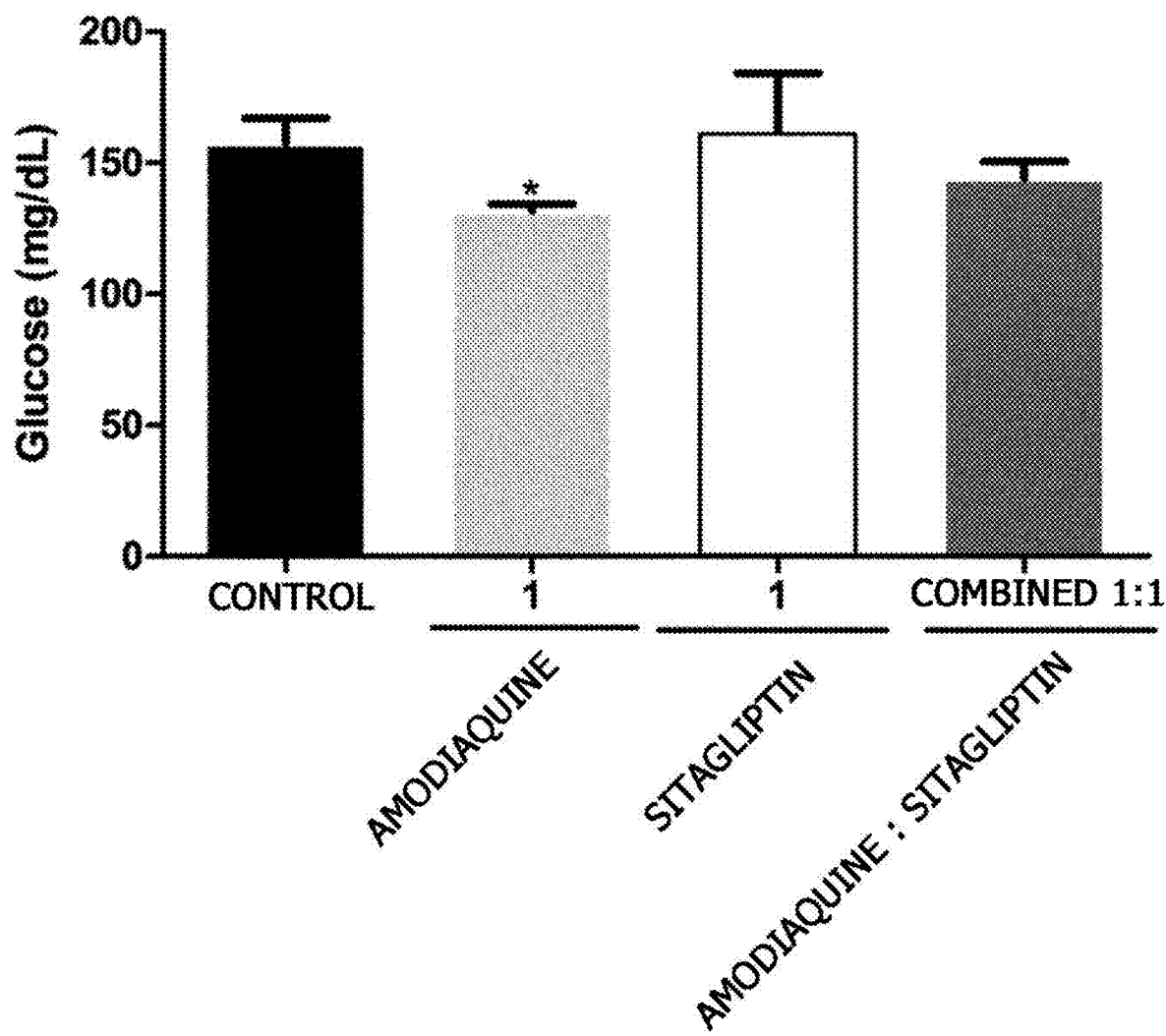
FIGS. 15A, 15B, 15C, and 15D are graphs showing results of confirming an effect on a change in fasting blood glucose of mice administered amodiaquine and sitagliptin in weight ratios of 1:1, 1:2, 1:10, and 1:20, respectively.
Figure 15B:
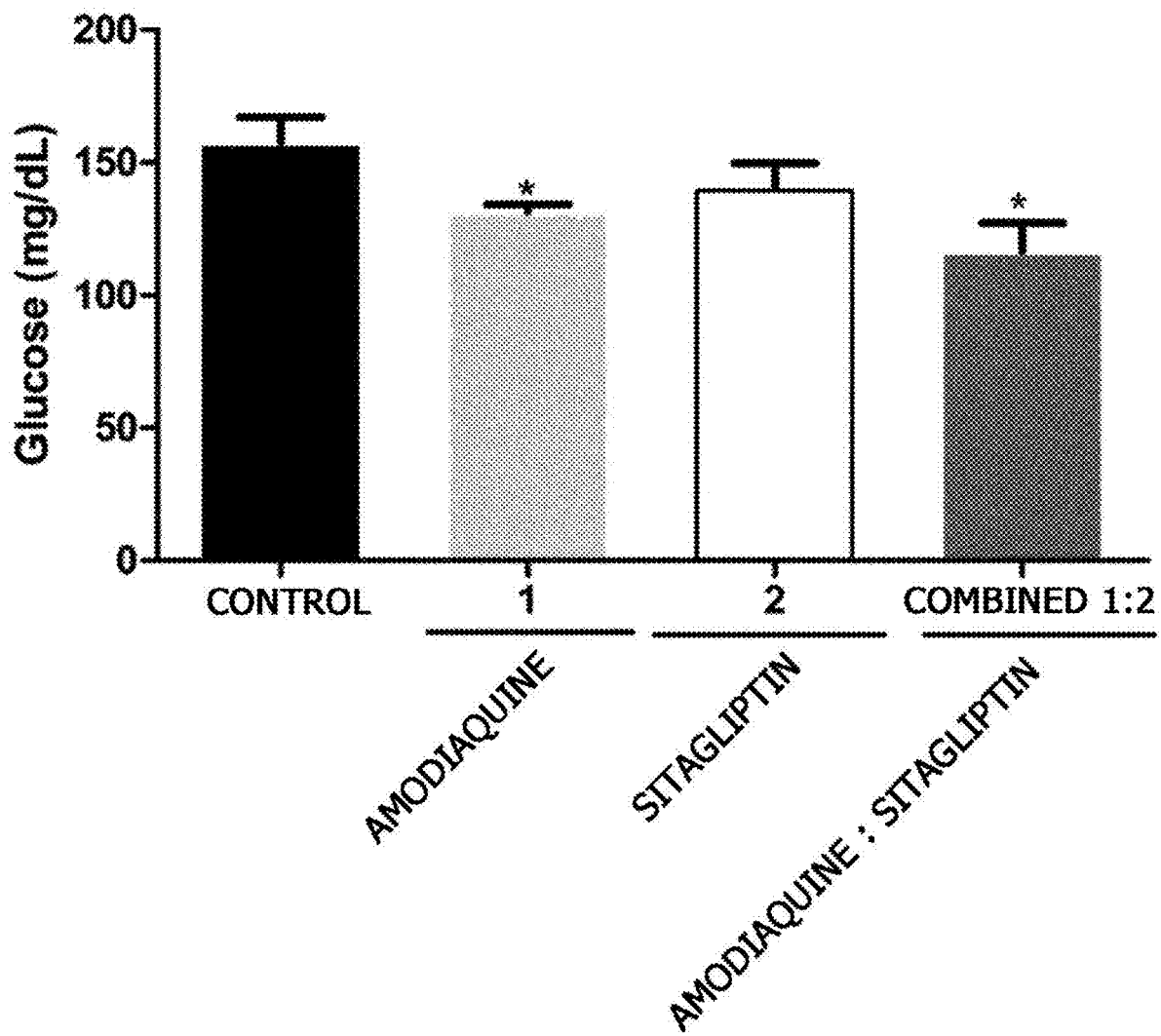
Figure 15C:
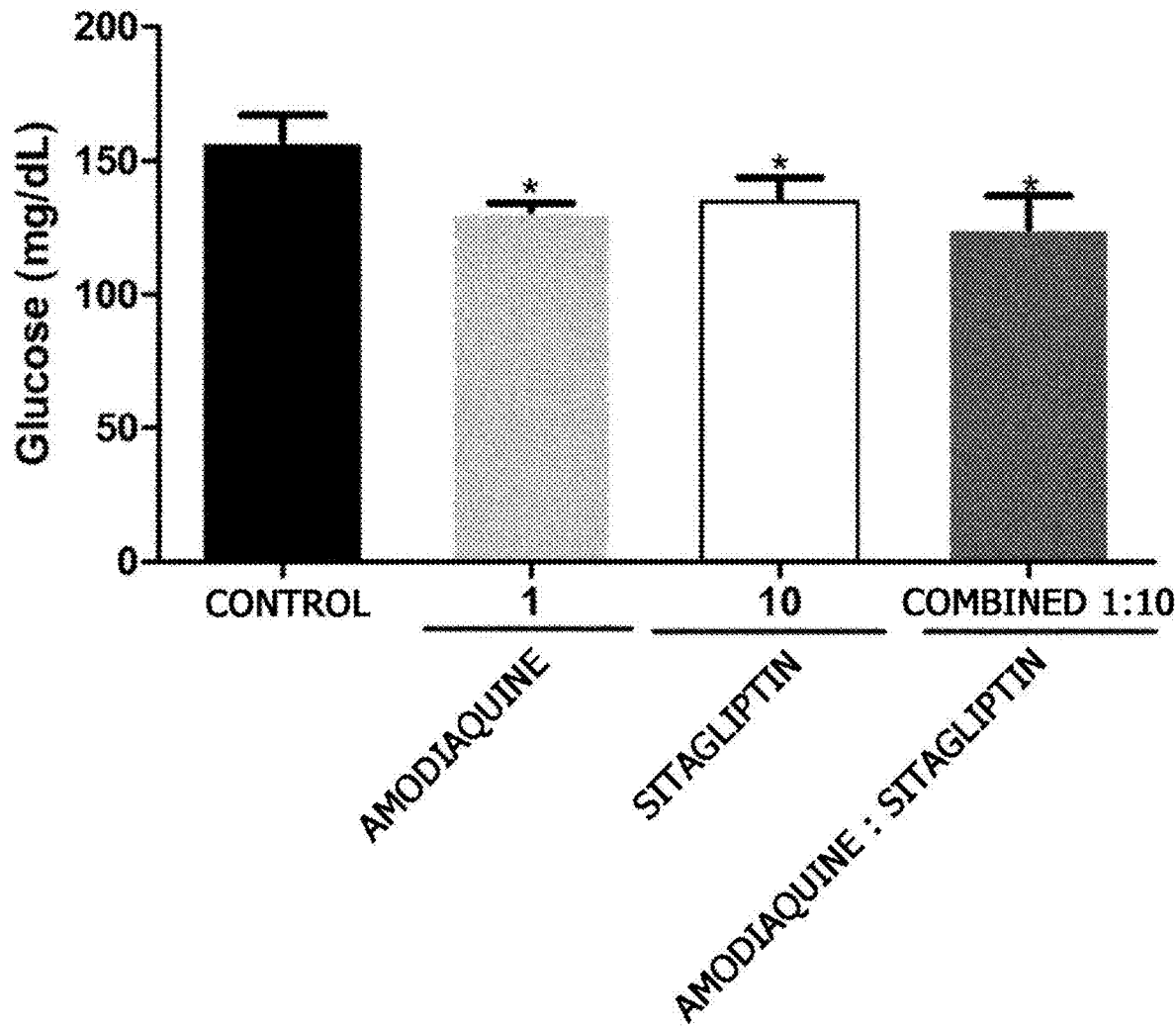
Figure 15D:
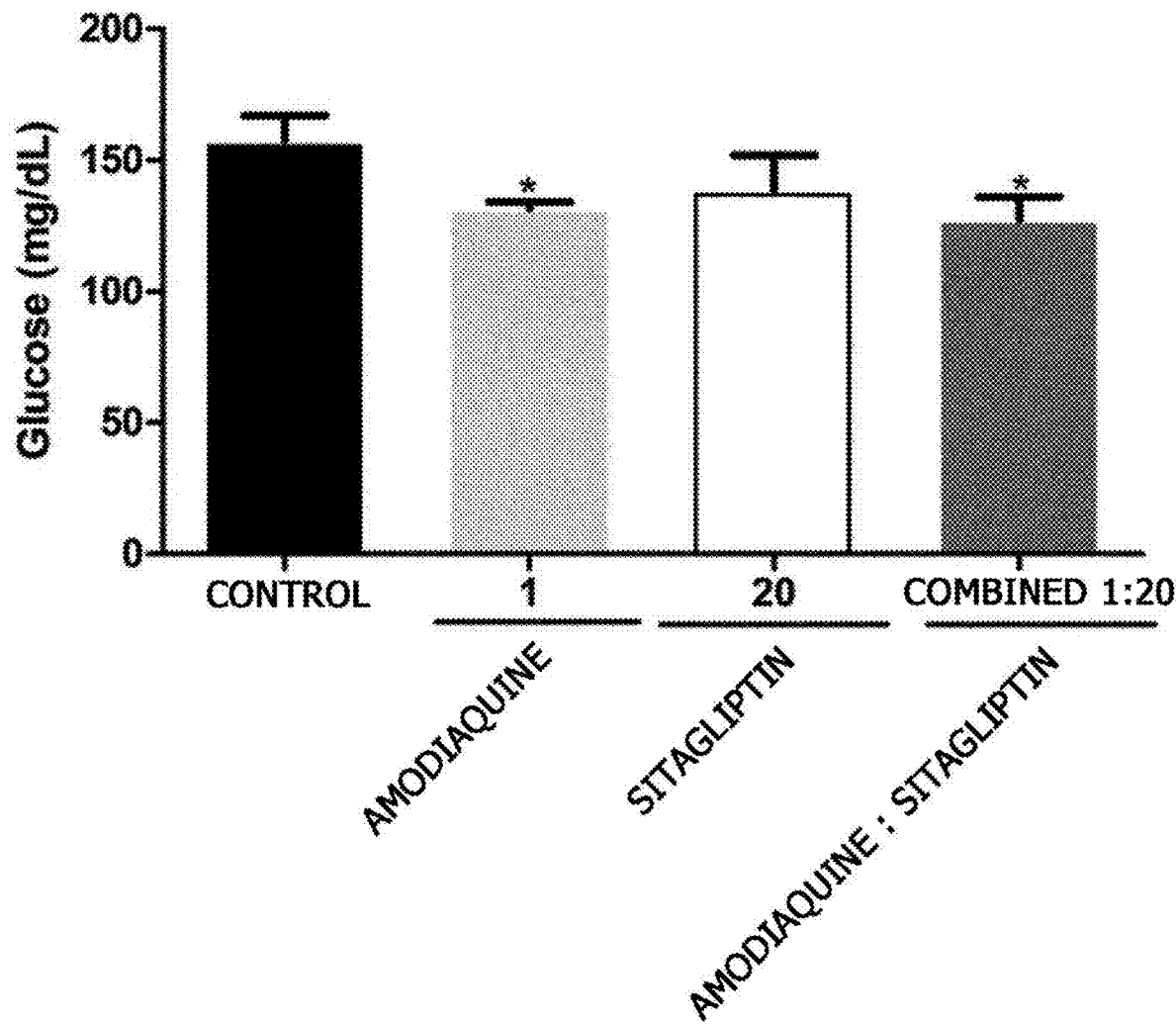
Figure 15E:
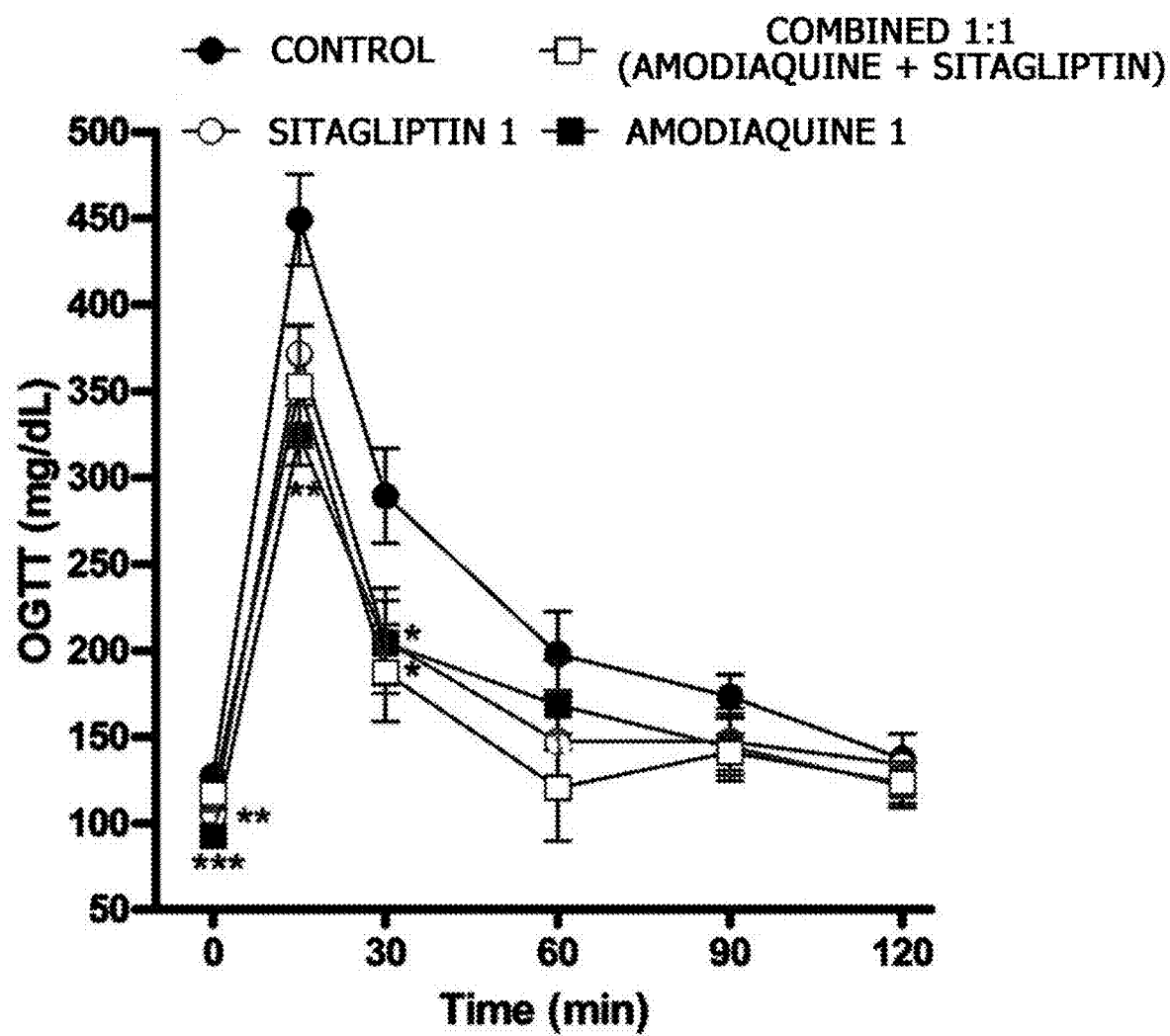
FIGS. 15E, 15F, 15G, and 15H are graphs showing OGTT results of confirming an effect on a change in blood glucose over time after glucose was administered to mice administered amodiaquine and sitagliptin in weight ratios of 1:1, 1:2, 1:10, and 1:20, respectively.
Figure 15F:
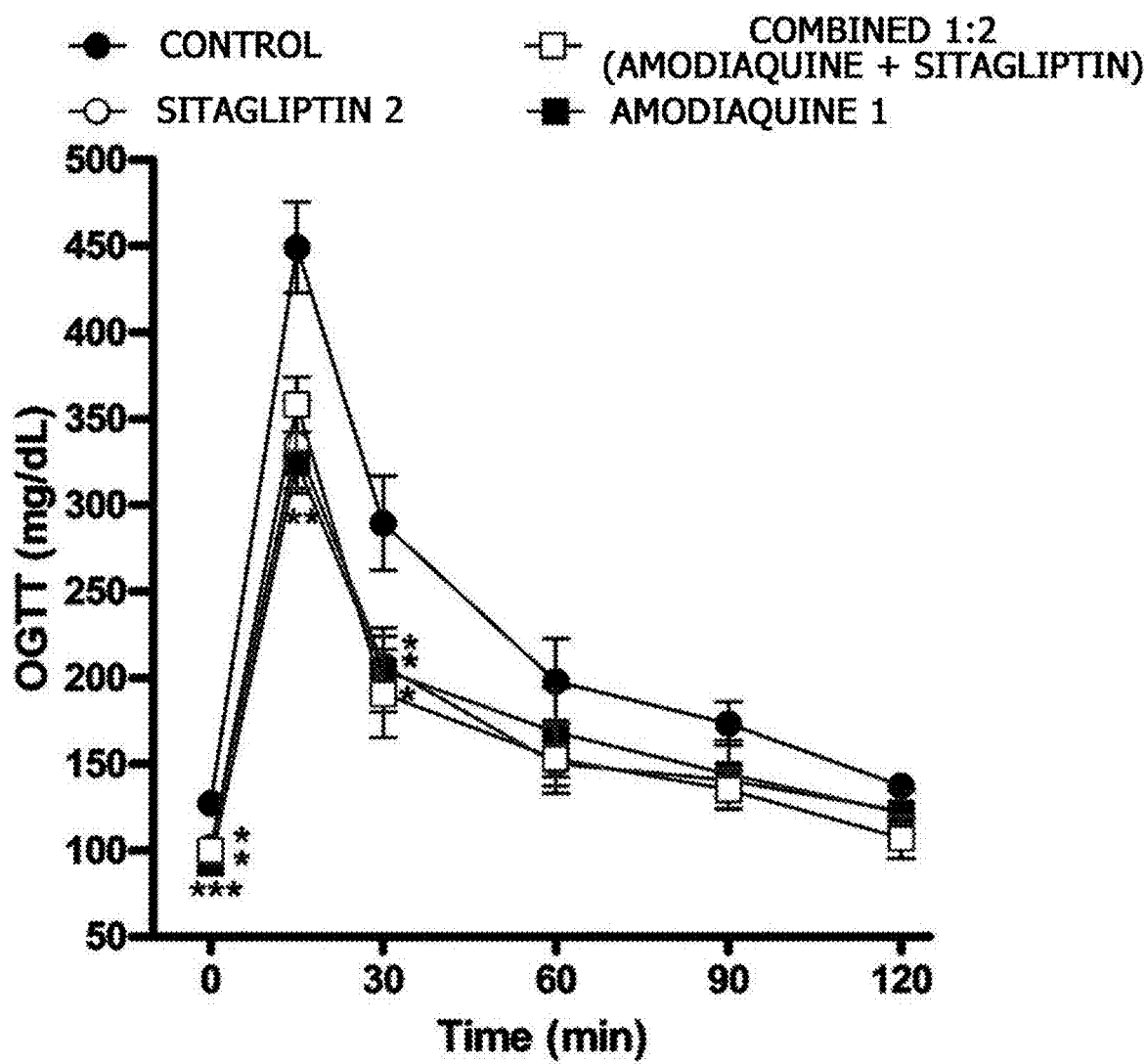
Figure 15G:
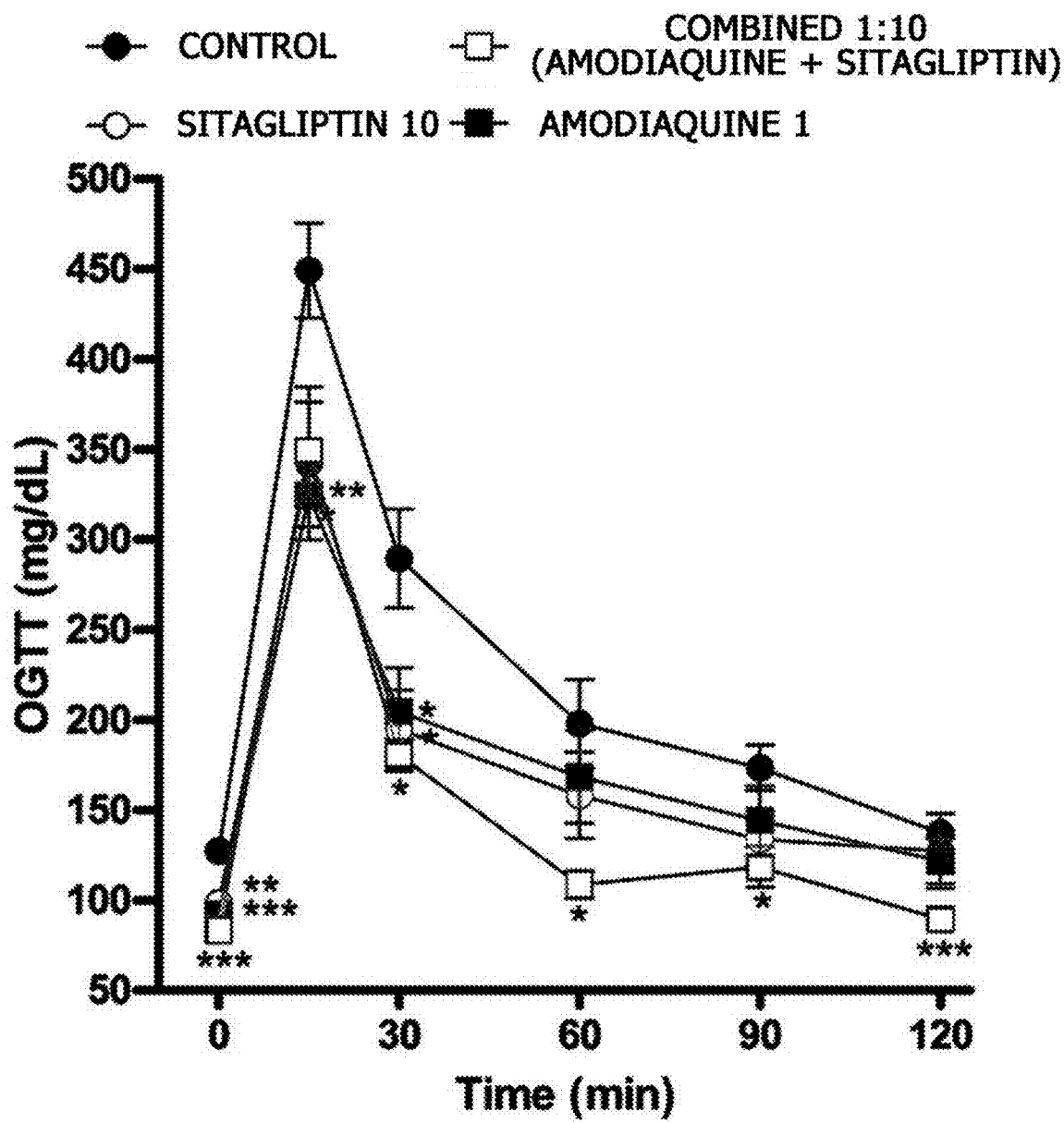
Figure 15H:
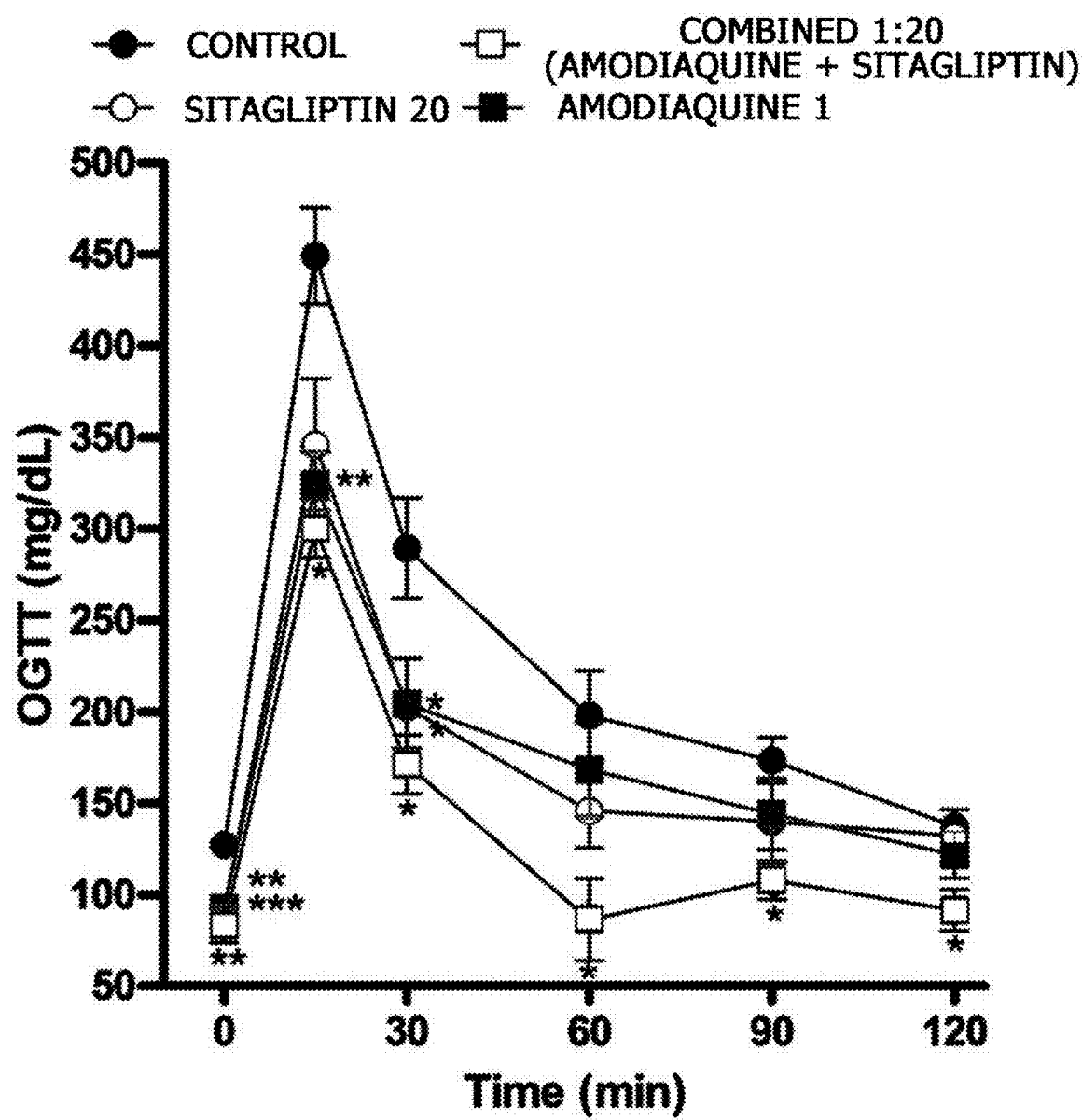
Figure 15I:
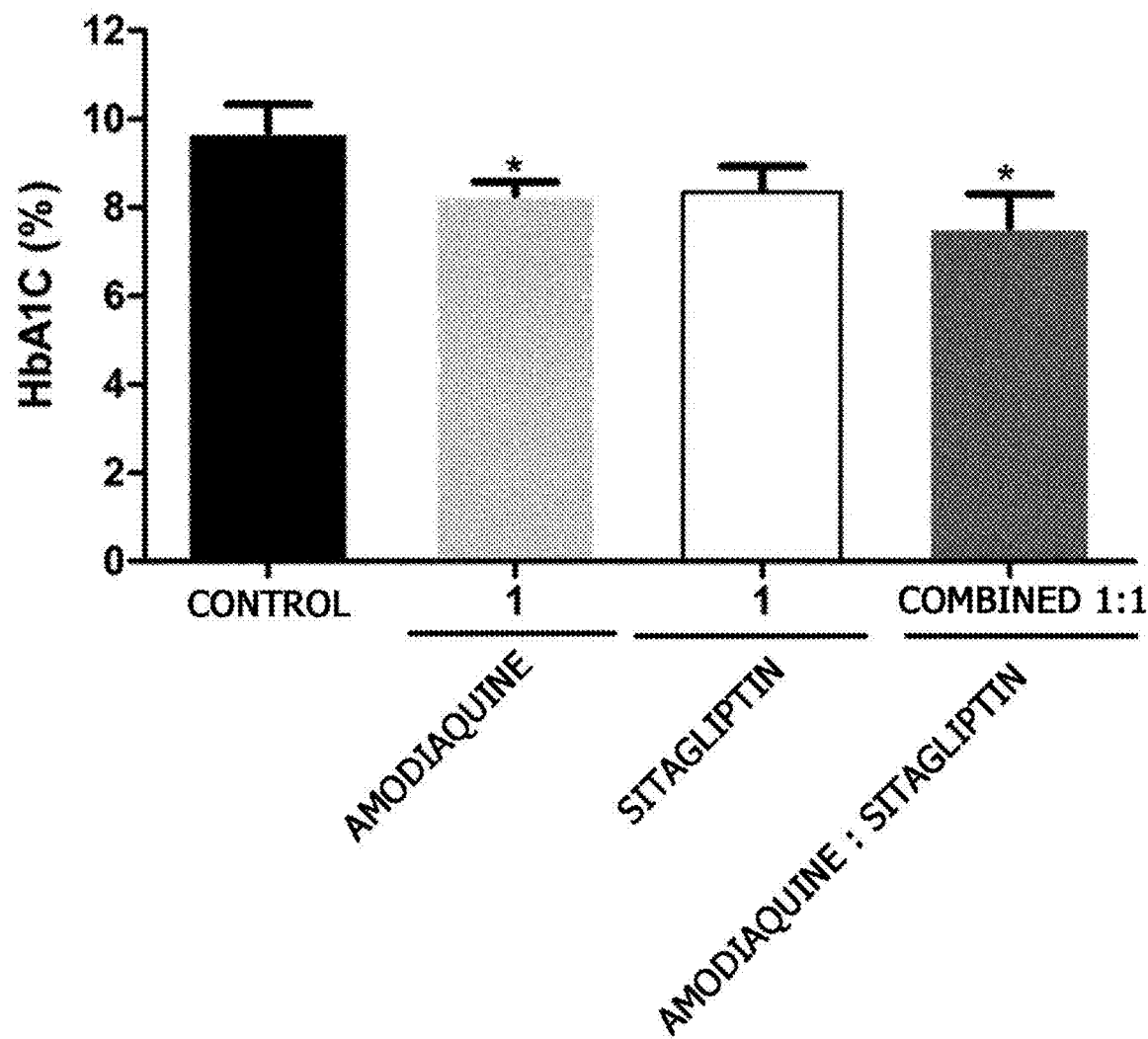
FIGS. 15I, 15J, 15K, and 15L are graphs showing results of confirming an effect on glycated hemoglobin levels of mice administered amodiaquine and sitagliptin in weight ratios of 1:1, 1:2, 1:10, and 1:20, respectively.
Figure 15J:
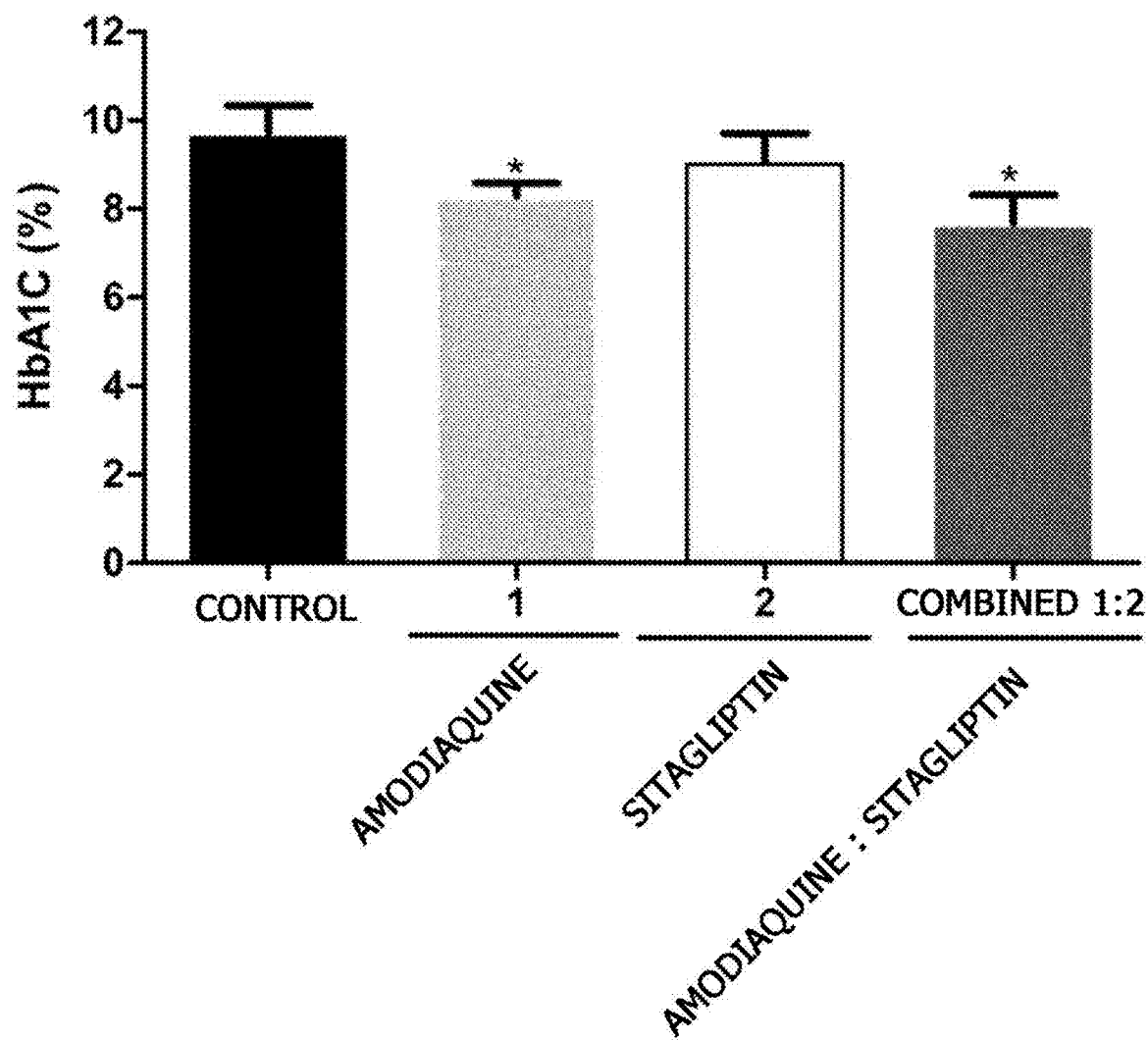
Figure 15K:
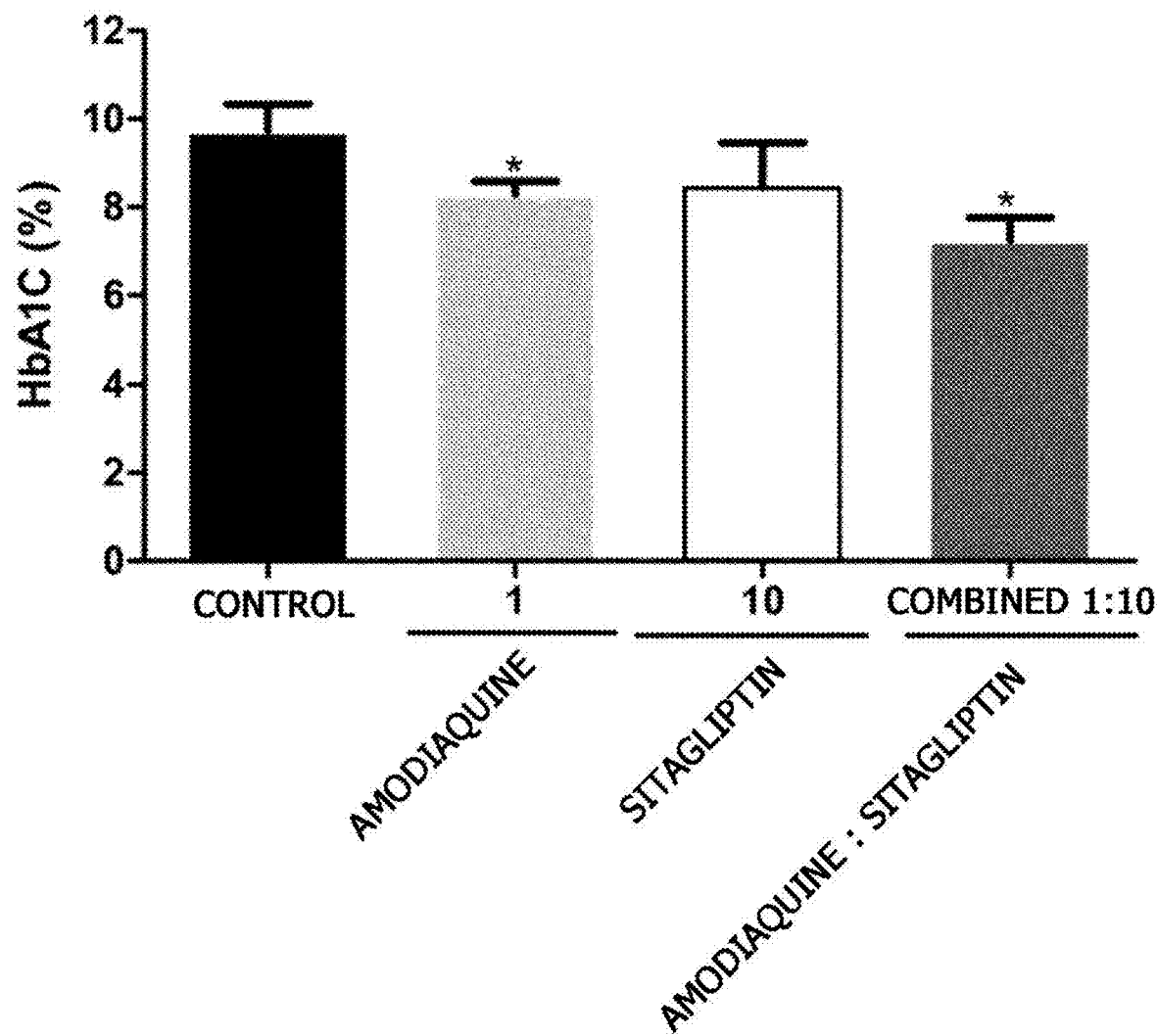
Figure 15L:
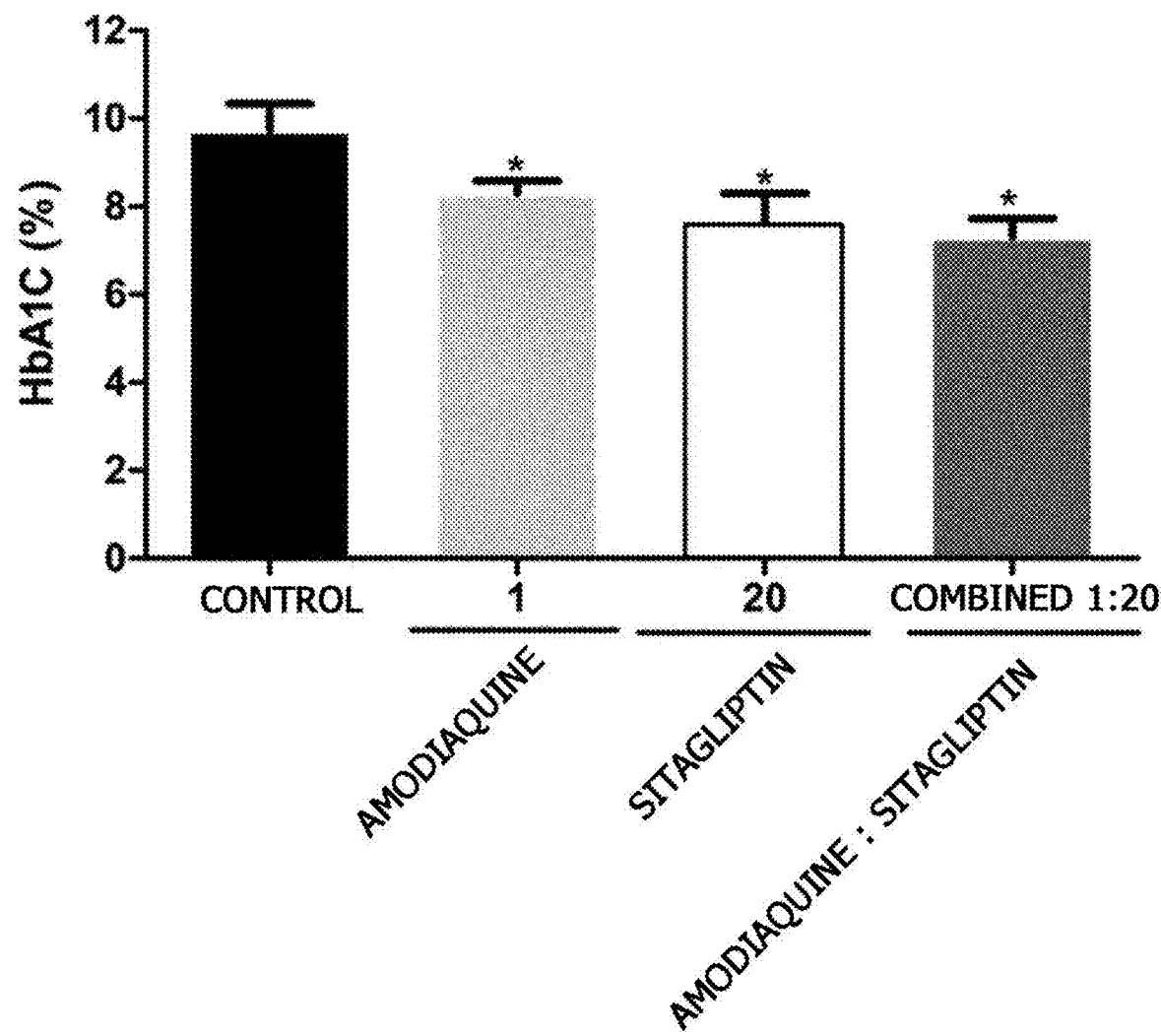

As a result, as illustrated in FIG. 13, it was confirmed that while GLUT4 expression was not significantly increased by insulin when differentiated C2C12 skeletal muscle cells were treated with 400 μM palmitic acid for 16 hours to induce an insulin resistance state, the case of treatment with the combined preparation of 10 μM amodiaquine and 2 mM metformin exhibited a greater synergistic effect than that in the case of single treatment with 10 μM amodiaquine or 2 mM metformin. From the result, it was confirmed that the treatment with the combined preparation of 10 M amodiaquine and 2 mM metformin had a positive effect on blood glucose regulation and saccharometabolism improvement through an increase in GLUT4 gene expression in muscle cells under insulin resistance conditions, and it can be seen that the combined preparation may be used for the treatment of diabetes, which is a related disease.

Example 14. Measurement of Blood Glucose Regulation Effect in Mice According to Administration of Combined Preparation of Amodiaquine and Metformin 14-1. Administration of Amodiaquine or Metformin or Combined Preparation Thereof To measure an effect of a combined preparation of amodiaquine and metformin on blood glucose regulation, 6-week-old KKAy mice were purchased from Clea Japan and raised under certain conditions (temperature: 22±2° C., relative humidity: 55±10%, and light/dark cycle: 12 hours). The mice were grouped into 7 individuals per group, freely fed water and diets in a cage, and then acclimated for 1 week before an experiment.

After acclimatization, the mice were divided into 10 groups, and orally administered amodiaquine or metformin alone or a combined preparation thereof every day for 6 weeks at weight ratios shown in Table 2 below.

TABLE 2

| Group | Amodiaquine | Metformin |
|---|---|---|
| Normal control | — | — |
| Amodiaquine or metformin-administered group | 1 | — |
|  | — | 50 |
|  | — | 150 |
|  | — | 300 |
|  | — | 500 |
| Group administered combined preparation of amodiaquine and metformin | 1 | 50 |
|  | 1 | 150 |
|  | 1 | 300 |
|  | 1 | 500 |

14-2. Measurement of Blood Glucose Regulation Effect in Mice

To identify the blood glucose regulation effect, 2 g/kg of glucose was intraperitoneally injected into control and experimental group animals after 16-hour fasting, and a blood glucose concentration was measured every 30 minutes for 2 hours. For measurement of the blood glucose concentration, an oral glucose tolerance test (OGTT) was used. For the experimental results, significance of the experimental groups and the control was verified using an independent group t-test, and the groups showed statistically significant differences (*p<0.05, p<0.005, and *p<0.0005).

As a result, as illustrated in FIGS. 14A to 14D, it was confirmed that a blood glucose concentration 2 hours after glucose administration was rapidly reduced in the group administered the combined preparation of amodiaquine and metformin in a weight ratio of 1:300 or 1:500 not in weight ratios of 1:50 and 1:150, as compared to the amodiaquine- or metformin-administered group.

From the above result, it was confirmed that an excellent synergistic effect of reducing a blood glucose concentration was exhibited in the combined preparation-administered group as compared to the group administered amodiaquine or metformin alone, and thus it can be seen that the combined preparation of amodiaquine and metformin in a weight ratio of 1:300 or 1:500 may be effectively used for the prevention or treatment of diabetes and may also be effectively used as an agent for preventing or treating insulin-resistant type 2 diabetes.

Example 15. Effect of Administration of Combined Preparation of Amodiaquine and Sitagliptin on Blood Glucose Reduction, Blood Glucose Regulation, and Glycated Hemoglobin Content in Mice 15-1. Administration of Amodiaquine or Sitagliptin or Combined Preparation Thereof To measure an effect of a combined preparation of amodiaquine and sitagliptin on blood glucose regulation, 6-week-old KKAy mice were purchased from Clea Japan and raised under certain conditions (temperature: 22±2° C., relative humidity: 55±10%, and light/dark cycle: 12 hours). The mice were grouped into 7 individuals per group, freely fed water and diets in a cage, and then acclimated for 1 week before an experiment.

After acclimatization, the mice were divided into 10 groups, and orally administered amodiaquine or sitagliptin alone or a combined preparation thereof every day for 8 weeks at weight ratios shown in Table 3 below.

TABLE 3

| Group | Amodiaquine | Sitagliptin |
|---|---|---|
| Normal control | — | — |
| Amodiaquine- or sitagliptin-administered group | 1 | — |
|  | — | 1 |
|  | — | 2 |
|  | — | 10 |
|  | — | 20 |
| Group administered combined preparation of amodiaquine and metformin | 1 | 1 |
|  | 1 | 2 |
|  | 1 | 10 |
|  | 1 | 20 |

15-2. Measurement of Fasting Blood Glucose Lowering Effect in Mice

A fasting blood glucose concentration after 16-hour fasting was measured by collecting whole blood from the caudal vein on week 8 after drug treatment. A blood glucose strip (Green Cross, Gyeonggi-do, Korea) was used to measure blood glucose. For the experimental results, significance of the experimental group and the control was verified using a t-test, and the groups showed a statistically significant difference (*p<0.05). As a result, as illustrated in FIGS. 15A to 15D, it was confirmed that a synergistic effect of significantly lowering fasting blood glucose was exhibited in the group administered the combined preparation of amodiaquine and sitagliptin in a weight ratio of 1:2, 1:10, or 1:20, not in a weight ratio of 1:1, as compared to the amodiaquine- or sitagliptin-administered group.

15-3. Measurement of Blood Glucose Regulation Effect in Mice

To identify the blood glucose regulation effect, 2 g/kg of glucose was intraperitoneally injected into control and experimental group animals after 16-hour fasting, and a blood glucose concentration was measured every 30 minutes for 2 hours. For measurement of the blood glucose concentration, an oral glucose tolerance test (OGTT) was used. For the experimental results, significance of the experimental groups and the control was verified using an independent group t-test, and the groups showed statistically significant differences (*p<0.05, p<0.005, and *p<0.0005).

As a result, as illustrated in FIGS. 15E to 15H, it was confirmed that a blood glucose concentration 2 hours after glucose administration was rapidly reduced in the group administered the combined preparation of amodiaquine and sitagliptin in a weight ratio of 1:10 or 1:20 not in weight ratios of 1:1 and 1:2, as compared to the amodiaquine- or sitagliptin-administered group.

From the above result, it was confirmed that an excellent synergistic effect of reducing a blood glucose concentration was exhibited in the combined preparation-administered group as compared to the group administered amodiaquine or sitagliptin alone, and thus it can be seen that the combined preparation of amodiaquine and sitagliptin in a weight ratio of 1:10 or 1:20 may be effectively used for the prevention or treatment of diabetes and may also be effectively used as an agent for preventing or treating insulin-resistant type 2 diabetes.

15-4. Measurement of Glycated Hemoglobin in Mice

To investigate blood glucose regulation, not only a blood glucose level but also a glycated hemoglobin level is examined. This is because a 1% decrease in glycated hemoglobin leads to a 20% or more decrease in complications due to diabetes. In the present example, glycated hemoglobin contents of mice due to the intake of the combined preparation of amodiaquine and sitagliptin were examined. To measure an effect of the combined preparation of amodiaquine and sitagliptin on lowering glycated hemoglobin, whole blood was collected from the caudal vein of the control and experimental group animals and injected into a Hemoglobin A1c reagent kit, and then measurement was performed thereon using a DCA vantage analyzer (USA, New York, Siemens). For the experimental results, significance of the experimental groups and the control was verified using an independent group t-test, and the groups showed a statistically significant difference (*p<0.05).

As a result, as illustrated in FIGS. 15I to 15L, it was confirmed that a glycated hemoglobin generation inhibitory effect was enhanced in the group administered the combined preparation of amodiaquine and sitagliptin in a weight ratio of 1:1, 1:2, 1:10, or 1:20, as compared to the amodiaquine- or sitagliptin-administered group.

From the above result, it was confirmed that the combined preparation of amodiaquine and sitagliptin had an effect of reducing glycated hemoglobin, and thus it can be seen that the combined preparation may be effectively used as an agent for preventing or treating insulin-resistant type 2 diabetes.

Example 16. Effect of Administration of Combined Preparation of Amodiaquine and Dapagliflozin on Blood Glucose Reduction, Blood Glucose Regulation, and Glycated Hemoglobin Content in Mice 16-1. Administration of Amodiaquine or Dapagliflozin or Combined Preparation Thereof To measure an effect of a combined preparation of amodiaquine and dapagliflozin on blood glucose regulation, 6-week-old KKAy mice were purchased from Clea Japan and raised under certain conditions (temperature: 22±2° C., relative humidity: 55±10%, and light/dark cycle: 12 hours). The mice were grouped into 7 individuals per group, freely fed water and diets in a cage, and then acclimated for 4 weeks before an experiment.

After acclimatization, the mice were divided into 8 groups, and orally administered amodiaquine or dapagliflozin alone or a combined preparation thereof every day for 8 weeks at weight ratios shown in Table 4 below.

TABLE 4

| Group | Amodiaquine | Dapagliflozin |
|---|---|---|
| Normal control | — | — |
| Amodiaquine- or dapagliflozin- administered group | 1 | — |
|  | — | 0.02 |
|  | — | 0.2 |
|  | — | 2 |
| Group administered combined preparation of amodiaquine and dapagliflozin | 1 | 0.02 |
|  | 1 | 0.2 |
|  | 1 | 2 |

16-2. Measurement of Fasting Blood Glucose Lowering Effect in Mice

Figure 16A:
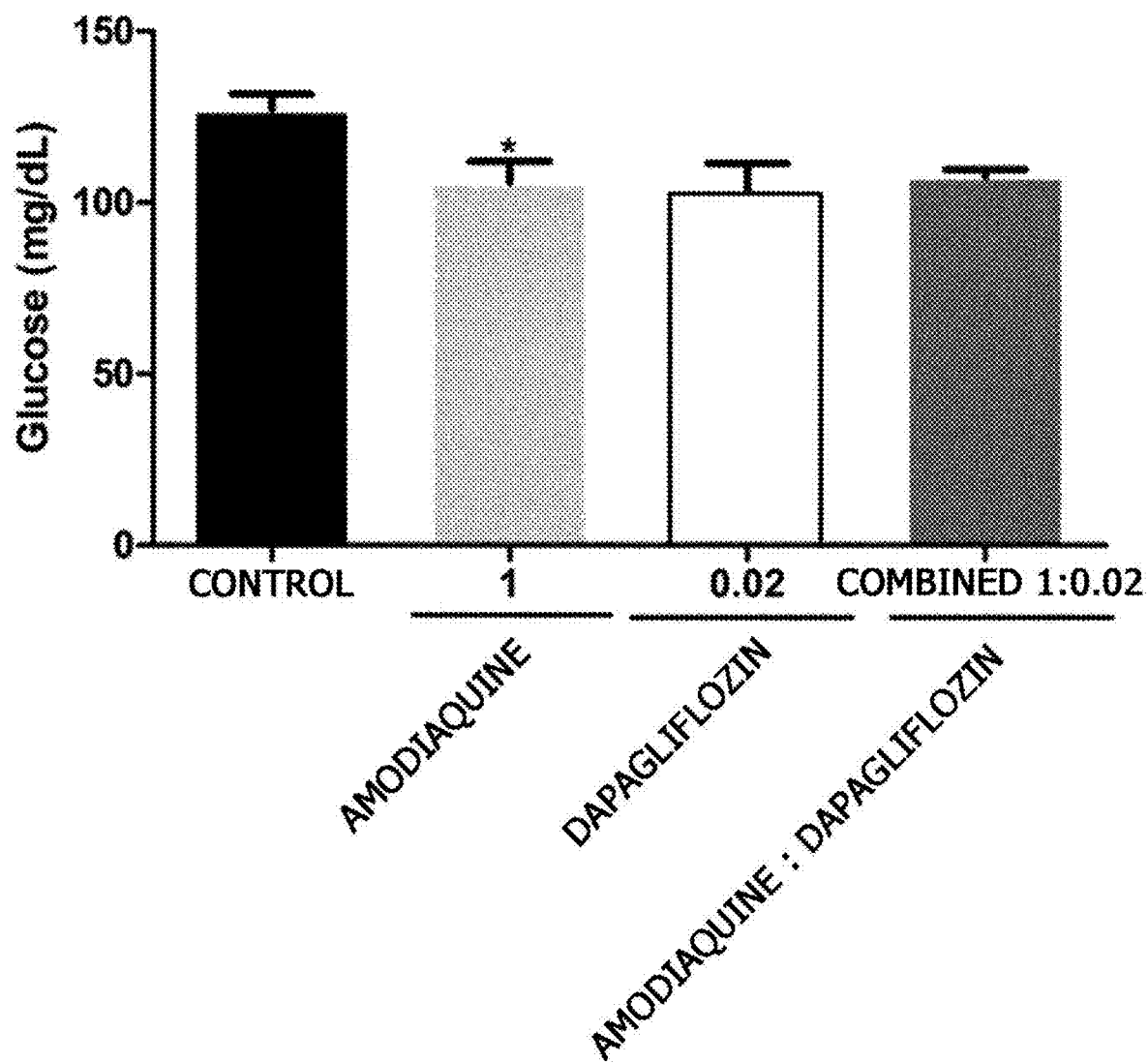
FIGS. 16A, 16B, and 16C are graphs showing results of confirming an effect on a change in fasting blood glucose of mice administered amodiaquine and dapagliflozin in weight ratios of 1:0.02, 1:0.2, and 1:2, respectively.
Figure 16B:
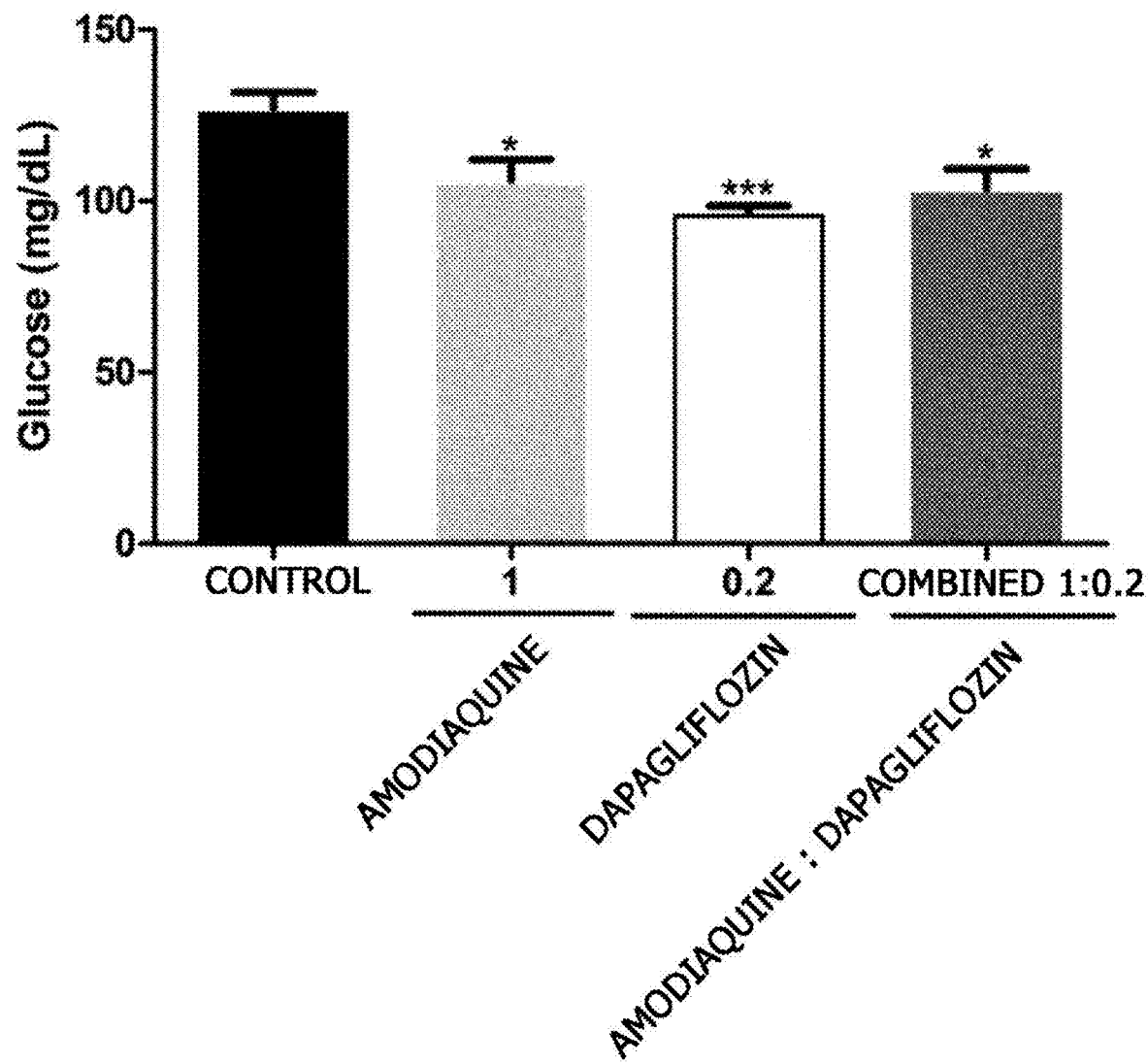
Figure 16C:
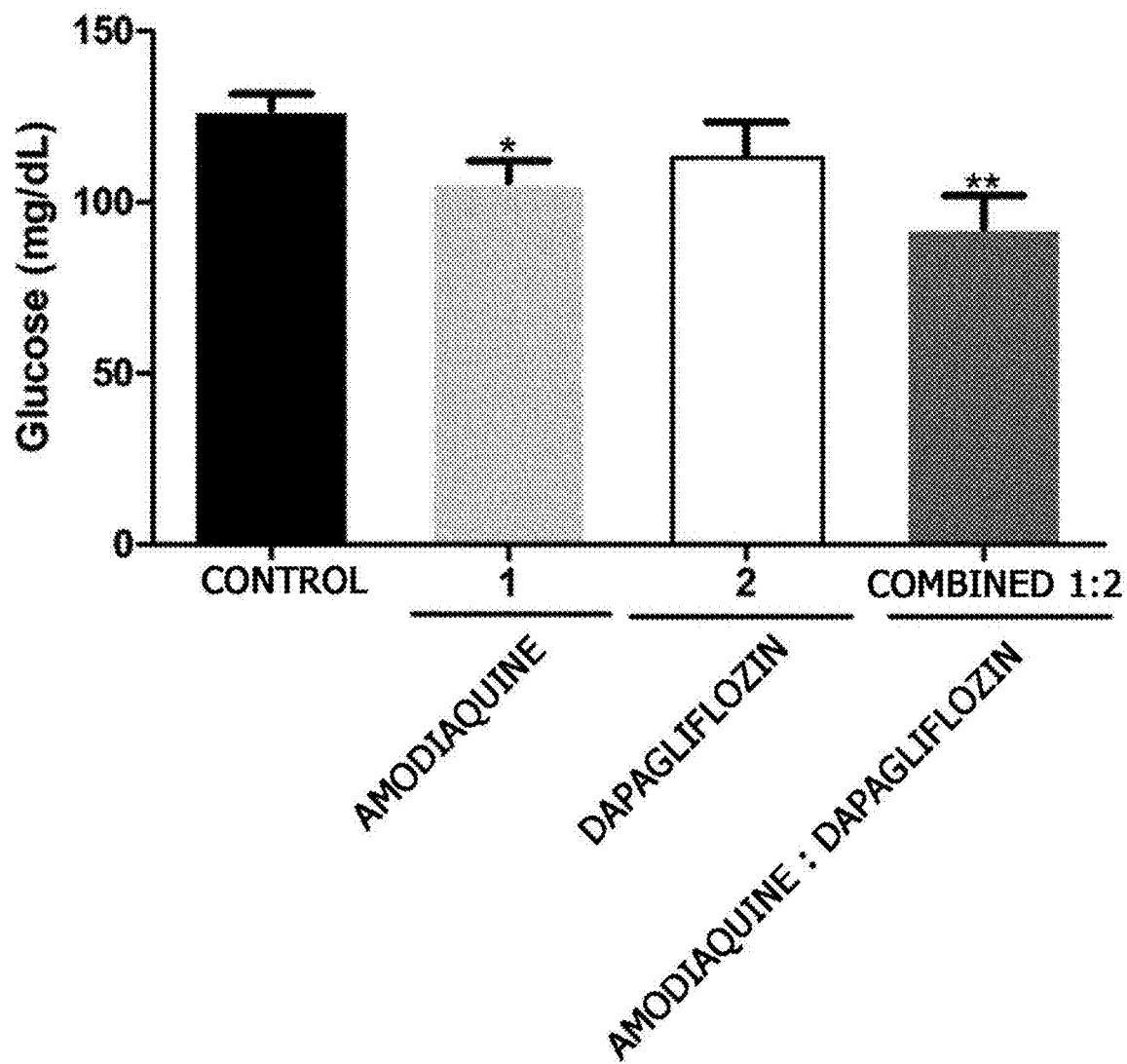

A fasting blood glucose concentration after 16-hour fasting was measured by collecting whole blood from the caudal vein on week 8 after drug treatment. A blood glucose strip (Green Cross, Gyeonggi-do, Korea) was used to measure blood glucose. For the experimental results, significance of the experimental group and the control was verified using a t-test, and the groups showed statistically significant differences (*p<0.05 and *p<0.005. As a result, as illustrated in FIGS. 16A to 16C, it was confirmed that a synergistic effect of significantly lowering fasting blood glucose was exhibited in the group administered the combined preparation of amodiaquine and dapagliflozin in a weight ratio of 1:2, not in weight ratios of 1:0.02 and 1:0.2, as compared to the amodiaquine- or dapagliflozin-administered group.

16-3. Measurement of Blood Glucose Regulation Effect in Mice

To identify the blood glucose regulation effect, 2 g/kg of glucose was intraperitoneally injected into control and experimental group animals after 16-hour fasting, and a blood glucose concentration was measured every 30 minutes for 2 hours. For measurement of the blood glucose concentration, an oral glucose tolerance test (OGTT) was used. For the experimental results, significance of the experimental groups and the control was verified using an independent group t-test, and the groups showed statistically significant differences (*p<0.05 and **p<0.005).

Figure 16D:
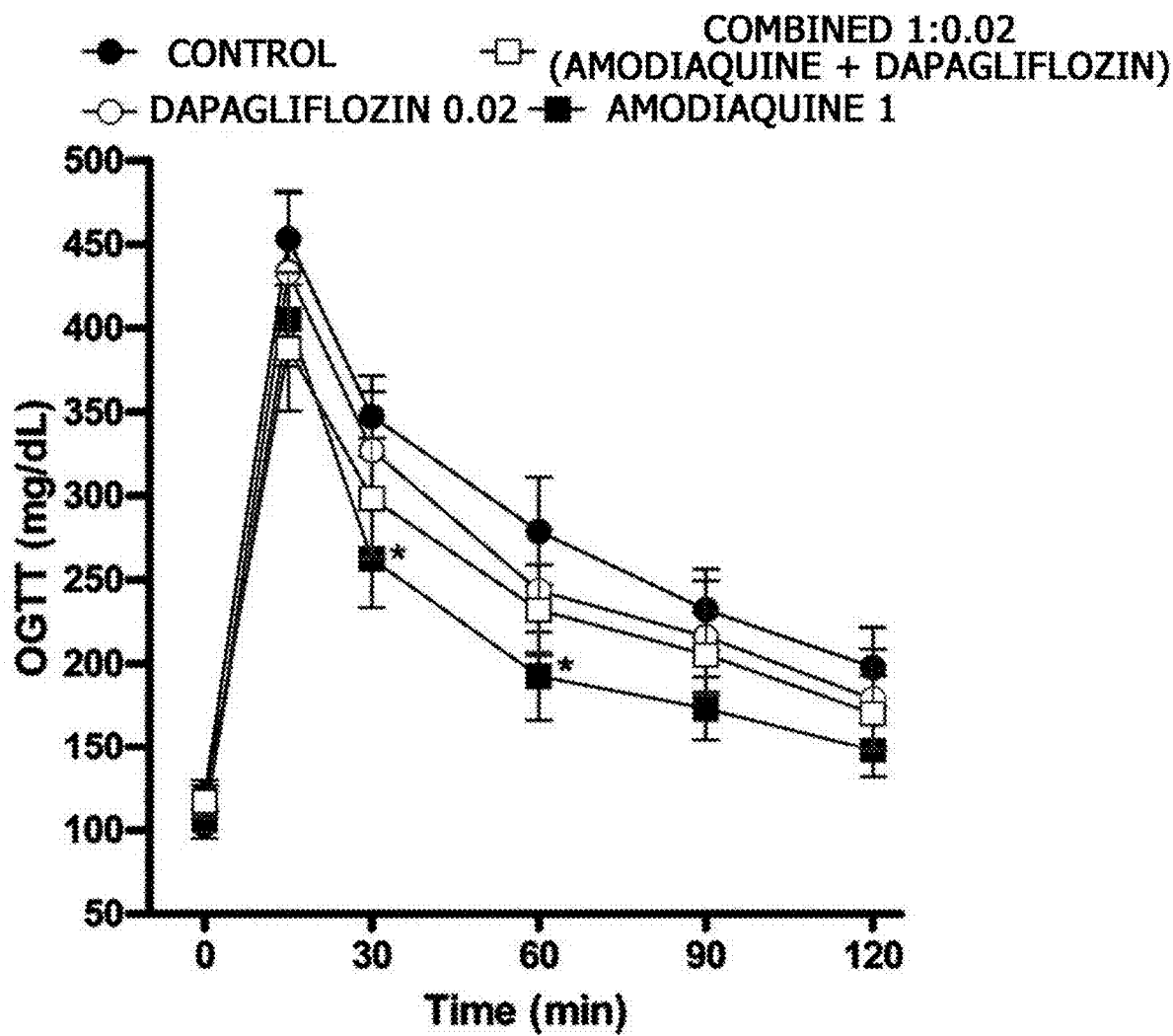
FIGS. 16D, 16E, and 16F are graphs showing OGTT results of confirming an effect on a change in blood glucose over time after glucose was administered to mice administered amodiaquine and dapagliflozin in weight ratios of 1:0.02, 1:0.2, and 1:2, respectively.
Figure 16E:
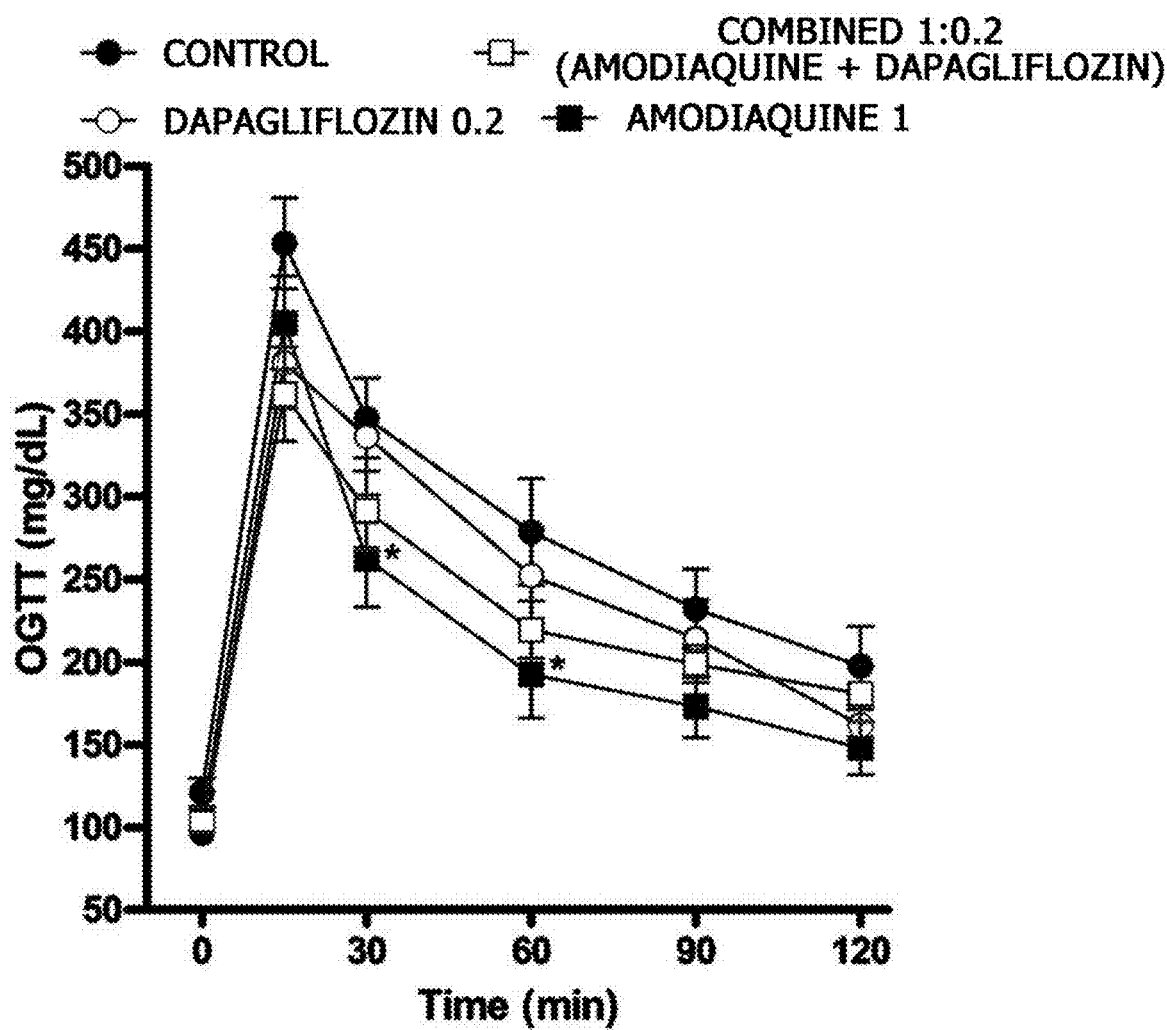
Figure 16F:
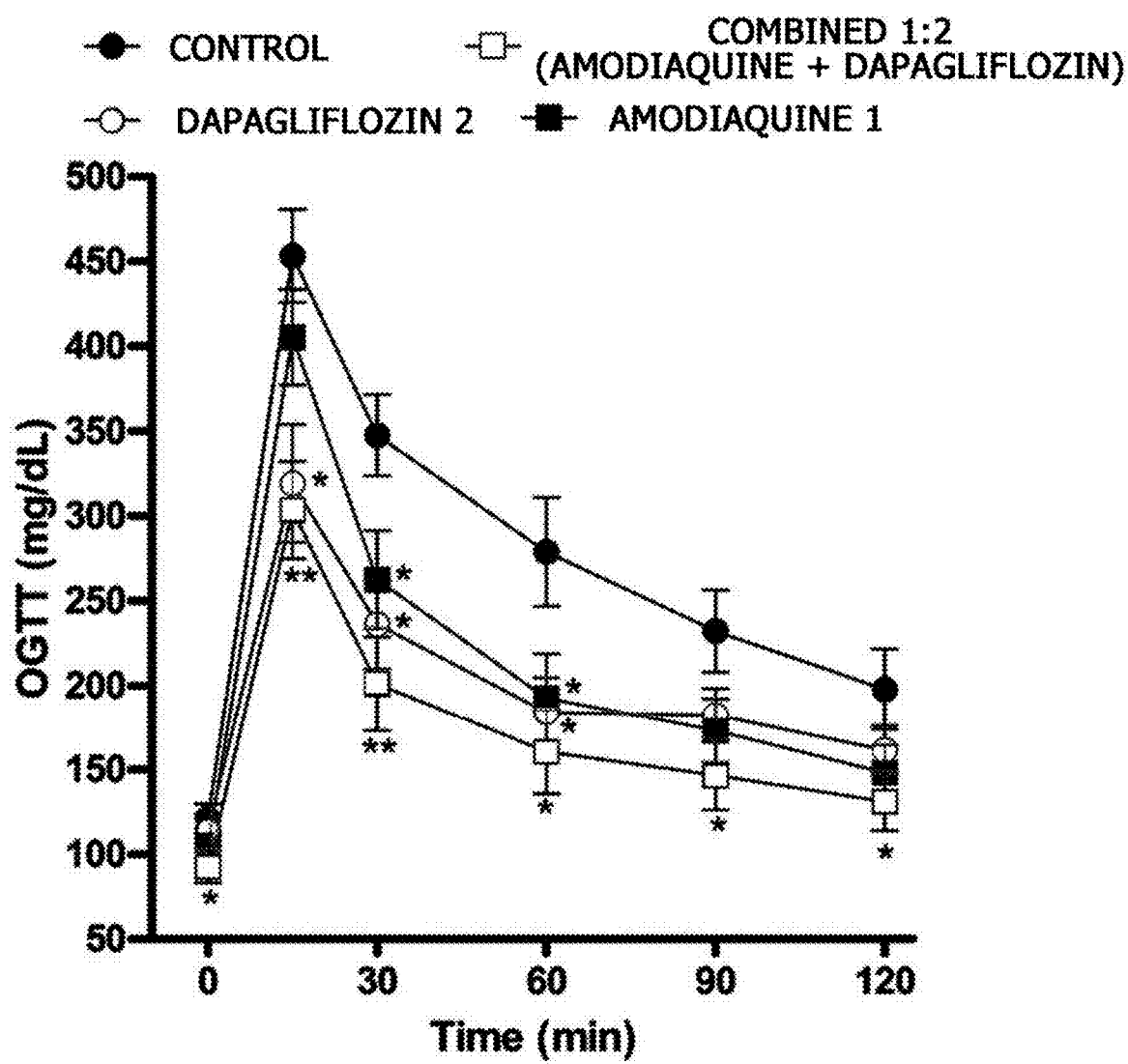

As a result, as illustrated in FIGS. 16D to 16F, it was confirmed that a blood glucose concentration 2 hours after glucose administration was rapidly reduced in the group administered the combined preparation of amodiaquine and dapagliflozin in a weight ratio of 1:2 not in weight ratios of 1:0.02 and 1:0.2, as compared to the amodiaquine- or dapagliflozin-administered group.

From the above result, it was confirmed that an excellent synergistic effect of reducing a blood glucose concentration was exhibited in the combined preparation-administered group as compared to the group administered amodiaquine or dapagliflozin alone, and thus it can be seen that the combined preparation of amodiaquine and dapagliflozin in a weight ratio of 1:2 may be effectively used for the prevention or treatment of diabetes and may also be effectively used as an agent for preventing or treating insulin-resistant type 2 diabetes.

16-4. Measurement of Glycated Hemoglobin in Mice

There are many methods of diagnosing diabetes such as blood glucose measurement, and the like, but the blood glucose measurement is inaccurate due to various factors such as diets, exercise, and the like, so it is one among effective methods to measure glycated hemoglobin in blood to manage and treat diabetes. In 1986, the American Diabetes Association started using the amount of glycated hemoglobin, which is a relatively stable index, as a diabetes management indicator by suggesting glycated hemoglobin measurement twice a year, in order to manage any type of diabetes (KR 10-2009-0006999, published on Jan. 16, 2009). In the present example, the glycated hemoglobin contents of mice due to administration of the combined preparation of amodiaquine and dapagliflozin were examined. To measure an effect of the combined preparation of amodiaquine and dapagliflozin on reducing glycated hemoglobin, whole blood was collected from the caudal vein of each of the control and experimental group animals and injected into a Hemoglobin A1c reagent kit, and then measurement was performed thereon using a DCA vantage analyzer (USA, New York, Siemens). For the experimental results, significance of the experimental groups and the control was verified using an independent group t-test, and the groups showed statistically significant differences (*$p<0.05$ and **$p<0.005$).

Figure 16G:
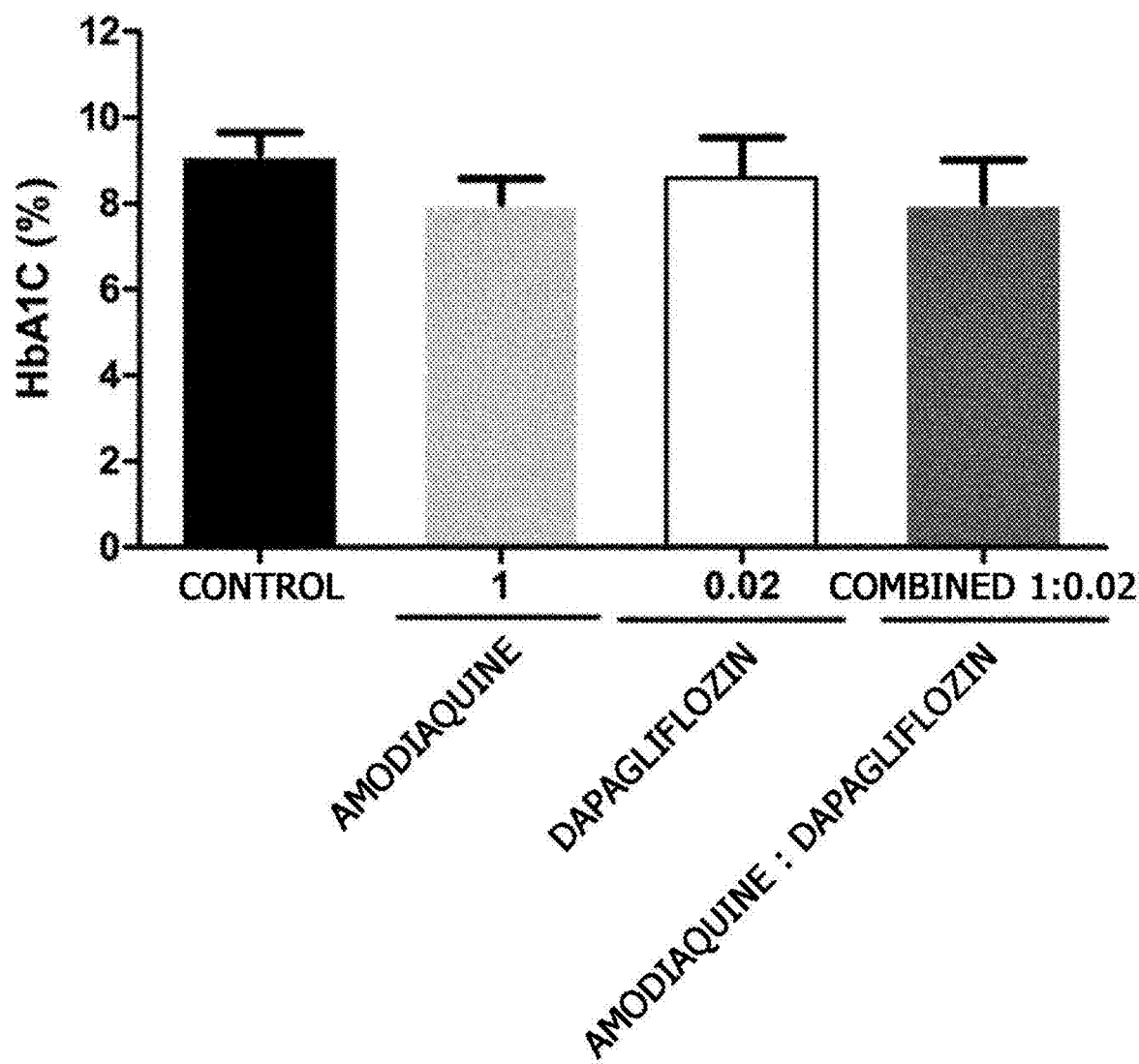
FIGS. 16G, 16H, and 16I are graphs showing results of confirming an effect on glycated hemoglobin levels of mice administered amodiaquine and dapagliflozin in weight ratios of 1:0.02, 1:0.2, and 1:2, respectively.
Figure 16H:
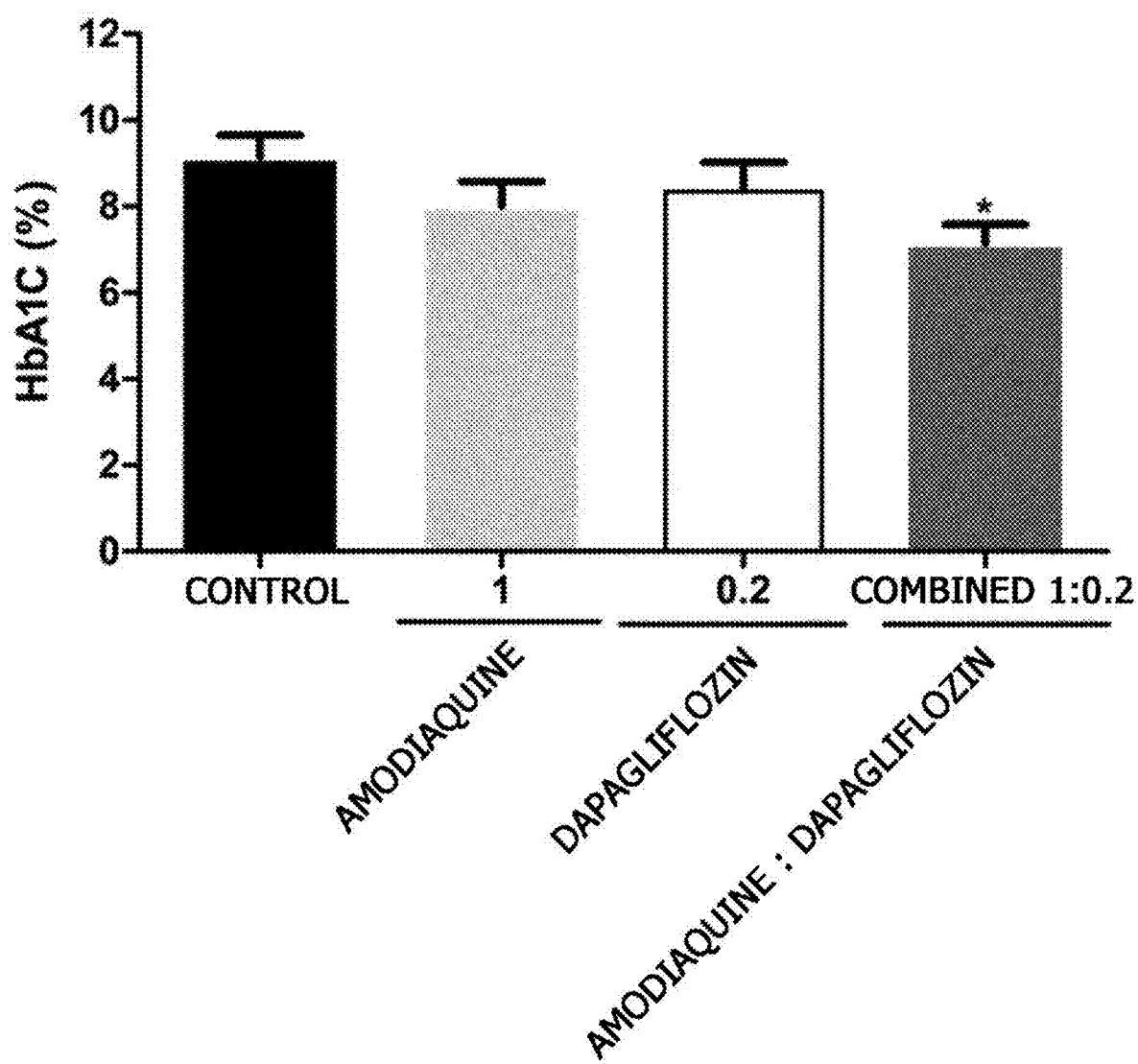
Figure 16I:
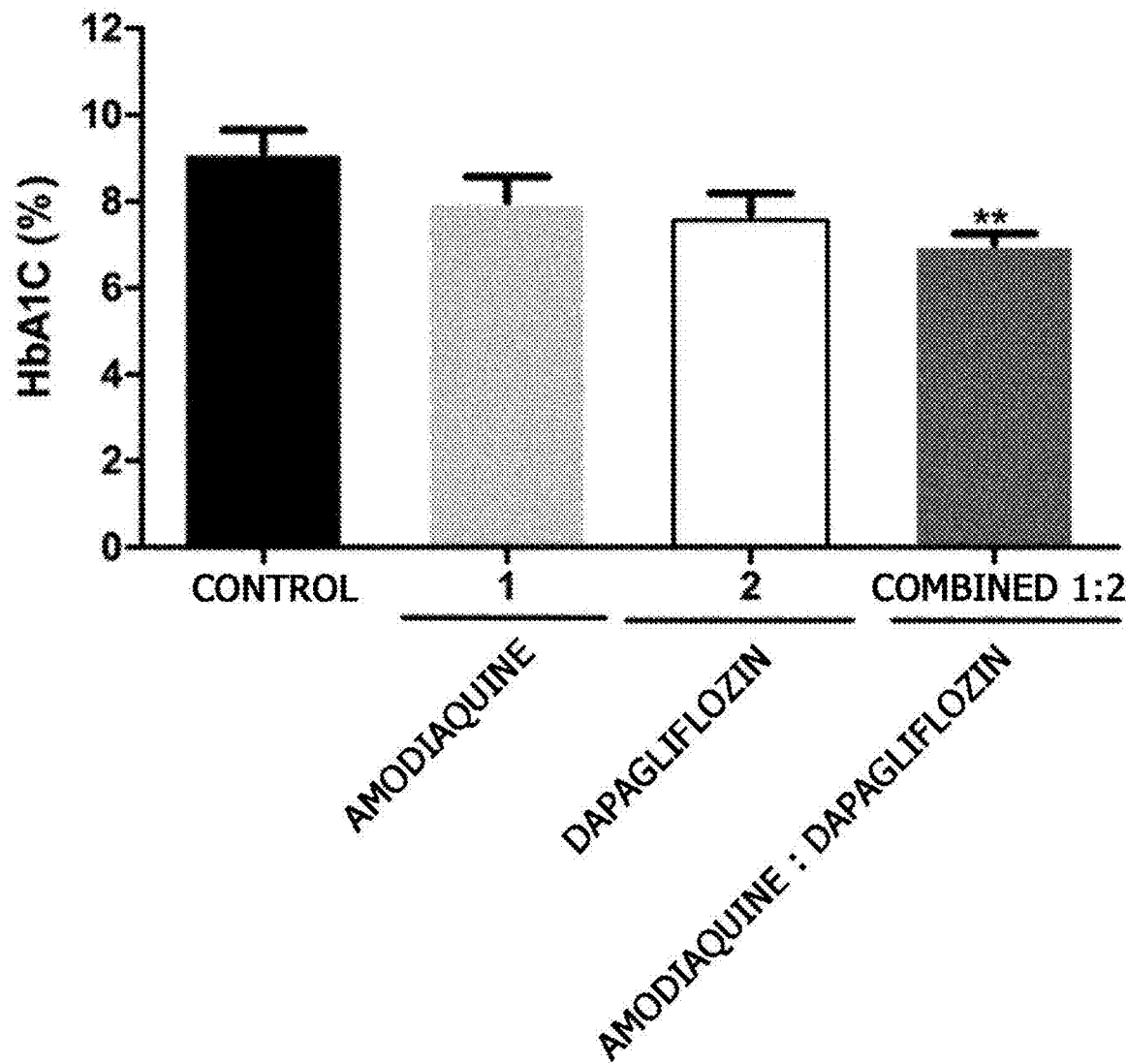

As a result, as illustrated in FIGS. 16G to 16I, it was confirmed that a glycated hemoglobin generation inhibitory effect was increased in the group administered the combined preparation of amodiaquine and dapagliflozin in a weight ratio of 1:0.2 or 1:2 not in a weight ratio of 1:0.02, as compared to the amodiaquine- or dapagliflozin-administered group.

From the above result, it was confirmed that the combined preparation of amodiaquine and dapagliflozin had an effect of reducing glycated hemoglobin, and thus it can be seen that the combined preparation may be effectively used as an agent for preventing or treating insulin-resistant type 2 diabetes.

Example 17. Effect of Administration of Combined Preparation of Amodiaquine and Exenatide on Blood Glucose Regulation in Mice 17-1. Administration of Amodiaquine or Exenatide or Combined Preparation Thereof To measure an effect of a combined preparation of amodiaquine and exenatide on blood glucose regulation, 6-week-old ob/ob mice were purchased from the Jackson Laboratory and raised under certain conditions (temperature: 22±2° C., relative humidity: 55±10%, and light/dark cycle: 12 hours). The mice were grouped into 7 individuals per group, freely fed water and diets in a cage, and then acclimated for 1 week before an experiment.

After acclimatization, the mice were divided into 6 groups, and orally administered amodiaquine or exenatide alone or a combined preparation thereof every other day for 8 weeks at weight ratios shown in Table 5 below.

TABLE 5

| Group | Amodiaquine | Exenatide |
|---|---|---|
| Normal control | — | — |
| Amodiaquine- or exenatide-administered group | 1 | — |
|  | — | 0.001 |
|  | — | 0.005 |
| Group administered combined preparation of Amodiaquine and exenatide | 1 | 0.001 |
|  | 1 | 0.005 |

17-2. Measurement of Blood Glucose Regulation Effect in Mice

To identify the blood glucose regulation effect, 2 g/kg of glucose was intraperitoneally injected into control and experimental group animals after 16-hour fasting, and a blood glucose concentration was measured every 30 minutes for 2 hours. For measurement of the blood glucose concentration, an oral glucose tolerance test (OGTT) was used. For the experimental results, significance of the experimental groups and the control was verified using an independent group t-test, and the groups showed statistically significant differences (*$p<0.05$, $p<0.005$, and *$p<0.0005$).

Figure 17A:
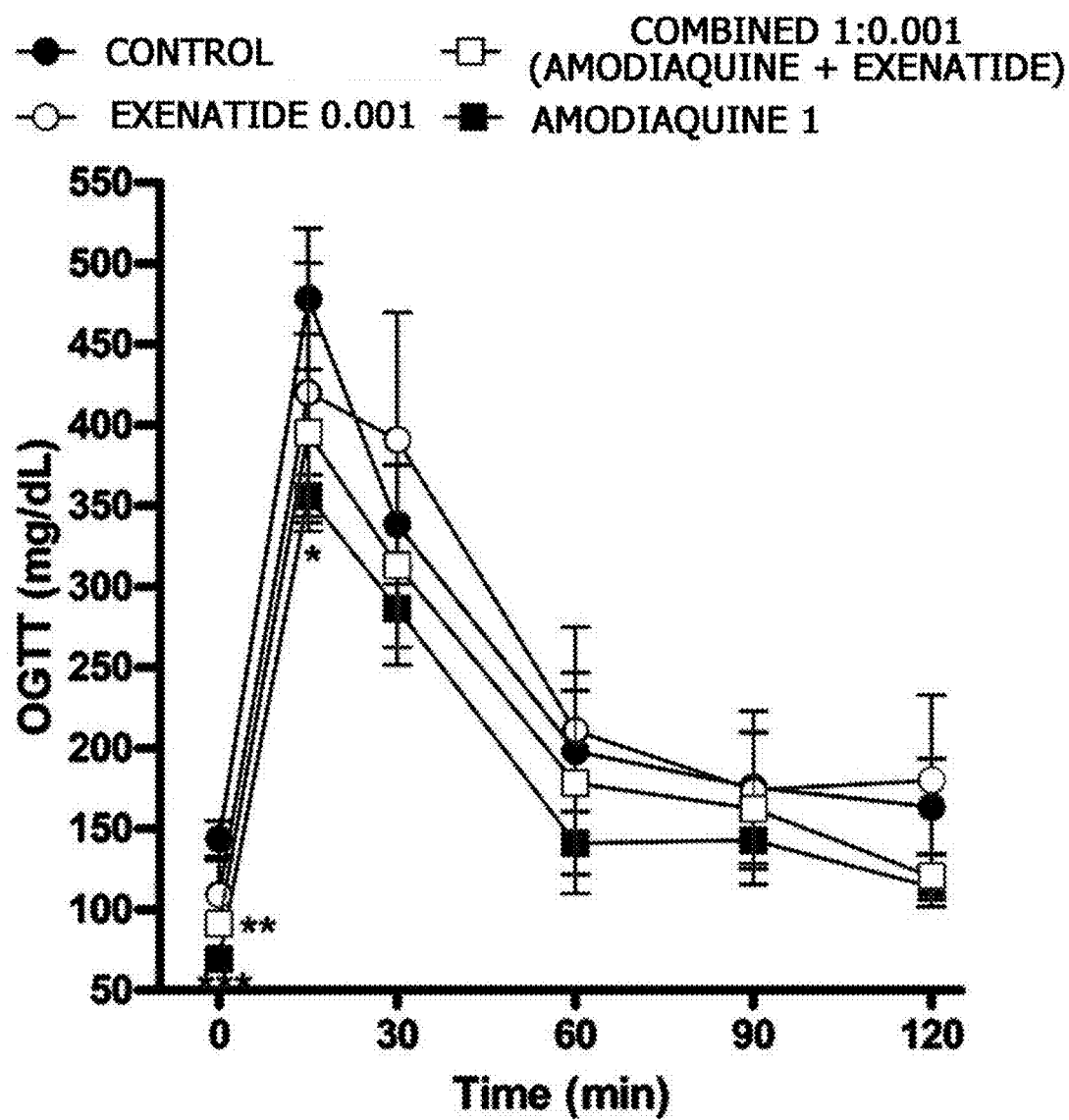
FIGS. 17A and 17B are graphs showing OGTT results of confirming an effect on a change in blood glucose over time after glucose was administered to mice administered amodiaquine and exenatide in weight ratios of 1:0.001 and 1:0.005, respectively.
Figure 17B:
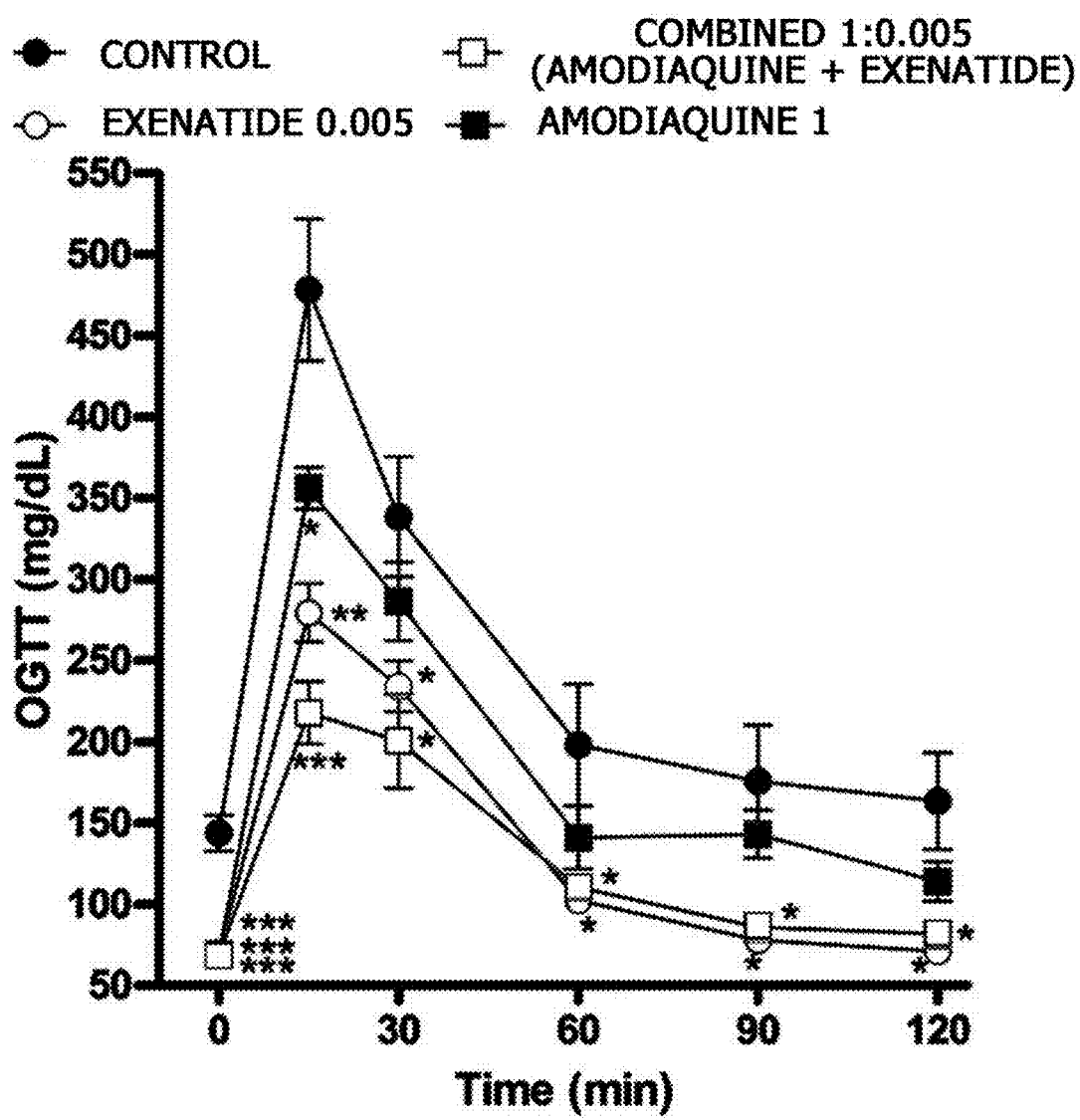

As a result, as illustrated in FIGS. 17A and 17B, it was confirmed that a blood glucose concentration 2 hours after glucose administration was rapidly reduced in the group administered the combined preparation of amodiaquine and exenatide in a weight ratio of 1:0.005, not in a weight ratio of 1:0.001, as compared to the amodiaquine- or exenatide-administered group.

From the above result, it was confirmed that an excellent synergistic effect of reducing a blood glucose concentration was exhibited in the combined preparation-administered group as compared to the group administered amodiaquine or exenatide alone, and thus it can be seen that the combined preparation of amodiaquine and exenatide in a weight ratio of 1:0.005 may be effectively used for the prevention or treatment of diabetes and may also be effectively used as an agent for preventing or treating insulin-resistant type 2 diabetes.

The foregoing description of the present invention is provided for illustrative purposes, and it will be understood by those of ordinary skill in the art to which the present invention pertains that the invention may be easily modified in many different forms without departing from the spirit or essential characteristics of the present invention. It is therefore to be understood that the above-described embodiments are illustrative in all aspects and not restrictive.

The invention claimed is:
1. A method for treating type 2 diabetes responding to peroxisome proliferator-activated receptor-gamma (PPAR-γ) activation and also treating a disease selected from the group consisting of obesity, dyslipidemia, a cardiovascular disease, fatty liver, a combination thereof which respond to peroxisome proliferator-activated receptor-alpha (PPAR-α) activation,
the method comprising administering, to a subject in need thereof,
(a) amodiaquine of the following Formula 1 or a pharmaceutically acceptable salt thereof:

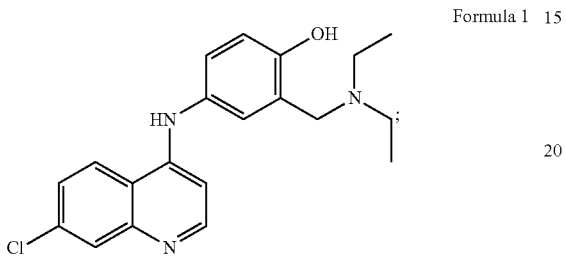

Formula 1 and
(b) one or more antidiabetic drugs selected from the group consisting of:
a biguanide drug selected from the group consisting of metformin, buformin, and phenformin;
an insulin sensitizer selected from the group consisting of troglitazone, ciglitazone, rosiglitazone, pioglitazone, and englitazone;
a dipeptidyl peptidase 4 (DPP-4) inhibitor selected from the group consisting of sitagliptin, linagliptin, vildagliptin, gemigliptin, saxagliptin, alogliptin, teneligliptin, anagliptin, and evogliptin;
a sodium-glucose co-transporter 2 (SGLT2) inhibitor selected from the group consisting of dapagliflozin, canagliflozin, empagliflozin, ipragliflozin, tofogliflozin, luseogliflozin, remogliflozin, remogliflozin etabonate, and ertugliflozin;
a glucagon-like peptide 1 (GLP1) agonist selected from the group consisting of exenatide, lixisenatide, liraglutide, albiglutide, and dulaglutide;
an insulin secretagogue selected from the group consisting of glybenclamide (glyburide), glipizide, gliclazide, glimepiride, tolazamide, tolbutamide, acetohexamide, carbutamide, chlorpropamide, glibornuride, gliquidone, glipentide, glisolamide, glisoxepide, glyclopyamide, glycylamide, glipentide, repaglinide, and nateglinide;
an α-glucosidase inhibitor selected from the group consisting of acarbose, voglibose, emiglitate, and miglitol;
a cannabinoid receptor 1 antagonist selected from the group consisting of rimonabant, otenabant, ibinabant, and surinabant; and
a composition comprising cyclo-his-pro, or a zinc salt and cyclo-his-pro.

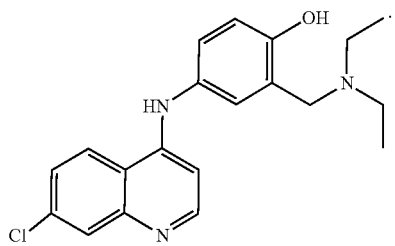 [SMILES: CCN(CC)Cc1cc(Nc2ccnc3cc(Cl)ccc23)ccc1O]

2. The method of claim 1, wherein the dyslipidemia comprises one or more selected from the group consisting of hyperlipidemia, hypertriglyceridemia, and hypercholesterolemia.

3. The method of claim 1, wherein a weight ratio of the amodiaquine and the one or more antidiabetic drugs is in a range of 1:0.01 to 1:500.

4. The method of claim 1, wherein a daily dose of the amodiaquine and the one or more antidiabetic drugs is in a range of 8 mg/kg to 20 mg/kg.

5. The method of claim 1, wherein a weight ratio of the amodiaquine and the bugyabude drug is in a range of 1:50 to 1:500.

6. The method of claim 1, wherein a weight ratio of the amodiaquine and the DPP-4 inhibitor is in a range of 1:1 to 1:20.

7. The method of claim 1, wherein a weight ratio of the amodiaquine and the SGLT2 inhibitor is in a range of 1:0.02 to 1:2.

8. The method of claim 1, wherein a weight ratio of the amodiaquine and the GLP1 agonist is in a range of 1:0.01 to 1:0.05.

* * * * *